United States Patent
Huang et al.

(10) Patent No.: US 12,329,890 B2
(45) Date of Patent: Jun. 17, 2025

(54) BLOOD TREATMENT SYSTEMS

(71) Applicant: Fresenius Medical Care Deutschland GmbH, Bad Homburg (DE)

(72) Inventors: Tommy Huang, Shanghai (CN); Dacey John Ryan, Suzhou (CN); Brad Yang, Shanghai (CN); Alain Veneroni, Spino d'Adda (IT)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 1256 days.

(21) Appl. No.: 17/093,028

(22) Filed: Nov. 9, 2020

(65) Prior Publication Data

US 2021/0138137 A1   May 13, 2021

Related U.S. Application Data

(60) Provisional application No. 62/934,243, filed on Nov. 12, 2019.

(51) Int. Cl.
*A61M 1/16* (2006.01)
*A61M 1/36* (2006.01)

(52) U.S. Cl.
CPC ........ *A61M 1/1698* (2013.01); *A61M 1/1601* (2014.02); *A61M 1/3622* (2022.05); *A61M 1/3627* (2013.01); *A61M 1/362227* (2022.05)

(58) Field of Classification Search
CPC .............. A61M 1/3627; A61M 1/1698; A61M 1/1601; A61M 1/3622; A61M 1/362227; A61M 2206/16
See application file for complete search history.

(56) References Cited

U.S. PATENT DOCUMENTS

| | | | |
|---|---|---|---|
| 3,920,556 | A | 11/1975 | Bowman |
| 3,970,438 | A | 7/1976 | Sama |
| 4,035,115 | A | 7/1977 | Hansen |
| 4,183,723 | A | 1/1980 | Hansen et al. |

(Continued)

FOREIGN PATENT DOCUMENTS

| | | |
|---|---|---|
| AU | 2016201358 | 5/2016 |
| EP | 0129345 | 12/1984 |

(Continued)

OTHER PUBLICATIONS

PCT International Search Report and Written Opinion in International Appln. No. PCT/EP2020/080854, mailed Feb. 8, 2021, 19 pages.

(Continued)

*Primary Examiner* — Ariana Zimbouski
(74) *Attorney, Agent, or Firm* — Fish & Richardson P.C.

(57) ABSTRACT

Dialyzer systems can consolidate multiple technologies and functionalities of blood treatment systems in a significantly integrated fashion. For example, this disclosure describes dialyzer systems that include a magnetically driven and magnetically levitating pump rotor integrated into the dialyzer. Such a dialyzer can be used with treatment modules that include a magnetic field-generating pump drive unit. In some embodiments, the dialyzers include pressure sensor chambers with flexible membranes with which corresponding pressure transducers of the treatment modules can interface to detect arterial and/or venous pressures.

22 Claims, 30 Drawing Sheets

(56) References Cited

U.S. PATENT DOCUMENTS

| | | | |
|---|---|---|---|
| 4,211,597 A | 7/1980 | Lipps et al. |
| 4,231,871 A | 11/1980 | Lipps et al. |
| 4,287,059 A | 9/1981 | Kume et al. |
| 4,293,413 A | 10/1981 | Schnell |
| 4,368,118 A | 1/1983 | Siposs |
| 4,575,324 A | 3/1986 | Sommer et al. |
| 4,762,480 A | 8/1988 | Winkler et al. |
| 4,919,802 A | 4/1990 | Katsura |
| 4,936,744 A | 6/1990 | Dosch et al. |
| 5,011,380 A | 4/1991 | Kovacs |
| 5,087,070 A | 2/1992 | O'Loughlin et al. |
| 5,270,004 A | 12/1993 | Cosentino et al. |
| 5,302,929 A | 4/1994 | Kovacs |
| 5,308,314 A | 5/1994 | Fukui et al. |
| 5,322,413 A | 6/1994 | Vescovini et al. |
| 5,328,461 A | 7/1994 | Utterberg |
| 5,330,425 A | 7/1994 | Utterberg |
| 5,360,317 A | 11/1994 | Clausen et al. |
| 5,458,459 A | 10/1995 | Hubbard et al. |
| 5,520,640 A | 5/1996 | Utterberg |
| 5,575,630 A | 11/1996 | Nakazawa et al. |
| 5,632,894 A | 5/1997 | White et al. |
| 5,679,906 A | 10/1997 | Van Cleve et al. |
| 5,683,231 A | 11/1997 | Nakazawa et al. |
| 5,693,008 A | 12/1997 | Brugger et al. |
| 5,695,471 A | 12/1997 | Wampler |
| 5,725,357 A | 3/1998 | Nakazeki et al. |
| 5,728,951 A | 3/1998 | Van Cleve et al. |
| 5,769,815 A | 6/1998 | Utterberg |
| 5,770,149 A | 6/1998 | Raible |
| 5,810,758 A | 9/1998 | Yamazaki et al. |
| 5,840,070 A | 11/1998 | Wampler |
| 5,941,813 A | 8/1999 | Sievers et al. |
| 5,980,741 A | 11/1999 | Schnell et al. |
| 5,983,947 A | 11/1999 | Utterberg |
| 6,010,623 A | 1/2000 | Schnell et al. |
| 6,019,824 A | 2/2000 | Schnell |
| 6,051,134 A | 4/2000 | Schnell et al. |
| 6,068,455 A | 5/2000 | Cowans |
| 6,074,180 A | 6/2000 | Khanwilkar et al. |
| 6,080,133 A | 6/2000 | Wampler |
| 6,093,001 A | 7/2000 | Burgreen et al. |
| 6,100,618 A | 8/2000 | Schoeb et al. |
| 6,117,342 A | 9/2000 | Schnell et al. |
| 6,158,984 A | 12/2000 | Cao et al. |
| 6,176,904 B1 * | 1/2001 | Gupta .................. B01D 29/908 96/219 |
| 6,183,220 B1 | 2/2001 | Ohara et al. |
| 6,224,829 B1 | 5/2001 | Piplani et al. |
| 6,227,797 B1 | 5/2001 | Watterson et al. |
| 6,227,817 B1 | 5/2001 | Paden |
| 6,234,998 B1 | 5/2001 | Wampler |
| 6,250,880 B1 | 6/2001 | Woodard et al. |
| 6,251,292 B1 | 6/2001 | Zuk, Jr. |
| 6,274,055 B1 | 8/2001 | Zuk, Jr. |
| 6,302,661 B1 | 10/2001 | Khanwilkar et al. |
| 6,368,083 B1 | 4/2002 | Wampler |
| 6,368,557 B1 | 4/2002 | Piplani et al. |
| 6,379,618 B1 | 4/2002 | Piplani et al. |
| 6,394,769 B1 | 5/2002 | Bearnson et al. |
| 6,398,955 B1 | 6/2002 | Fumiyama et al. |
| 6,402,818 B1 | 6/2002 | Sengupta |
| 6,428,747 B1 | 8/2002 | Dueri et al. |
| 6,431,826 B1 | 8/2002 | Schober |
| 6,451,257 B1 | 9/2002 | Flamer |
| 6,454,999 B1 | 9/2002 | Farhangnia et al. |
| 6,468,041 B2 | 10/2002 | Ozaki |
| 6,478,962 B1 | 11/2002 | Brockhoff et al. |
| 6,503,450 B1 | 1/2003 | Afzal et al. |
| 6,517,508 B1 | 2/2003 | Utterberg et al. |
| 6,517,732 B1 | 2/2003 | Brockhoff et al. |
| 6,547,530 B2 | 4/2003 | Ozaki et al. |
| 6,575,717 B2 | 6/2003 | Ozaki et al. |
| 6,589,030 B2 | 7/2003 | Ozaki |
| 6,595,762 B2 | 7/2003 | Khanwilkar et al. |
| 6,596,058 B2 | 7/2003 | Gerner et al. |
| 6,609,883 B2 | 8/2003 | Woodard et al. |
| 6,638,011 B2 | 10/2003 | Woodard et al. |
| 6,688,861 B2 | 2/2004 | Wampler |
| 6,718,827 B1 | 4/2004 | Lee et al. |
| 6,725,726 B1 | 4/2004 | Adolfs et al. |
| 6,746,416 B2 | 6/2004 | Hubbard et al. |
| 6,820,490 B2 | 11/2004 | Mittelstein et al. |
| 6,840,735 B2 | 1/2005 | Yaegashi et al. |
| 6,866,625 B1 | 3/2005 | Ayre et al. |
| 6,880,404 B2 | 4/2005 | Uberreiter |
| 6,884,210 B2 | 4/2005 | Nose et al. |
| 6,887,214 B1 | 5/2005 | Levin et al. |
| 6,942,447 B2 | 9/2005 | Ikeya |
| 6,966,748 B2 | 11/2005 | Woodard et al. |
| 7,021,148 B2 | 4/2006 | Kuhn et al. |
| 7,022,099 B2 | 4/2006 | Litzie et al. |
| 7,025,750 B2 | 4/2006 | Brugger et al. |
| 7,033,147 B2 | 4/2006 | Yanai et al. |
| 7,156,802 B2 | 1/2007 | Woodard et al. |
| 7,160,242 B2 | 1/2007 | Yanai |
| 7,220,354 B2 | 5/2007 | McLaughlin et al. |
| 7,357,858 B2 | 4/2008 | Schoeb |
| 7,422,565 B2 | 9/2008 | Delnevo et al. |
| 7,462,019 B1 | 12/2008 | Allarie et al. |
| 7,470,246 B2 | 12/2008 | Mori et al. |
| 7,476,077 B2 | 1/2009 | Woodard et al. |
| 7,513,163 B2 | 4/2009 | Fukutomi et al. |
| 7,556,611 B2 | 7/2009 | Kolenbrander et al. |
| 7,575,423 B2 | 8/2009 | Wampler |
| 7,603,907 B2 | 10/2009 | Reiter et al. |
| 7,648,627 B2 | 1/2010 | Beden et al. |
| 7,748,275 B2 | 7/2010 | Kouda et al. |
| 7,748,964 B2 | 7/2010 | Yaegashi et al. |
| 7,767,447 B2 | 8/2010 | Breidenthal et al. |
| 7,776,006 B2 | 8/2010 | Childers et al. |
| 7,780,336 B2 | 8/2010 | Breidenthal et al. |
| 7,798,985 B2 | 9/2010 | Engelhardt et al. |
| 7,803,628 B2 | 9/2010 | Glocker |
| 7,871,391 B2 | 1/2011 | Folden et al. |
| 7,871,462 B2 | 1/2011 | Yardimci et al. |
| 7,892,331 B2 | 2/2011 | Childers et al. |
| 7,892,332 B2 | 2/2011 | Prisco et al. |
| 7,901,579 B2 | 3/2011 | Brugger et al. |
| 7,921,723 B2 | 4/2011 | Reiter et al. |
| 7,976,271 B2 | 7/2011 | LaRose et al. |
| 7,988,768 B2 | 8/2011 | Yardimci et al. |
| 7,997,854 B2 | 8/2011 | LaRose et al. |
| 8,002,518 B2 | 8/2011 | Woodard et al. |
| 8,025,714 B2 | 9/2011 | Prisco et al. |
| 8,025,716 B2 | 9/2011 | Prisco et al. |
| 8,029,454 B2 | 10/2011 | Kelly et al. |
| 8,034,161 B2 | 10/2011 | Gura et al. |
| 8,038,639 B2 | 10/2011 | Lo et al. |
| 8,043,074 B2 | 10/2011 | Tada |
| 8,048,209 B2 | 11/2011 | Dannenmaier et al. |
| 8,048,375 B2 | 11/2011 | Breidenthal et al. |
| 8,052,929 B2 | 11/2011 | Breidenthal et al. |
| 8,096,186 B2 | 1/2012 | Butterfield |
| 8,104,352 B2 | 1/2012 | Evering et al. |
| 8,105,265 B2 | 1/2012 | Demers et al. |
| 8,113,060 B2 | 2/2012 | Jonsson et al. |
| 8,114,276 B2 | 2/2012 | Childers et al. |
| 8,123,503 B2 | 2/2012 | Shinshi et al. |
| 8,142,383 B2 | 3/2012 | Dannenmaier et al. |
| 8,162,152 B2 | 4/2012 | Omori et al. |
| 8,167,593 B2 | 5/2012 | Gohean et al. |
| 8,192,388 B2 | 6/2012 | Hogard |
| 8,206,580 B2 | 6/2012 | Dannenmaier et al. |
| 8,221,529 B2 | 7/2012 | Childers et al. |
| 8,221,705 B2 | 7/2012 | Breidenthal et al. |
| 8,226,373 B2 | 7/2012 | Yaegashi |
| 8,282,359 B2 | 10/2012 | Ayre et al. |
| 8,282,366 B2 | 10/2012 | Hilber et al. |
| 8,323,492 B2 | 12/2012 | Childers et al. |
| 8,329,030 B2 | 12/2012 | Childers et al. |
| 8,333,118 B2 | 12/2012 | Blankenship |
| 8,353,686 B2 | 1/2013 | Cook |
| 8,366,381 B2 | 2/2013 | Woodard et al. |

(56) References Cited

U.S. PATENT DOCUMENTS

| | | |
|---|---|---|
| 8,382,711 B2 | 2/2013 | Dudar et al. |
| 8,403,150 B2 | 3/2013 | Dannenmaier et al. |
| 8,414,686 B2 | 4/2013 | Gura et al. |
| 8,419,709 B2 | 4/2013 | Haddad et al. |
| 8,430,652 B2 | 4/2013 | Yaegashi et al. |
| 8,444,586 B2 | 5/2013 | Beck |
| 8,480,976 B2 | 7/2013 | Breidenthal et al. |
| 8,485,999 B2 | 7/2013 | Holmer et al. |
| 8,491,178 B2 | 7/2013 | Breidenthal et al. |
| 8,496,874 B2 | 7/2013 | Gellman et al. |
| 8,512,013 B2 | 8/2013 | LaRose et al. |
| 8,540,477 B2 | 9/2013 | LaRose et al. |
| 8,545,427 B2 | 10/2013 | Holmer et al. |
| 8,561,471 B2 | 10/2013 | Blankenship |
| 8,568,347 B2 | 10/2013 | Brieske et al. |
| 8,580,110 B2 | 11/2013 | Jonsson et al. |
| 8,596,999 B2 | 12/2013 | Shinshi et al. |
| 8,640,547 B2 | 2/2014 | Winkler et al. |
| 8,641,657 B2 | 2/2014 | Ribolzi et al. |
| 8,652,082 B2 | 2/2014 | Jonsson et al. |
| 8,657,733 B2 | 2/2014 | Ayre et al. |
| 8,672,611 B2 | 3/2014 | LaRose et al. |
| 8,708,943 B2 | 4/2014 | Caleffi et al. |
| 8,735,055 B2 | 5/2014 | Breidenthal et al. |
| 8,765,367 B2 | 7/2014 | Breidenthal et al. |
| 8,770,945 B2 | 7/2014 | Ozaki et al. |
| 8,784,083 B2 | 7/2014 | Dippel |
| 8,784,745 B2 | 7/2014 | Nelson et al. |
| 8,803,044 B2 | 8/2014 | Kienman et al. |
| 8,821,365 B2 | 9/2014 | Ozaki et al. |
| 8,827,661 B2 | 9/2014 | Mori |
| 8,827,663 B2 | 9/2014 | Cook |
| 8,828,654 B2 | 9/2014 | Nelson et al. |
| 8,834,403 B2 | 9/2014 | Kelly et al. |
| 8,834,719 B2 | 9/2014 | Childers et al. |
| 8,858,487 B2 | 10/2014 | Suzuki |
| 8,858,488 B2 | 10/2014 | Kelly et al. |
| 8,870,552 B2 | 10/2014 | Ayre et al. |
| 8,870,804 B2 | 10/2014 | Jonsson |
| 8,876,685 B2 | 11/2014 | Crosby et al. |
| 8,882,692 B2 | 11/2014 | Lo et al. |
| 8,888,470 B2 | 11/2014 | Demers et al. |
| 8,894,600 B2 | 11/2014 | Kelly et al. |
| 8,906,300 B2 | 12/2014 | Wang et al. |
| 8,926,540 B2 | 1/2015 | Lo et al. |
| 8,926,544 B2 | 1/2015 | Hogard |
| 8,932,006 B2 | 1/2015 | LaRose et al. |
| 8,932,469 B2 | 1/2015 | Childers et al. |
| 8,939,926 B2 | 1/2015 | Wieting et al. |
| 8,945,037 B2 | 2/2015 | Hasegawa et al. |
| 8,951,220 B2 | 2/2015 | Brieske et al. |
| 8,968,232 B2 | 3/2015 | Kamen et al. |
| 8,974,405 B2 | 3/2015 | Folden et al. |
| 8,985,969 B2 | 3/2015 | Hoshi et al. |
| 8,992,075 B2 | 3/2015 | Kamen et al. |
| 8,992,463 B2 | 3/2015 | Hogard et al. |
| 9,005,152 B2 | 4/2015 | Kelly et al. |
| 9,028,436 B2 | 5/2015 | Lo et al. |
| 9,028,691 B2 | 5/2015 | Grant et al. |
| 9,032,818 B2 | 5/2015 | Campbell et al. |
| 9,039,595 B2 | 5/2015 | Ayre et al. |
| 9,039,648 B2 | 5/2015 | Kelly et al. |
| 9,044,535 B2 | 6/2015 | Garzaniti et al. |
| 9,050,405 B2 | 6/2015 | LaRose et al. |
| 9,050,411 B2 | 6/2015 | Kelly et al. |
| 9,050,417 B2 | 6/2015 | Fini et al. |
| 9,067,005 B2 | 6/2015 | Ozaki et al. |
| 9,068,572 B2 | 6/2015 | Ozaki et al. |
| 9,072,830 B2 | 7/2015 | Kelly et al. |
| 9,072,831 B2 | 7/2015 | Kelly et al. |
| 9,072,843 B2 | 7/2015 | Kelly et al. |
| 9,089,635 B2 | 7/2015 | Reichenbach et al. |
| 9,109,601 B2 | 8/2015 | Mori |
| 9,127,680 B2 | 9/2015 | Yanai et al. |
| 9,132,215 B2 | 9/2015 | Ozaki et al. |
| 9,133,847 B2 | 9/2015 | Hijikata et al. |
| 9,133,854 B2 | 9/2015 | Okawa et al. |
| 9,144,641 B2 | 9/2015 | Kelly et al. |
| 9,155,825 B2 | 10/2015 | Kelly et al. |
| 9,164,008 B2 | 10/2015 | Fukano et al. |
| 9,168,333 B2 | 10/2015 | Kelly et al. |
| 9,173,986 B2 | 11/2015 | Heide et al. |
| 9,173,987 B2 | 11/2015 | Meyer et al. |
| 9,180,237 B2 | 11/2015 | Giordano et al. |
| 9,216,246 B2 | 12/2015 | Kelly et al. |
| 9,239,057 B2 | 1/2016 | Hoshi et al. |
| 9,242,032 B2 | 1/2016 | LaRose et al. |
| 9,272,082 B2 | 3/2016 | Demers et al. |
| 9,278,168 B2 | 3/2016 | Gellman et al. |
| 9,302,039 B2 | 4/2016 | Kelly et al. |
| 9,360,003 B2 | 6/2016 | Oerter |
| 9,364,599 B2 | 6/2016 | Giordano et al. |
| 9,364,602 B2 | 6/2016 | Kelly et al. |
| 9,371,826 B2 | 6/2016 | Yanai et al. |
| 9,381,285 B2 | 7/2016 | Ozaki et al. |
| 9,382,908 B2 | 7/2016 | Ozaki et al. |
| 9,387,286 B2 | 7/2016 | Kelly et al. |
| 9,403,126 B2 | 8/2016 | Fissell et al. |
| 9,404,825 B2 | 8/2016 | Katz et al. |
| 9,410,549 B2 | 8/2016 | Ozaki et al. |
| 9,415,150 B2 | 8/2016 | Hogard et al. |
| 9,421,313 B2 | 8/2016 | Kelly et al. |
| 9,429,160 B2 | 8/2016 | Tanaka et al. |
| 9,433,880 B2 | 9/2016 | Lean et al. |
| 9,435,706 B2 | 9/2016 | Fini et al. |
| 9,446,181 B2 | 9/2016 | Jonsson et al. |
| 9,458,451 B2 | 10/2016 | Heinz et al. |
| 9,468,557 B2 | 10/2016 | Wang et al. |
| 9,480,784 B2 | 11/2016 | Kelly et al. |
| 9,512,852 B2 | 12/2016 | Wampler et al. |
| 9,526,822 B2 | 12/2016 | Meyer et al. |
| 9,550,019 B2 | 1/2017 | Buck et al. |
| 9,550,020 B2 | 1/2017 | Kelly et al. |
| 9,555,182 B2 | 1/2017 | Wieting et al. |
| 9,556,873 B2 | 1/2017 | Yanai et al. |
| 9,572,919 B2 | 2/2017 | Kelly et al. |
| 9,592,326 B2 | 3/2017 | Takatani et al. |
| 9,597,442 B2 | 3/2017 | Wilt |
| 9,603,985 B2 | 3/2017 | Wilt et al. |
| 9,623,164 B2 | 4/2017 | Meyer et al. |
| 9,638,202 B2 | 5/2017 | Ozaki et al. |
| 9,642,961 B2 | 5/2017 | Kelly et al. |
| 9,649,419 B2 | 5/2017 | Giordano et al. |
| 9,649,420 B2 | 5/2017 | Giordano et al. |
| 9,675,745 B2 | 6/2017 | Kelly et al. |
| 9,700,662 B2 | 7/2017 | Strohhoefer et al. |
| 9,709,061 B2 | 7/2017 | Yanai et al. |
| 9,713,665 B2 | 7/2017 | Meyer et al. |
| 9,717,837 B2 | 8/2017 | Vincent |
| 9,744,506 B2 | 8/2017 | Fan et al. |
| 9,764,074 B1 | 9/2017 | Childers et al. |
| 9,777,732 B2 | 10/2017 | LaRose et al. |
| 9,795,728 B2 | 10/2017 | Grant et al. |
| 9,801,992 B2 | 10/2017 | Giordano et al. |
| 9,802,158 B2 | 10/2017 | Fissell et al. |
| 9,835,158 B2 | 12/2017 | Schob |
| 9,839,733 B2 | 12/2017 | Reichenbach et al. |
| 9,850,906 B2 | 12/2017 | Ozaki et al. |
| 9,855,377 B2 | 1/2018 | Childers et al. |
| 9,872,949 B2 | 1/2018 | Meyer et al. |
| 9,872,950 B2 | 1/2018 | Kelly et al. |
| 9,877,476 B2 | 1/2018 | Levesque et al. |
| 9,884,144 B2 | 2/2018 | Lo et al. |
| 9,889,243 B2 | 2/2018 | Kelly et al. |
| 9,901,666 B2 | 2/2018 | Cotter |
| 9,925,320 B2 | 3/2018 | Childers et al. |
| 9,945,838 B2 | 4/2018 | Doyle |
| 9,962,629 B2 | 5/2018 | Taylor et al. |
| 9,968,132 B2 | 5/2018 | Hon |
| 9,987,407 B2 | 6/2018 | Grant et al. |
| 9,995,310 B2 | 6/2018 | Graichen |
| 10,010,663 B2 | 7/2018 | Meyer et al. |
| 10,016,550 B2 | 7/2018 | Giordano et al. |
| 10,030,664 B2 | 7/2018 | Lin et al. |

(56) References Cited

U.S. PATENT DOCUMENTS

| | | |
|---|---|---|
| 10,080,834 B2 | 9/2018 | Federspiel et al. |
| 10,086,342 B2 | 10/2018 | Heinz et al. |
| 10,092,716 B2 | 10/2018 | Velzy et al. |
| 10,098,998 B2 | 10/2018 | Wilt |
| 10,143,787 B2 | 12/2018 | Kumano |
| 10,143,790 B2 | 12/2018 | Schiller et al. |
| 10,145,376 B2 | 12/2018 | Kumano |
| 10,155,078 B2 | 12/2018 | Giordano et al. |
| 10,155,080 B2 | 12/2018 | Lo et al. |
| 10,166,318 B2 | 1/2019 | Yu et al. |
| 10,172,989 B2 | 1/2019 | Giordano et al. |
| 10,177,627 B2 | 1/2019 | Noh et al. |
| 10,183,103 B2 | 1/2019 | Wiktor et al. |
| 10,183,109 B2 | 1/2019 | Kelly et al. |
| 10,188,784 B2 | 1/2019 | Katz et al. |
| 10,226,565 B2 | 3/2019 | Fini et al. |
| 10,245,361 B2 | 4/2019 | Yanai et al. |
| 10,245,369 B2 | 4/2019 | Kelly et al. |
| 10,245,370 B2 | 4/2019 | Kelly et al. |
| 10,258,729 B2 | 4/2019 | Gellman et al. |
| 10,265,449 B2 | 4/2019 | Wampler et al. |
| 10,293,096 B2 | 5/2019 | Kelly et al. |
| 10,300,184 B2 | 5/2019 | Cotter |
| 10,357,599 B2 | 7/2019 | Strohhoefer et al. |
| 10,369,265 B2 | 8/2019 | Wieting et al. |
| 10,371,152 B2 | 8/2019 | Yanai et al. |
| 10,389,207 B2 | 8/2019 | Schoeb |
| 10,420,872 B2 | 9/2019 | Meyer et al. |
| 10,426,883 B2 | 10/2019 | Kelly et al. |
| 10,426,884 B2 | 10/2019 | Labib et al. |
| 10,428,828 B2 | 10/2019 | Canatella et al. |
| 10,441,697 B2 | 10/2019 | Kamen et al. |
| 10,449,280 B2 | 10/2019 | Wilt et al. |
| 10,473,105 B2 | 11/2019 | Lin et al. |
| 10,500,327 B2 | 12/2019 | Grant et al. |
| 10,532,141 B2 | 1/2020 | Meyer et al. |
| 10,543,052 B2 | 1/2020 | Meyer et al. |
| 10,543,301 B2 | 1/2020 | Timms |
| 10,625,012 B2 | 4/2020 | Ritter |
| 2006/0222533 A1 | 10/2006 | Reeves et al. |
| 2009/0071911 A1 | 3/2009 | Folden et al. |
| 2011/0092875 A1 | 4/2011 | Beck |
| 2011/0283878 A1 | 11/2011 | Romanin |
| 2012/0277654 A1* | 11/2012 | Olson ............... B01D 63/025 422/48 |
| 2013/0126404 A1 | 5/2013 | Gronau et al. |
| 2013/0177459 A1 | 7/2013 | Weatherley |
| 2013/0180339 A1 | 7/2013 | Brugger |
| 2013/0233798 A1 | 9/2013 | Wiktor et al. |
| 2014/0124425 A1 | 5/2014 | Bou Akez |
| 2014/0150559 A1 | 6/2014 | Ishihara et al. |
| 2014/0217020 A1 | 8/2014 | Meyer et al. |
| 2015/0247503 A1 | 9/2015 | Seiss et al. |
| 2015/0285258 A1 | 10/2015 | Foster |
| 2016/0101226 A1 | 4/2016 | Beiriger |
| 2016/0131141 A1 | 5/2016 | Sato et al. |
| 2017/0143886 A1 | 5/2017 | Wilt et al. |
| 2017/0232173 A1 | 8/2017 | Perry et al. |
| 2017/0319086 A1 | 11/2017 | Masuda et al. |
| 2017/0340798 A1 | 11/2017 | Lindley et al. |
| 2018/0024022 A1 | 1/2018 | Beden |
| 2018/0080843 A1 | 3/2018 | Funamura et al. |
| 2018/0185567 A1 | 7/2018 | Madhani et al. |
| 2018/0207345 A1 | 7/2018 | Peters |
| 2018/0221559 A1 | 8/2018 | Ritter |
| 2018/0280604 A1 | 10/2018 | Hobro et al. |
| 2019/0105436 A1 | 4/2019 | Uchida |
| 2019/0125946 A1 | 5/2019 | Gartner et al. |
| 2019/0262523 A1 | 8/2019 | Gomes, II |
| 2019/0356195 A1 | 11/2019 | Holenstein |
| 2020/0405941 A1 | 12/2020 | Ikuma |
| 2021/0138136 A1 | 5/2021 | Fini et al. |
| 2021/0138144 A1 | 5/2021 | Kreber et al. |

FOREIGN PATENT DOCUMENTS

| | | |
|---|---|---|
| EP | 1027898 | 8/2000 |
| EP | 1398047 | 3/2004 |
| EP | 1509260 | 3/2005 |
| EP | 1529545 | 5/2005 |
| EP | 1532994 | 5/2005 |
| EP | 2600917 | 6/2013 |
| EP | 2488226 | 11/2013 |
| EP | 2697515 | 2/2014 |
| EP | 2719403 | 4/2014 |
| EP | 2735358 | 5/2014 |
| EP | 3018352 | 5/2016 |
| EP | 2906265 | 7/2016 |
| EP | 2750732 | 7/2017 |
| EP | 3263150 | 1/2018 |
| EP | 3326670 | 5/2018 |
| EP | 3357524 | 8/2018 |
| EP | 3530301 | 8/2019 |
| EP | 3578211 | 12/2019 |
| EP | 2207966 | 2/2020 |
| EP | 3606577 | 2/2020 |
| EP | 3416702 | 3/2020 |
| EP | 3362121 | 4/2020 |
| GB | 1544810 | 4/1979 |
| JP | 6571234 | 9/2019 |
| WO | WO 2006/053384 | 5/2006 |
| WO | WO 2013/017181 | 2/2013 |
| WO | WO 2018/187576 | 10/2018 |
| WO | WO 2019/143623 | 7/2019 |
| WO | WO 2019/189036 | 10/2019 |

OTHER PUBLICATIONS

International Preliminary Report on Patentability in International Appln. No. PCT/EP2020/080852, mailed May 27, 2022, 9 pages.
International Preliminary Report on Patentability in International Appln. No. PCT/EP2020/080853, mailed May 27, 2022, 13 pages.
International Preliminary Report on Patentability in International Appln. No. PCT/EP2020/080854, mailed May 27, 2022, 12 pages.
PCT International Search Report and Written Opinion in International Appln. No. PCT/EP2020/080853, mailed Mar. 5, 2021, 20 pages.
PCT International Search Report and Written Opinion in International Appln. No. PCT/EP2020/080852, mailed Dec. 10, 2020, 15 pages.
PCT Invitation to Pay Additional Fees and, Where Applicable, Protest Fee in International Appln. No. PCT/EP2020/080853, mailed Jan. 12, 2021, 14 pages.
PCT Invitation to Pay Additional Fees and, Where Applicable, Protest Fee in International Appln. No. PCT/EP2020/080854, mailed Dec. 10, 2020, 13 pages.

\* cited by examiner

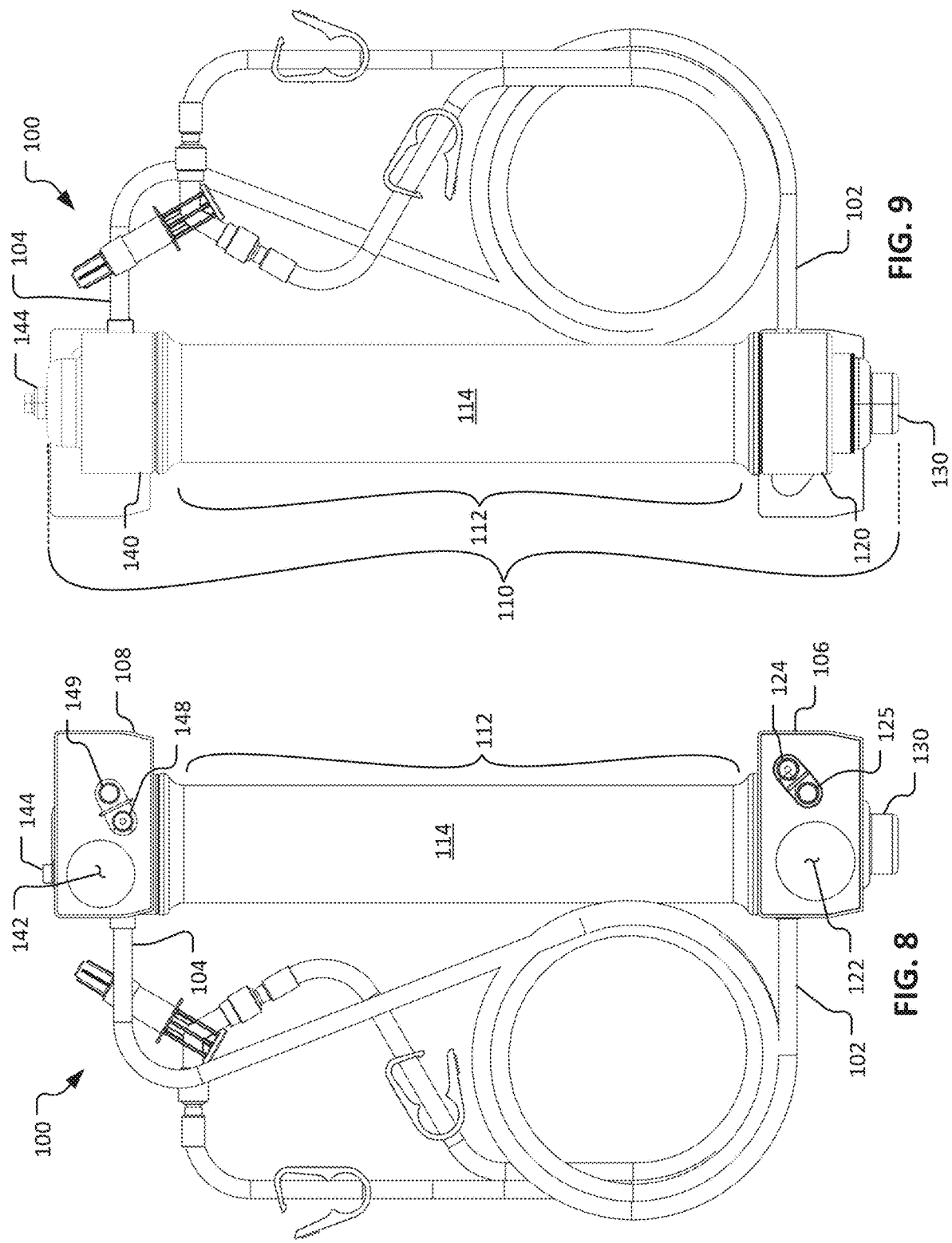

(SECTION A-A)

(SECTION B-B)

(SECTION C-C)

(SECTION D-D)

(SECTION E-E)

(SECTION B-B)

(SECTION F-F)

(SECTION G-G)

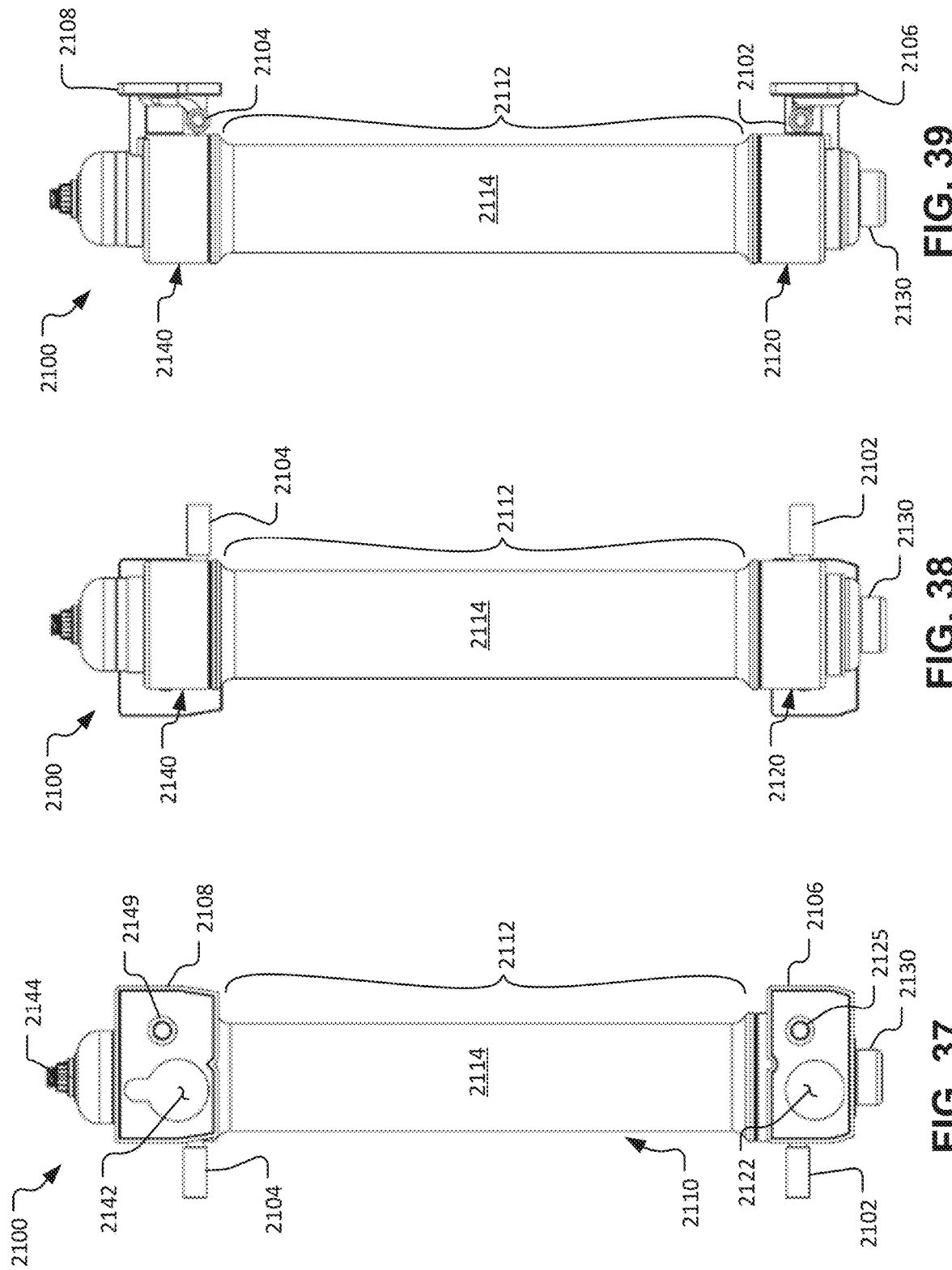

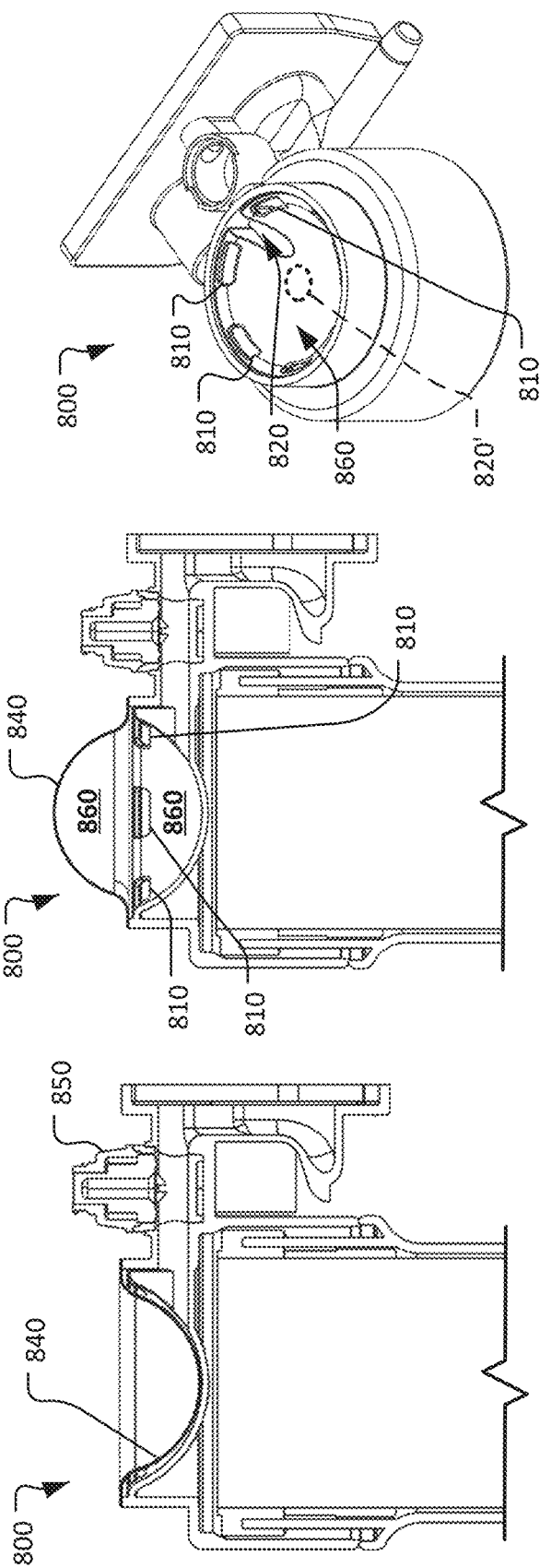

BLOOD TREATMENT SYSTEMS

CLAIM OF PRIORITY

This application claims priority under 35 USC § 119(e) to U.S. Patent Application Ser. No. 62/934,243, filed on Nov. 12, 2019, the entire contents of which are hereby incorporated by reference.

TECHNICAL FIELD

This invention relates to blood treatment systems and methods used for extracorporeal blood treatment procedures.

BACKGROUND

Renal dysfunction or failure and, in particular, end-stage renal disease, causes the body to lose the ability to remove water and minerals, maintain acid-base balance, and control electrolyte and mineral concentrations within physiological ranges. Toxic uremic waste metabolites, including urea, creatinine, and uric acid, accumulate in the body's tissues which can result in a person's death if the filtration function of the kidney is not replaced.

In treating chronic renal failure, various methods of purification and treatment of blood with machinery are used for removing substances usually eliminated with the urine and for withdrawing fluids. Diffuse mass transport is predominant in hemodialysis (HD), while in hemofiltration (HF) convective mass transport through a membrane is used. Hemodiafiltration (HDF) is a combination of the two methods.

During HD, blood passes from the patient through a dialyzer that includes a semi-permeable membrane to separate the blood from a large volume of externally-supplied dialysis solution, also referred to as dialysate. The waste and toxins, including excess fluids, dialyze out of the blood through the semi-permeable membrane into the dialysate, which is then typically discarded. The transportation of the small molecular substances through the semi-permeable membrane is determined mainly by the differences in concentration between the dialysate and the blood. The dialysate is referred to as "fresh dialysate" prior to receiving the dialyzed components of the blood, and the dialysate that exits the dialyzer after receiving the dialyzed components is referred to as "spent dialysate."

During HDF, part of the serum withdrawn through the semi-permeable membrane is replaced by a sterile substitution fluid which is passed to the extracorporeal blood stream either upstream of the dialyzer or downstream of the dialyzer. The supply of substitution fluid upstream of the dialyzer is also referred to as pre-dilution, and the supply downstream of the dialyzer is also referred to as post-dilution.

SUMMARY

Dialyzer systems described herein can include a magnetically driven and magnetically levitating pump rotor integrated into the dialyzer. Such a dialyzer is configured for use with treatment modules described herein that include a magnetic field-generating pump drive unit. In some embodiments, the dialyzers include pressure sensor chambers with flexible membranous walls against which corresponding pressure transducers of the treatment modules can interface to detect arterial and/or venous pressures. Additional features, as described herein, can be incorporated into the dialyzers and treatment modules to consolidate components, simplify setup, and enhance blood treatment performance.

In one aspect, the disclosure is directed to a deaeration chamber. The medical fluid deaeration chamber includes a housing including a top portion and a bottom portion. The housing defines a central axis and a chamber between the top and bottom portions. The medical fluid deaeration chamber also includes an inlet passage member extending within the chamber from the bottom portion. The inlet passage member extends toward the top portion along the central axis. An end portion of the inlet passage member defines a spiral-channel outlet through which liquid enters the chamber. The bottom portion defines a chamber outlet below the spiral-channel outlet.

Such a deaeration chamber may optionally include one or more of the following features in any combination(s). In some embodiments, the top portion includes a dome that partially defines the chamber. The chamber outlet may be positioned on an opposite side of the spiral-channel outlet in comparison to the dome. The medical fluid deaeration chamber may also include an air purge member attached to the dome to allow gases to exit the chamber while preventing liquids from exiting therethrough. In some embodiments, the dome is hemi-spherical. The spiral-channel outlet may be offset from the central axis of the housing. The chamber outlet may be offset from the central axis of the housing. In some embodiments, the housing includes a port for administering medicaments or extracting a sample of the liquid. The spiral-channel outlet may include a beveled surface at an acute angle in relation to the central axis. In some embodiments, the spiral-channel outlet is closer to a top of the chamber than to a bottom of the chamber. In some embodiments, the deaeration chamber is a medical fluid deaeration chamber. In some embodiments, the deaeration chamber is a blood deaeration chamber.

In another aspect, this disclosure is directed to a dialysis treatment apparatus. The dialysis treatment apparatus includes an elongate housing defining a central longitudinal axis and including first and second end caps at opposite ends of the housing. The dialysis treatment apparatus also includes a plurality of hollow membranous fibers within an interior of the housing between the first and second end caps. The second end cap defines a chamber and an inlet passage member extending within the chamber along the central longitudinal axis from a bottom of the chamber toward a top of the chamber. The second end cap is configured such that when a liquid passes through the hollow membranous fibers the liquid enters the inlet passage member and passes through spiral-channel outlet of the inlet passage member to enter the chamber. The second end cap defines a chamber outlet below the spiral-channel outlet.

Such a dialysis treatment apparatus may optionally include one or more of the following features in any combination(s). The dialysis treatment apparatus may comprise a dialyzer. The chamber outlet may be defined by the bottom of the chamber. The spiral-channel outlet may be offset from the central longitudinal axis of the housing. The chamber outlet may be positioned between the spiral-channel outlet and the plurality of hollow membranous fibers. In some embodiments, the chamber outlet is offset from the central longitudinal axis of the housing. The second end cap may include a dome that partially defines the chamber. The dome may be hemi-spherical. The chamber may be configured to de-aerate the liquid flowing into the second end cap. The second end cap may define a substituate liquid inlet port in fluid communication with an outgoing fluid flow path exiting from the chamber. The dialysis treatment apparatus may also include a check valve along the outgoing fluid flow path. In some embodiments, the second end cap includes a port for administering medicaments or extracting a sample of the liquid. The dialysis treatment apparatus may also include an air purge member attached to the second end cap to allow gases to exit the chamber while preventing liquids from exiting therethrough. The dialysis treatment apparatus may also include a pump rotor within the housing. The pump rotor may be magnetically-drivable to force fluid (e.g., blood) through the housing and/or through lumens of a plurality of hollow membranous fibers within the housing. The dialysis treatment apparatus may be configured to direct the fluid (e.g., blood) to enter the first end cap transverse to the longitudinal axis of the dialysis treatment apparatus. The first end cap may be configured to deliver the fluid to a center of the pump rotor. After radially exiting the pump rotor, the fluid may enter a toroidal space defined around the pump rotor by the first end cap. From the toroidal space, the fluid may be directed by the first end cap to flow toward the hollow fibers. Prior to reaching the hollow fibers, the fluid may pass through one or more openings defined by an internal support plate within the first end cap. The housing may include a first end cap that defines a blood inlet and/or a second end cap that defines a blood outlet. The dialysis treatment apparatus may also include an arterial pressure detection chamber arranged between the blood inlet and the hollow fibers and having a first flexible surface. The first flexible surface may be attached to the first end cap. The first end cap may define a first dialysate port. The dialysis treatment apparatus can also include a venous pressure detection chamber arranged in the second end cap between the hollow fibers and the blood outlet. The venous pressure detection chamber can have a second flexible surface.

Embodiments can include one or more of the following advantages.

In some embodiments, multiple technologies and functionalities of blood treatment systems are consolidated in a significantly refined and integrated fashion into the dialyzer and treatment module systems described herein. For example, in some embodiments a single dialyzer unit as described further below can replace significant portions of a conventional hollow-fiber dialyzer, tubing set, air removal system, sample port, and pump. Moreover, the end caps of some dialyzers described herein can include accessible pressure chambers with flexible membranous walls for convenient measuring of arterial and venous pressures in a non-invasive manner. In some embodiments, the end caps of the dialyzers can include (a) a port to receive fresh dialysate fluid from the treatment module and (b) a port to return spent dialysate fluid to the treatment module after passing over the dialysis membrane. In some embodiments, the end caps of the dialyzers can also include ports by which substitute liquid can be directly added to the blood prior to and/or after the blood passes through the hollow fiber blood treatment section of the dialyzer. Additionally, in some embodiments, the same dialyzer and treatment module systems are configured for carrying out any of multiple different types of blood treatments, including, for example, HD and HDF.

In contrast to typical HD and HDF machines, some example embodiments reduce the number of required setup steps, which may result in reduced setup time and reduced opportunity for human error. In a clinic setting, this can free up valuable nursing resources and streamline patient care. This simplification can free up nursing or other personnel resources in a clinic or home setting, and also makes the process easier and more feasible for patients to set up the dialysis machine themselves.

In some embodiments, the consolidated dialyzer and treatment module systems described herein, provide important functional advantages. For example, the consolidation can reduce the amount of tubing needed for the extracorporeal circuit to be used for a blood treatment session. Moreover, the treatment module can be mounted on an arm extending from a blood treatment machine console so that the treatment module and dialyzer can be located very close to a patient. These features allow the length of extracorporeal tubing needed for a blood treatment session to be significantly minimized. Accordingly, the volume of priming solution required is advantageously reduced. Additionally, exposure of the patient's blood to contact with foreign surfaces is also advantageously reduced. The consolidated form factor also gives rise to additional advantages such as less potential for leaks, less hemolysis, less biohazard waste, less packaging waste, and reduced transportation expenses.

In some embodiments, a magnetic pump rotor is integrated to the dialyzer in a liquid-tight manner. Such an integrated pump rotor can be bearing-less, magnetically levitated, and rotationally driven by an external pump drive unit that generates dynamic magnetic fields. This arrangement provides advantages such as lower hemolysis as compared to conventional pumping systems used for extracorporeal blood treatments, and a bearing-free design that reduces system maintenance requirements and the potential for contamination. Moreover, since the pump drive unit and pump rotor are separated, easier cleaning of machine interfaces is advantageously facilitated.

In some embodiments, the consolidated dialyzer and treatment module systems described herein are also easier to set-up and use as compared to conventional systems. Accordingly, set-up times can be reduced and potential for errors can be mitigated. In result, the treatment costs per patient can be reduced in some embodiments.

The details of one or more embodiments are set forth in the accompanying drawings and the description below. Other aspects, features, and advantages will be apparent from the description and drawings, and from the claims.

DESCRIPTION OF DRAWINGS

FIG. 8 is a rear view of the dialyzer of the blood treatment system of FIG. 1.

FIG. 9 is a front view of the dialyzer of the blood treatment system of FIG. 1.

FIG. 37 is a rear view of an example dialyzer that is configured similar to the dialyzer of the blood treatment system of FIG. 1, except without HDF capability.

FIG. 38 is a front view of the dialyzer of FIG. 37.

FIG. 39 is a side view of the dialyzer of FIG. 37.

FIG. 45 is a longitudinal cross-sectional view of another alternative second (venous) end cap. The venous end cap is shown in a first configuration.

FIG. 46 is a longitudinal cross-sectional view of the venous end cap of FIG. 45 in a second configuration.

FIG. 47 is a perspective view showing a portion of the venous end cap of FIG. 45.

Like reference symbols in the various drawings indicate like elements.

DETAILED DESCRIPTION

This disclosure describes dialyzer systems that can include a magnetically driven, magnetically levitating pump rotor integrated into the dialyzer. Such a dialyzer can be used with treatment modules described herein that include a dynamic magnetic field-generating pump drive unit. In some embodiments, the dialyzer includes one or more pressure sensor chambers with flexible exterior membrane walls with which corresponding pressure transducers of the treatment modules interface to detect arterial and/or venous pressures. The dialyzer systems described herein consolidate multiple diverse technologies and functionalities of blood treatment systems in a significantly integrated fashion to consolidate components, reduce costs, simplify setup, and enhance performance.

Figure 1:
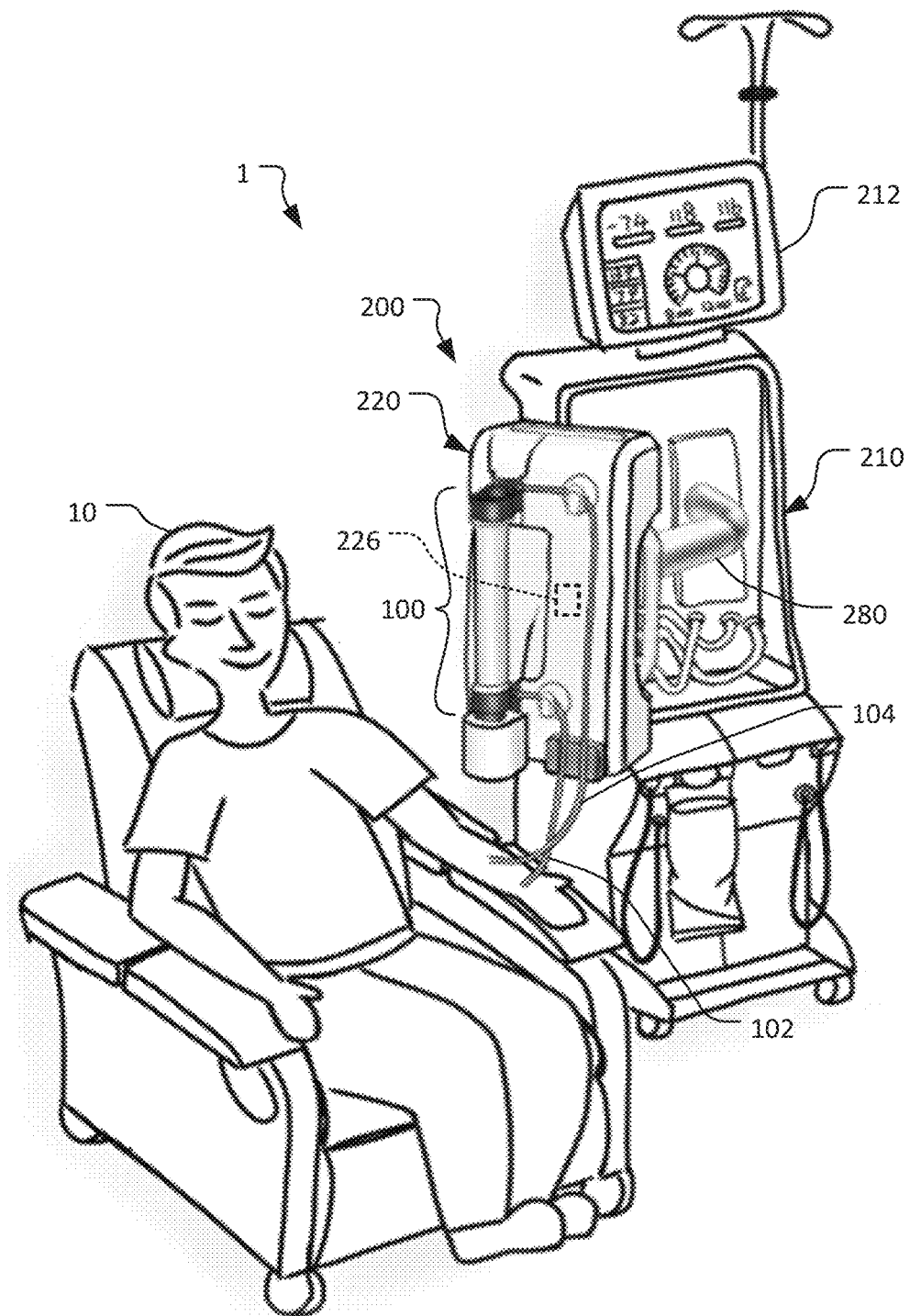
FIG. 1 depicts a patient receiving an extracorporeal blood treatment using a blood treatment system.

With reference to FIG. 1, a patient 10 is depicted as receiving an extracorporeal blood treatment using a blood treatment system 1 that includes a disposable set connected to a blood treatment machine 200. The disposable set includes a dialyzer 100 that is coupled to a treatment module 220 of the blood treatment machine 200. In some cases, the patient 10 may receive treatment for a health condition such as renal failure. Accordingly, the system 1 can be used to provide one or more types of treatment to the patient 10, including hemodialysis (HD), hemodiafiltration (HDF), or some other type of blood treatment. For such treatments, blood is withdrawn from the patient 10 via an arterial line 102 and, after passing through the dialyzer 100, treated blood is returned to the patient 10 via a venous line 104. The dialyzer 100 is a single-use disposable item, whereas the blood treatment machine 200 is a durable reusable system. In some cases, a single dialyzer 100 may be reused two or more times for a particular individual patient.

The blood treatment machine 200 includes a blood treatment machine console 210, the treatment module 220, and an arm 280 that connects the treatment module 220 to the blood treatment machine console 210. The arm 280 extends from the blood treatment machine console 210, and the treatment module 220 is mounted to the other end of the arm 280. In other words, the treatment module 220 is cantilevered from the blood treatment machine console 210 by the arm 280.

The arm 280 includes one or more adjustable joints so that the arm 280 can be manually articulated to position the treatment module 220 in various positions/orientations relative to the blood treatment machine console 210 and/or relative to the patient 10. For example (as depicted in FIG. 1), in some cases the arm 280 can be extended so that the treatment module 220 is positioned close to the patient 10. Accordingly, the arterial line 102 and the venous line 104 can be quite short as compared to conventional blood treatment systems. For example, in some embodiments, the arterial line 102 and the venous line 104 have a length less than one meter (e.g., less than 90 cm, less than 80 cm, less than 70 cm, less than 60 cm, less than 50 cm, less than 40 cm, less than 30 cm, or less than 20 cm).

In some embodiments, the treatment module 220 and/or the arm 280 can include one or more sensors 226 that output signals that can indicate the position, orientation, and/or motion of the treatment module 220 relative to the blood treatment machine console 210. For example, in some cases sensors such as accelerometers (e.g., 3D accelerometers), gyroscopic sensors, ultrasonic sensors, proximity sensors, optical sensors, magnetometers, global positioning sensors, radio triangulation sensors (e.g., like in keyless access systems for cars or based on WiFi, Bluetooth or similar technologies), electronic spirit levels, electric spirit levels, and/or the like, within the treatment module 220 and/or the arm 280 may be utilized to indicate the position, orientation, and/or motion of the treatment module 220 relative to the blood treatment machine console 210.

In some embodiments, the signal output(s) from such sensors 226 can be used by the control system of the blood treatment system 1 as input(s), for example, to activate or deactivate certain modes of operation of the blood treatment system 1 or, alternatively, to determine the current situation of the treatment module 220. For example, a certain orientation of the treatment module 220 might be used to indicate that a maintenance mode should be activated. Pulling the treatment module 220 forward, towards the patient, might initiate preparations for a treatment mode. Another particular orientation of the treatment module 220 might be defined as indicative for activating a deaeration mode. Pushing back the treatment module 220 toward the blood treatment machine console 210 might act as input for pausing operation of the blood treatment system 1, and so on. Other modes of operation of the blood treatment system 1 that can be activated in response to a particular position, orientation, or motion of the treatment module can include, but are not limited to, a "nurse mode," a debugging mode, and a filling or priming mode, to provide a few examples. Including the one or more sensors 226 that output signals that can indicate the position, orientation, and/or motion of the treatment module 220 relative to the blood treatment machine console 210 allows user control interactions with the blood treatment system 1, conveniently and intuitively, by the manual handling of the arm-mounted treatment module 220. The electronics and/or controls that receive and interpret output signals from the sensors 226 can be located in the blood treatment machine console 210, the treatment module 220, the arm 280, and/or elsewhere. In some embodiments, the raw data from one or more sensors 226 is/are processed in a separate step to generate the sensor output that is used in further steps. In some embodiments, the processor carrying out this processing step is located in the treatment module 220. In some embodiments, the processor carrying out this processing step is located in the arm 280. In some embodiments, the processor carrying out this processing step is located in the blood treatment machine console 210.

In some embodiments, there are additionally or alternatively sensors located in the arm 280 to determine the position and/or orientation of the treatment module 220. Such sensors can be angle sensors, path sensors, range sensors, and/or other types of sensors. In some embodiments, such sensors can be used to recognize if a situation of mechanical shock has occurred, such as in case of a mechanical impact of a person or an object making contact with the treatment module 220. The detection of the impact event can be used to identify alarms as false alarms, when they occur at the same time in other sensors triggered by the impact event. For example, an ultrasonic air bubble detector could produce sensor readings causing an alarm in case of an impact event. The accelerometer or position sensor(s) in the treatment module 220 and/or arm 280 could enable detecting an impact event that occurred at the time of that alarm. In this case, the treatment module controls could deescalate that alarm taking into account the air bubble detector readings would likely have been be falsified due to the detected impact event.

Further advantages of the using such sensors as described above include, in combination with a de-aeration mode or priming mode, utilizing the sensor readout for initiating a certain operating state to reduce the work load for personnel handling the a treatment module 220. Additionally, the haptic input channel would allow for a more intuitive way of handling the treatment module 220. Further, these concepts can help avoid errors and mistakes in handling and treatments, and false alarms can be identified.

In some embodiments, the output signal(s) from the sensor(s) 226 may be guided to a control unit in the treatment module 220, and/or the console 210, and the control unit may be configured or programmed to disable or enable predefined processes of the blood treatment system 1 on the basis of the signal(s). In some embodiments, the priming phase of the dialyzer 100 (which means filling the dialyzer 100 with liquid and de-aerating the dialyzer 100) and/or the treatment phase of the blood treatment system 1 is only enabled when the signal indicates a vertical position of the dialyzer 100. In some embodiments, the signal(s) from the sensor(s) 226 must indicate that treatment module 220 is in an angled position in relation to the ground (level in relation to the earth), so that any liquid that could flow out of the liquid circuit is not dropping to the earth but conducted along the surface of the treatment module 220 and may be guided into a liquid collection port of the treatment module 220. The liquid collection port may by a rail along the lower end of the treatment module 220 and being connected to a container to collect leaking liquid.

The control unit may further be connected to a user interface, such as the user interface 212. The user interface may be a graphical user interface and optical light system, a sound generating system, or any combination thereof. The user interface may be configured to display the orientation of the treatment module 220 (as provided by the signal(s) from the sensor(s) 226) and the display may change in visible appearance as a function of the enabled processes.

In one example embodiment, the graphical user interface will show the orientation of the treatment module 220 when the next process step is, for example, the priming phase. Only if the treatment module 220 is in the upright position 220 (as detected by the signal(s) from the sensor(s) 226) will the orientation be displayed in green and the operator will be able to manually initiate the priming phase via user interface actions (e.g., speech, button, gesture, etc.), or the system will automatically initiate the next process step.

Although the illustrated example includes a treatment module 220 that is moveable relative to the base console 210, it should be understood that some other examples do not include a separately positionable treatment module 220. In such examples, the base console 210 may incorporate the features described with respect to the illustrated treatment module 220 other than those specific to the positionability.

The blood treatment machine console 210 includes a user interface 212, a control system, facilities for making dialysate, and the like.

In the blood treatment system 1, much of the componentry associated with conventional systems is incorporated into the dialyzer 100 and portions of the blood treatment module 220 that interfaces with the dialyzer 100. Conventional blood treatment systems generally include a disposable tubing set and/or cassette (in addition to a dialyzer). Such a tubing set and/or cassette is used to interface with one or more hardware items such as pumps, sensors, valve actuators, and the like. However, the dialyzer 100 and the blood treatment machine 200 integrate multiple functionalities in a highly consolidated fashion (as described further below).

Figure 2:
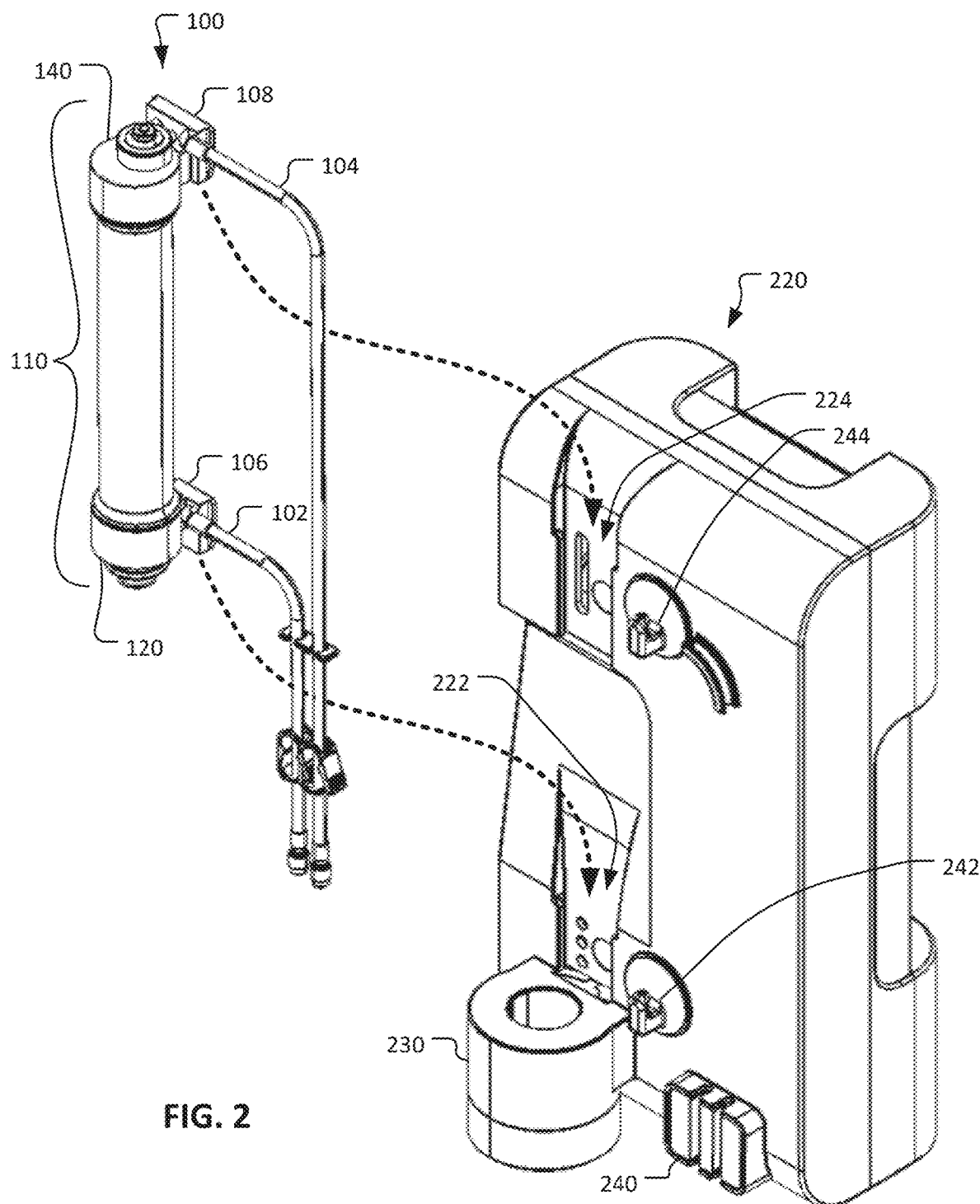
FIG. 2 is an exploded perspective view of a dialyzer and treatment module system of the blood treatment system of FIG. 1.
Figure 3:
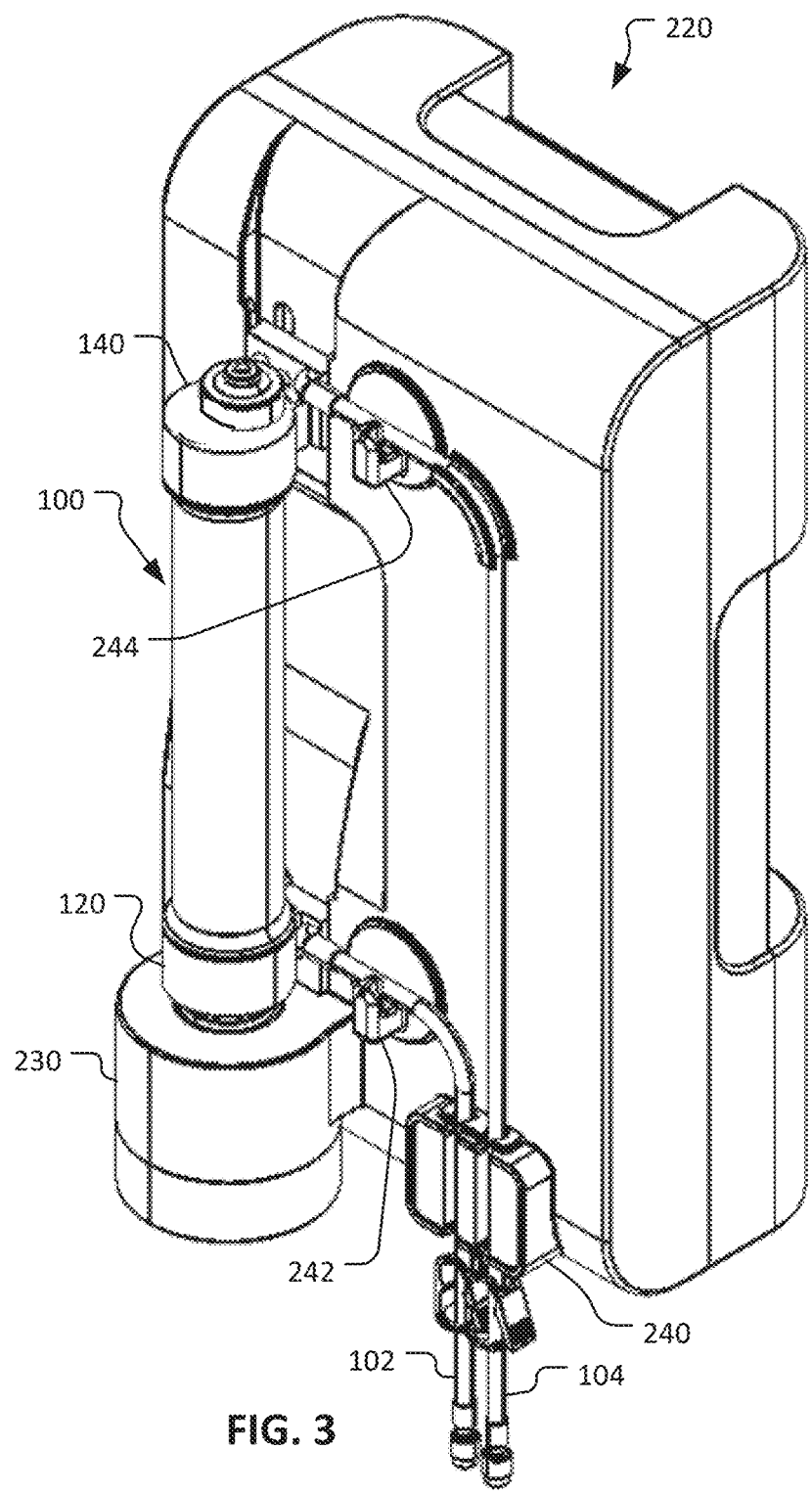
FIG. 3 is a perspective view of the dialyzer and the treatment module system of FIG. 2 in an assembled configuration.

Referring also to FIGS. 2 and 3, the dialyzer 100 is releasably coupleable to the treatment module 220 in a convenient manner. For example, in the depicted embodiment, the dialyzer 100 is slidably coupleable with the treatment module 220. Accordingly, the dialyzer 100 and treatment module 220 include complementary structural features to facilitate slidable coupling. That is, the dialyzer 100 includes a first projection 106 that is slidably coupleable with a first complementarily shaped slot 222 of the treatment module 220, and the dialyzer 100 includes a second projection 108 that is slidably coupleable with a second complementarily shaped slot 224 of the treatment module 220. In some embodiments, other means of releasably connecting the dialyzer 100 to the treatment module 220 can be used. For example, in some embodiments a connection style such as a snap-in connection, a thumb screw connection, a clamp connection, a suction connection, and the like can be used.

The dialyzer 100 includes a housing 110 that defines an interior space. A bundle of hollow fiber semi-permeable membranes (or simply "hollow fibers") are disposed within the interior of the housing 110. The arterial line 102 and the venous line 104 each extend from the housing 110 (e.g., from opposite ends of the housing 110) and are in fluid communication with the interior of the housing 110, and with lumens of the hollow fibers.

The housing 110 includes a first end cap 120 and a second end cap 140. The first end cap 120 includes the first projection 106 and the second end cap 140 includes the second projection 108. Moreover, the arterial line 102 is coupled to the first end cap 120 and the venous line 104 is coupled to the second end cap 140.

The treatment module 220 includes a pump drive unit 230 that is configured to releasably receive a portion of the first end cap 120. As described further below, the pump drive unit 230 generates dynamic magnetic fields to levitate and rotate a pump rotor that is housed within the portion of the first end cap 120. In some embodiments, the pump drive unit 230 includes no moving parts.

The pump rotor is configured such that rotation of the pump rotor forces blood of the patient 10 through the lumens of the hollow fibers of the dialyzer 100 in the direction from the first end cap 120 toward the second end cap 140. Accordingly, blood from the patient 10 flows into the dialyzer 100 via the arterial line 102, flows through the lumens of the hollow fibers, and flows out of the dialyzer 100 via the venous line 104.

The treatment module 220 also includes other devices that interface with the arterial line 102 and/or the venous line 104. For example, the depicted treatment module 220 includes a tubing interface module 240 configured to releasably receive a portion of the arterial line 102 and/or a portion of the venous line 104. The tubing interface module 240 can include devices that can perform functions such as flow rate detection, gaseous bubble detection, and the like. That is, the tubing interface module 240 can include sensors for detecting one or more parameters such as a flow rate of the blood within the arterial line 102 and/or the venous line 104, hematocrit (Hct) and other blood properties, and/or for detecting gaseous bubbles (e.g., air bubbles) in the blood within the arterial line 102 and/or the venous line 104. In some embodiments, the flow rate detection and/or the bubble detection are performed using sensors such as ultrasonic sensors, optical sensors, or other suitable types of sensors. In other embodiments, sensors for detecting gaseous bubbles can be located at or in an end cap of the disposable of the dialyzer 100.

The treatment module 220 also includes an arterial line clamp 242 and a venous line clamp 244. The clamps 242 and 244 are used to either fully restrict or fully un-restrict (e.g., in an on/off valve fashion) the flow of blood within the arterial line 102 and/or the venous line 104, respectively.

The treatment module 220 also includes devices for interfacing with the dialyzer 100 to measure pressure at particular locations within the dialyzer 100, as described further below. Additionally, as described further below, the treatment module 220 includes conduits that can selectively interface with the dialyzer 100 to facilitate flow of liquids such as substituate and/or dialysate between the dialyzer 100 and the treatment module 220.

Figure 4:
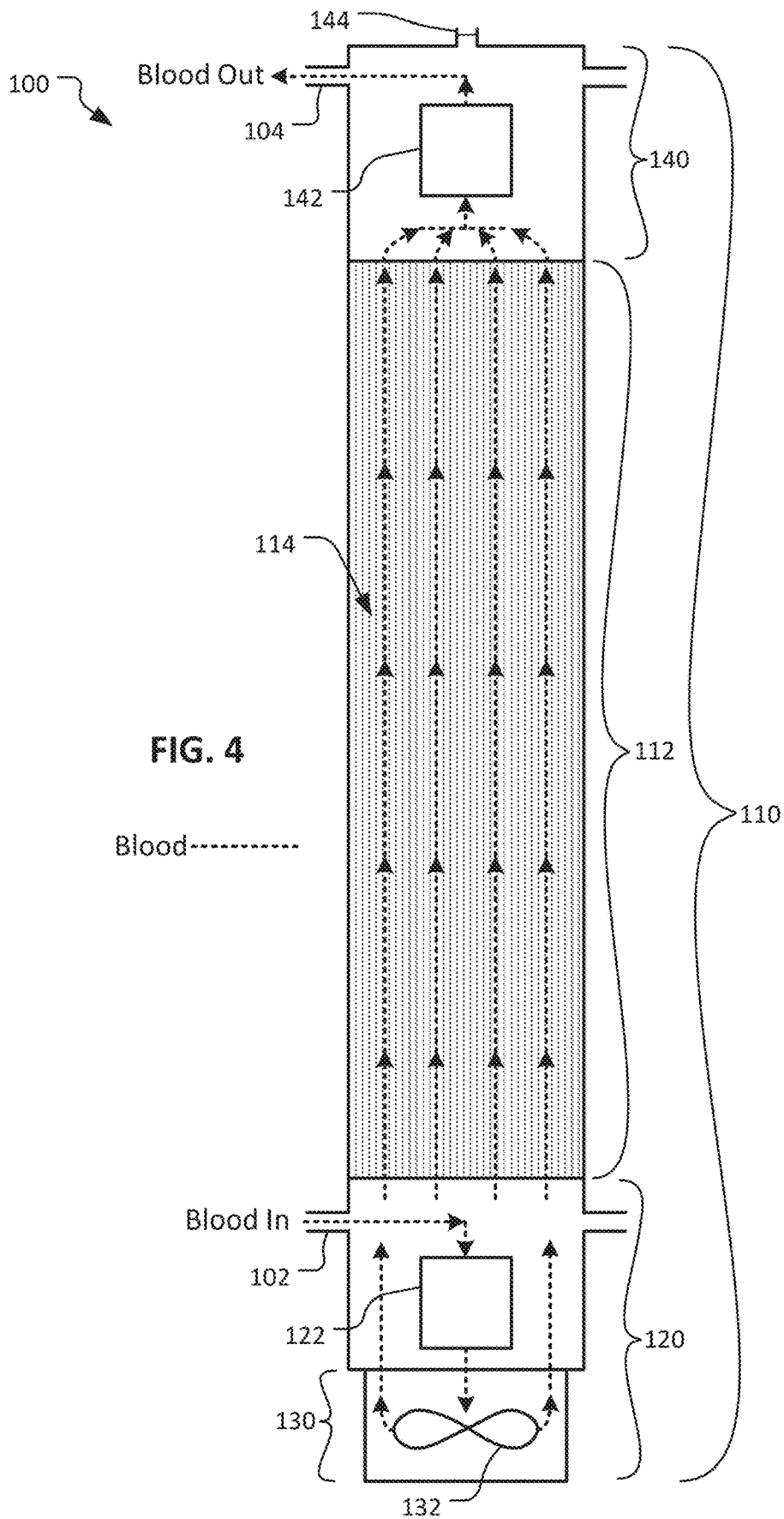
FIG. 4 is a schematic depiction of the dialyzer of the blood treatment system of FIG. 1, showing the blood flow path through the dialyzer.
Figure 5:
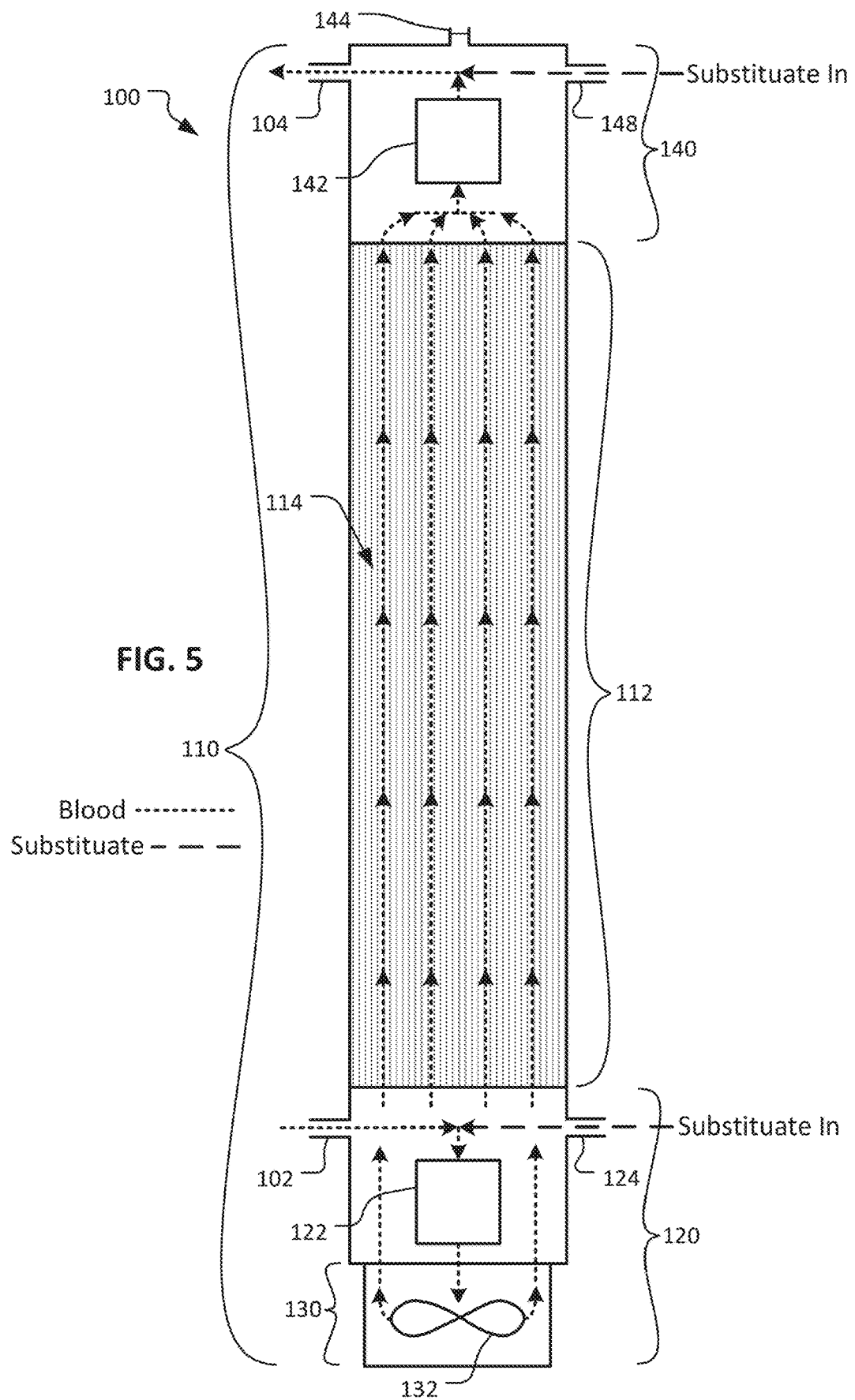
FIG. 5 is another schematic depiction of the dialyzer of the blood treatment system of FIG. 1, showing the blood flow path through the dialyzer and substitute addition locations.
Figure 6:
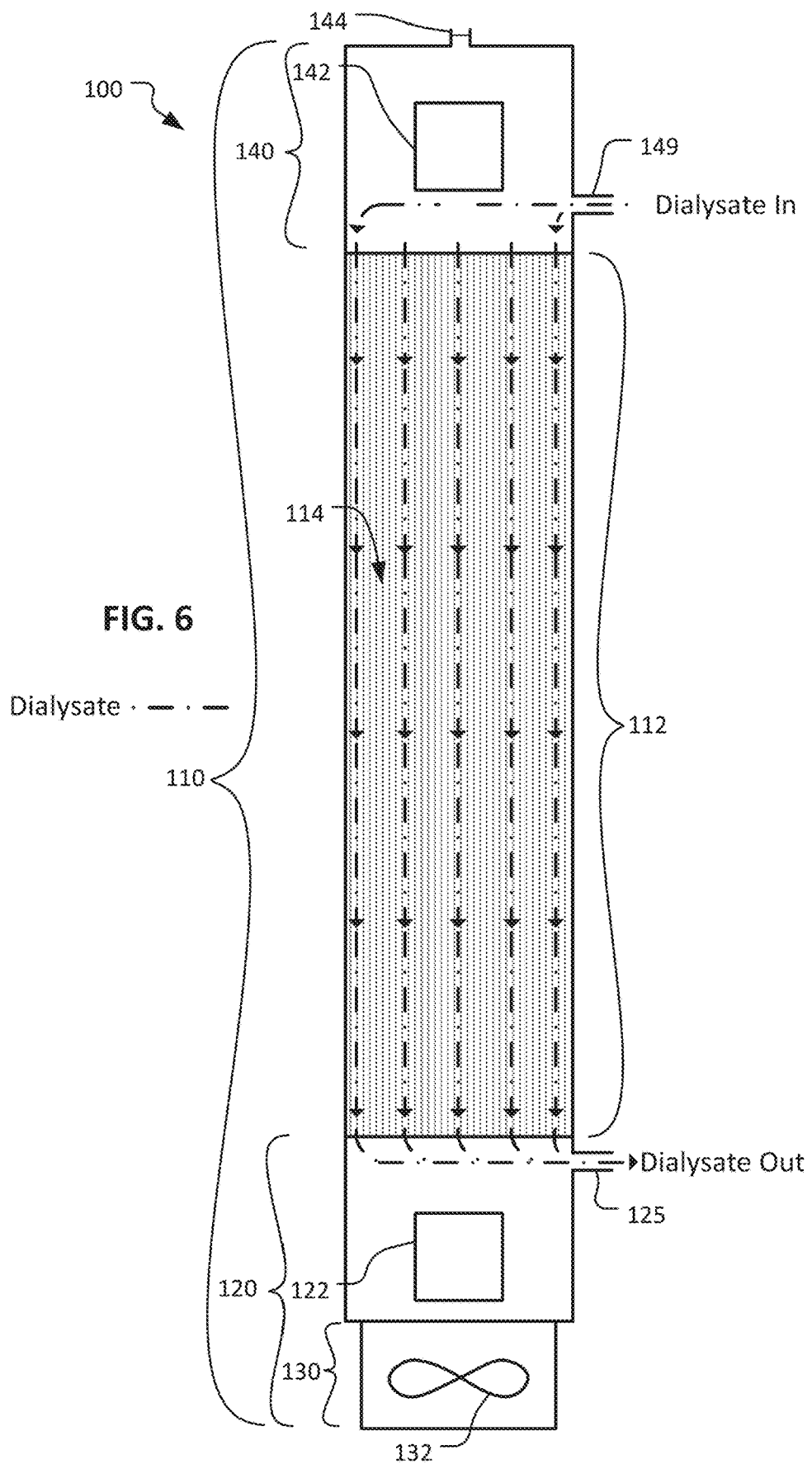
FIG. 6 is another schematic depiction of the dialyzer of the blood treatment system of FIG. 1, showing the dialysate flow path through the dialyzer.
Figure 7:
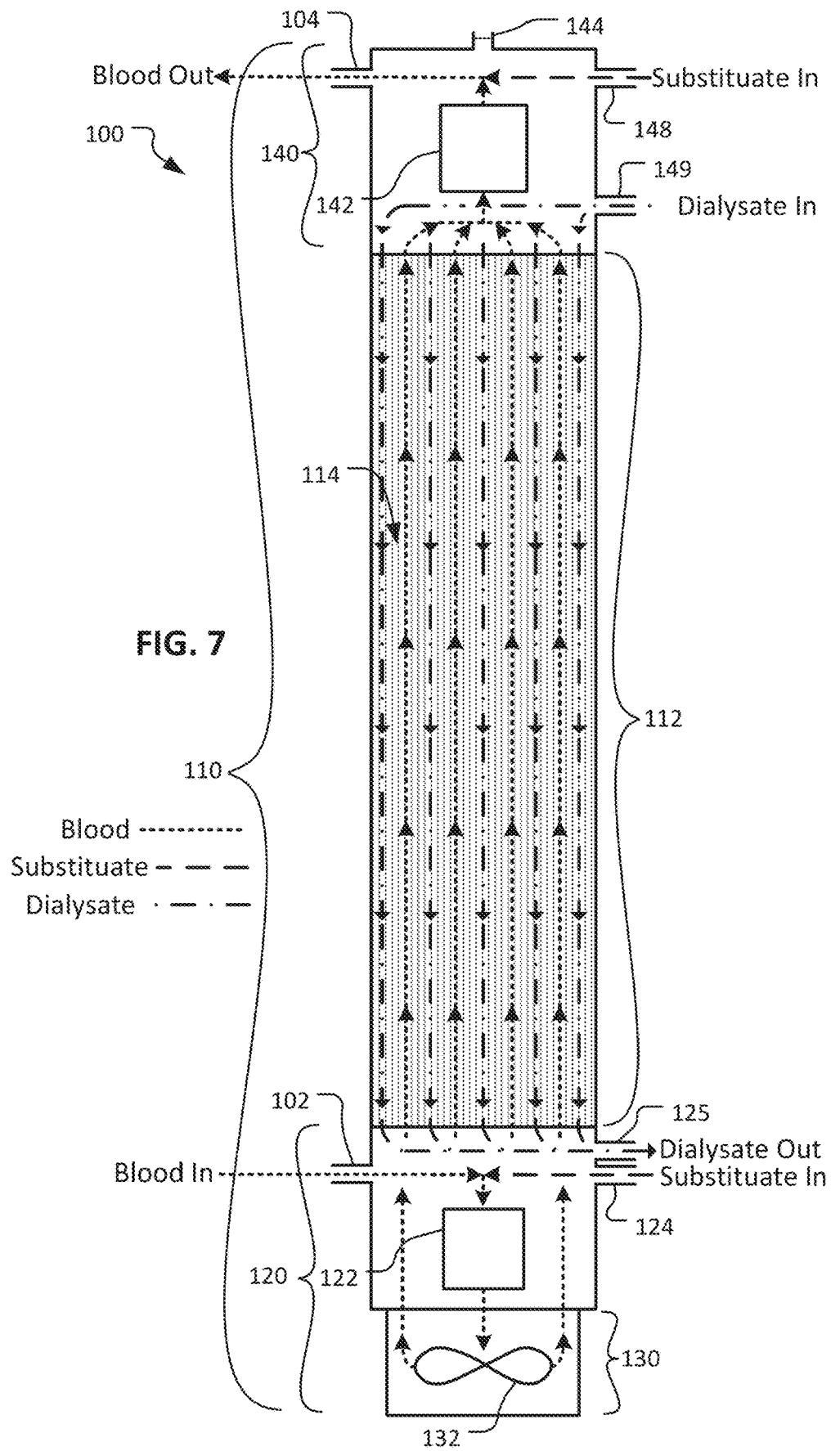
FIG. 7 is another schematic depiction of the dialyzer of the blood treatment system of FIG. 1, showing the blood and dialysate flow paths and the substitute addition locations.

FIGS. 4-7 are schematic diagrams of the dialyzer 100. For ease of understanding, FIG. 4 depicts exclusively the flow of blood through the dialyzer 100; FIG. 5 depicts the flow of blood and substituate; FIG. 6 depicts exclusively the flow of dialysate; and FIG. 7 depicts the flow of blood, substituate, and dialysate.

FIGS. 4-7 are simplified to show general flow relationships in the dialyzer 100. For example, the first potting 115 and the second potting 116, which secure the two respective ends of each of the fibers of the bundle of hollow fibers 114, are omitted to simplify the illustration. In addition to securing the bundle of hollow fibers, these pottings 115 and 116, maintain a barrier between the blood and the dialysate. The pottings 115 and 116 and the associated flow routing are described in further detail below in connection with FIGS. 8 to 29.

Referring to FIG. 4, the housing 110 of the dialyzer 100 includes the first end cap 120, the second end cap 140, and a middle housing portion 112 that extends between the first end cap 120 and the second end cap 140. The middle housing portion 112 contains the majority of the length of the bundle of hollow fibers 114. As indicated above, a more-detailed description of the construction of the dialyzer 100, including the bundle of hollow fibers 114 is provided below in connection with the description of FIGS. 8 to 29.

The first end cap 120 includes a pump housing 130. A rotatable centrifugal pump rotor 132 is located within the pump housing 130. The pump rotor 132 is enclosed or encased within the pump housing 130. Accordingly, the pump rotor 132 is contained at a fixed position relative to the bundle of hollow fibers 114.

In accordance with some embodiments, the pump rotor 132 is a radially pumping pump wheel with a hollow central volume. The blades (or vanes) of the pump wheel of the pump rotor 132 are arranged so that they project or extend at least partially radially. In some cases, the blades are arranged to project or extend entirely radially. In some cases, the blades are arranged to project or extend partially radially and partially tangentially.

As described further herein, the pump rotor 132 is operated and controlled by interfacing with the pump drive unit 230 (shown in FIGS. 2 and 3) of the treatment module 220. That is, the pump rotor 132 can be levitated and rotated by magnetic fields that are caused to emanate from the pump drive unit 230 during use.

The housing 110 defines one or more pressure detection chambers. The depicted embodiment includes an arterial pressure detection chamber 122 and a venous pressure detection chamber 142. The arterial pressure detection chamber 122 is located prior to the pump rotor 132. That is, the arterial pressure detection chamber 122 is arranged to facilitate measuring pre-pump arterial pressure. Additionally or alternatively, in some embodiments, pressure can be measured post-pump (but prior to the hollow fibers 114). As described further below, the pressure detection chambers 122 and 142 are each configured to interface with a respective pressure transducer of the treatment module 220.

The flow path of blood through the dialyzer 100 will now be explained in reference to the dashed lines shown in FIG. 4. Blood flows into the first end cap 120 via the arterial line 102 (shown in FIGS. 2 and 3). The fluid flow path entering the first end cap 120 is transverse to a longitudinal axis of the dialyzer 100. The arterial pressure detection chamber 122 is located along the flow path after entering the first end cap 120 but prior to the pump rotor 132. The blood flow path transitions to parallel to the longitudinal axis of the dialyzer 100 to deliver the blood to the pump rotor 132. The blood is directed to a center of the pump rotor 132. Rotations of the centrifugal pump rotor 132 force the blood radially outward from the pump rotor 132. Then, after flowing radially outward from the pump rotor 132, the blood turns and flows longitudinally toward the middle housing portion 112. The blood enters the lumens of the bundle of hollow fibers 114 and continues flowing longitudinally toward the second end cap 140. After passing through the middle housing portion 112, the blood exits the bundle of hollow fibers 114, enters the second end cap 140, and flows transversely out of the second end cap 140 via the venous line 104. The venous pressure detection chamber 142 is located along the blood flow path in the second end cap 140. In some embodiments, a one-way check valve is located along the blood flow path as the blood exits the second end cap 140 into the venous line 104. In some embodiments, a one-way check valve is included on side-arm connections to the blood flow pathway to prevent back-fluid flow or blood entering the side arm connection.

The second end cap 140 can also be configured to deaerate the blood as it enters and flows through the second end cap 140. Accordingly, the second end cap 140 includes an air purge member 144 that allows air and other gases to exit the second end cap 140 while preventing fluids such as blood from exiting therethrough. The air purge member 144 can also be used as an access port. That is, the air purge member 144 can be configured for uses such as sample extraction and administration of medicaments (e.g., heparin). The air purge member 144 can comprise a plastic tube extending from the second end cap 140. An elastomeric seal member located within the plastic tube is configured to open when a syringe without a needle is coupled with the air purge member 144.

Again, blood passing through the dialyzer 100 for its purification and treatment flows through the lumens of the hollow fibers 114 (while dialysate flows through the dialyzer 100 over/along the outsides of the hollow fibers 114 in the spaces between the outsides of the hollow fibers 114, as described further herein). This is in direct contrast to how blood flows through extracorporeal blood oxygenator devices (which also use hollow fibers made of a permeable material). Extracorporeal blood oxygenators are used to perform treatments such as extracorporeal membrane oxygenation ("ECMO") and, in conjunction with a heart-lung machine, for surgical procedures such as coronary artery bypass grafting ("CABG"), heart valve replacement/repair, heart transplant, and the like. While extracorporeal blood oxygenators, like the dialyzer 100, can include a bundle of hollow fibers made of a permeable material, blood passing through the extracorporeal blood oxygenators flows over/along the outsides of the hollow fibers (as opposed to through the lumens of the hollow fibers as is the case for the dialyzer 100), and gases flow through the lumens of the hollow fibers.

Accordingly, because of the fundamentally differing types of blood flow paths of the dialyzer 100 in comparison to an extracorporeal blood oxygenator, there is a significant difference between the pressure and flow parameters of blood passing through the dialyzer 100 in comparison to blood passing through an extracorporeal blood oxygenator. Table 1 below shows some blood pressure and flow parameters for Dialysis (using a dialyzer) and for Extracorporeal Oxygenation (using an extracorporeal blood oxygenator).

TABLE 1

| Parameter | Dialysis | Extracorporeal Oxygenation |
|---|---|---|
| Flow Rate | 300 mL/min (typical) | 1000 to 5000 mL/min (typical) |
| | 650 mL/min (maximum) | 10000 mL/min (maximum) |
| Pressure | 500 mmHg (667 mbar) to 1500 mmHg (2000 mbar) (typical) | 500 mmHg (667 mbar) (typical) |
| Example Pressure at Flow Rate | 700 mmHg (933 mbar) at 300 mL/min | 250 mmHg (333 mbar) at 1000 mL/min |
| Example Ratio of Pressure to Flow Rate ("Hemolysis Risk Factor") | 933 mbar/300 mL/min = 3.11 | 333 mbar/1000 mL/min = 0.33 |

The ratio of the pressure to the flow rate that is associated with blood flowing through a dialyzer or an extracorporeal oxygenator can also be termed as the "hemolysis risk factor." The risk of causing hemolysis (damage to red blood cells) tends to increase as the pressure to flow rate ratio is increased. Accordingly, the term "hemolysis risk factor" quantifies a useful parameter associated with the physical construction and usage of dialyzer and extracorporeal oxygenator devices.

From Table 1, it can be observed that blood experiences a much higher hemolysis risk factor (the ratio of pressure to flow rate during usage) using the dialyzer 100, for example, than during extracorporeal oxygenation. For example, in the example of Table 1, the hemolysis risk factor is 3.11 for dialysis and 0.33 for extracorporeal oxygenation. That is approximately a 10 to 1 difference. In other words, the ratio of pressure to flow rate, or the hemolysis risk factor, is approximately 10 times greater during dialysis than during extracorporeal oxygenation. This comparison is one way to illustrate and understand the substantial physical differences between dialyzers (such as the dialyzer 100, for example) and extracorporeal oxygenator devices.

Referring to FIG. 5, the dialyzer 100 is also configured to receive one or more additions of substitute fluid that are combined with the blood within the dialyzer 100. For example, in the depicted embodiment, the first end cap 120 defines a first substitute liquid port 124 and the second end cap 140 defines a second substitute liquid port 148. The first substitute liquid port 124 is in direct fluid communication with the incoming blood flow path defined by the first end cap 120, and is confluent therewith prior to the arterial pressure detection chamber 122. Alternatively, in some embodiments substitute fluid can be added to the blood after exiting the pump housing 130 (i.e., after being pressurized by the pump rotor 132) but prior to entering the lumens of the hollow fibers 114. The second substitute liquid port 148 is in direct fluid communication with the outgoing blood flow path defined by the second end cap 140, and is confluent therewith after the venous pressure detection chamber 142. Each of the substitute liquid ports 124 and 148 can include a respective one-way check valve therein that prevents liquid from exiting the end caps 120 and 140 via the substitute liquid ports 124 and 148.

Referring to FIG. 6, the dialyzer 100 is also configured to receive dialysate, and to direct the dialysate to flow through the housing 110. For example, in the depicted embodiment, the second end cap 140 defines a dialysate inlet port 149 and the first end cap 120 defines a dialysate outlet port 125. The dialysate flows into the second end cap 140 via the dialysate inlet port 149, and then enters the middle housing portion 112 containing the bundle of hollow fibers 114. The dialysate flows through the middle housing portion 112 via the spaces defined between the outer diameters of the fibers of the bundle of hollow fibers 114. In other words, while the blood flows within the lumens of the fibers of the bundle of hollow fibers 114, the dialysate liquid flows along the outsides of the fibers. The semi-permeable walls of the fibers of the bundle of hollow fibers 114 separate the dialysate liquid from the blood. The dialysate liquid flows out of the middle housing portion 112 and into the first end cap 120. The dialysate liquid exits the first end cap 120 via the dialysate outlet port 125.

Referring to FIG. 7, the flow paths of blood, substitute, and dialysate (as each are described in reference to FIGS. 4-6 above) are now shown in combination (e.g., as would occur during use of the dialyzer 100). When substitute is added, the substitute is combined directly with the blood in the end cap(s) 120 and/or 140. In contrast, the dialyzer 100 keeps the dialysate separated from the blood. However, waste products from the blood (e.g., urea, creatinine, potassium, and extra fluid) are transferred by osmosis from the blood to the dialysate through the semi-permeable walls of the fibers of the bundle of hollow fibers 114 in the dialyzer 100.

Figure 10:
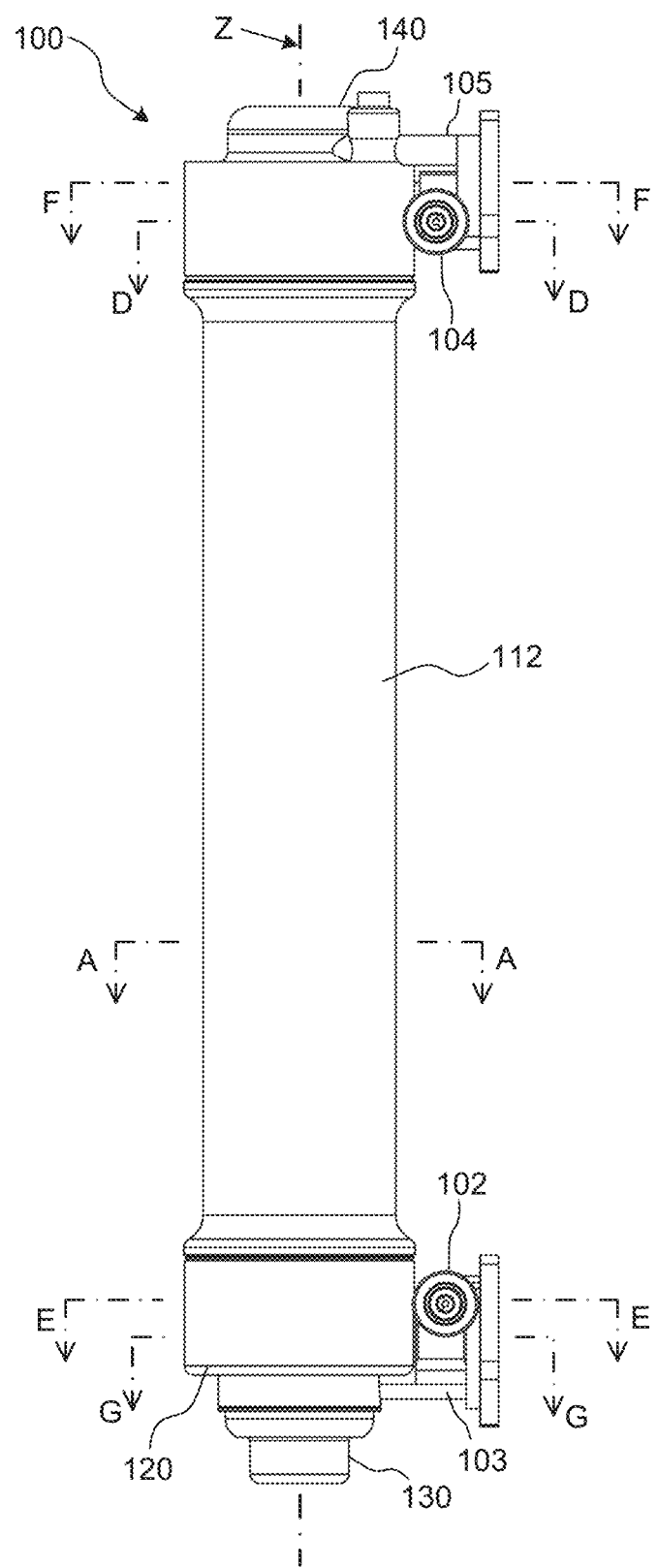
FIG. 10 is a side view of the dialyzer of the blood treatment system of FIG. 1 with the arterial and venous lines shown in section.
Figure 11:
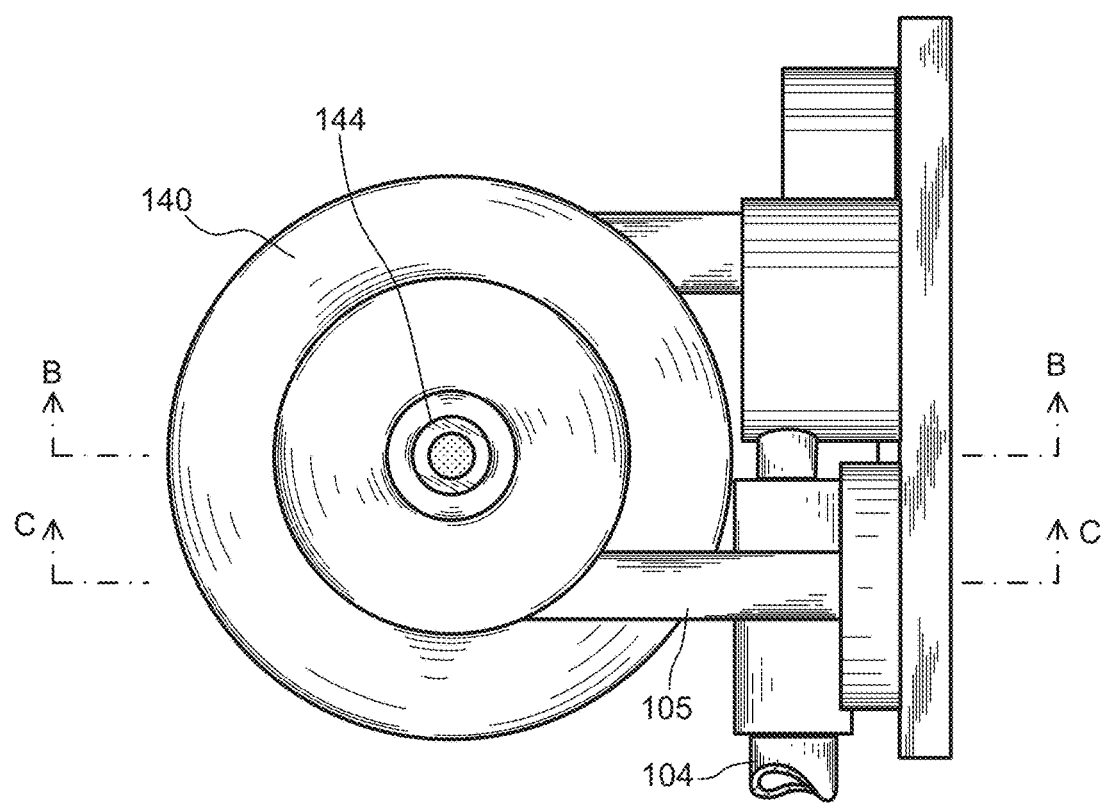
FIG. 11 is a top view of the dialyzer of the blood treatment system of FIG. 1 with the arterial and venous lines shown in section.
Figure 12:
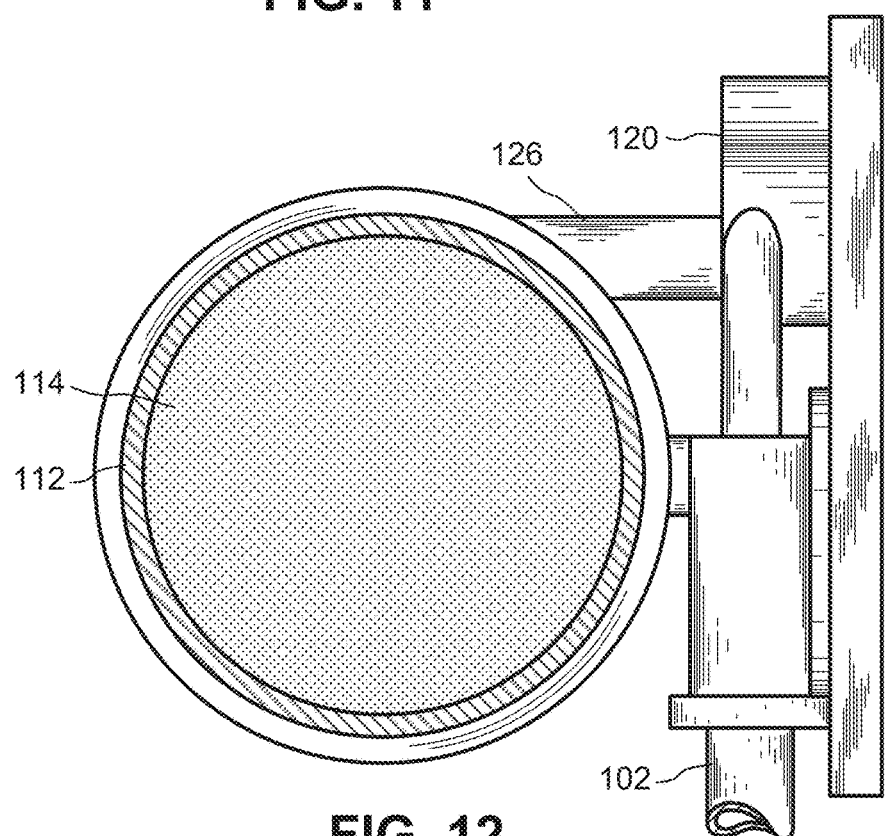
FIG. 12 is a cross-sectional view of the dialyzer of the blood treatment system of FIG. 1 taken along section line A-A of FIG. 10.

Referring to FIGS. 8-10, the description of the structure and function of the dialyzer 100 provided above in the context of the schematic diagrams of FIGS. 4-7 can be used to promote an understanding of the structure and function of the actual embodiment of the dialyzer 100 shown here. The dialyzer 100 includes the housing 110 comprising the first end cap 120, the middle housing portion 112 containing the bundle of hollow fibers 114, and the second end cap 140. The arterial line 102 is connected to the first end cap 120. The venous line 104 is connected to the second end cap 140. In this example, the arterial line 102 and the venous line 104 are permanently bonded (e.g., solvent bonded, laser welded, etc.) to the first end cap 120 and the second end cap 140, respectively. It should be understood, however, that in other examples, one or both of these connections may utilize any other suitable permanent or removable fluid-tight connection, including, for example, press fits and latchable connectors.

The first end cap 120 includes the pump housing 130, the first substitute liquid port 124, and the dialysate outlet port 125. The first end cap 120 also includes the arterial pressure detection chamber 122. The exterior wall of the arterial pressure detection chamber 122 (as visible in the rear view of FIG. 8) comprises a flexible membrane 160. As described further herein (e.g., in reference to FIGS. 31-33), a pressure transducer of the treatment module 220 (e.g., FIGS. 1-3 and 30) interfaces with (e.g., abuts against) the flexible membrane 160 of the arterial pressure detection chamber 122 while the dialyzer 100 is operational with the treatment module 220.

The second end cap 140 includes the second substitute liquid port 148, the dialysate inlet port 149, and venous pressure detection chamber 142. The exterior wall of the venous pressure detection chamber 142 (as visible in the rear view of FIG. 8) comprises a flexible membrane 162. As described further herein (e.g., in reference to FIGS. 31-33), a pressure transducer of the treatment module 220 (e.g., FIGS. 1-3 and 30) interfaces with (e.g., abuts against) the flexible membrane 162 of the venous pressure detection chamber 142 while the dialyzer 100 is operational with the treatment module 220. The air purge member 144 is also attached to the second end cap 140 and is in fluid communication with the interior of the second end cap 140.

Figure 20:
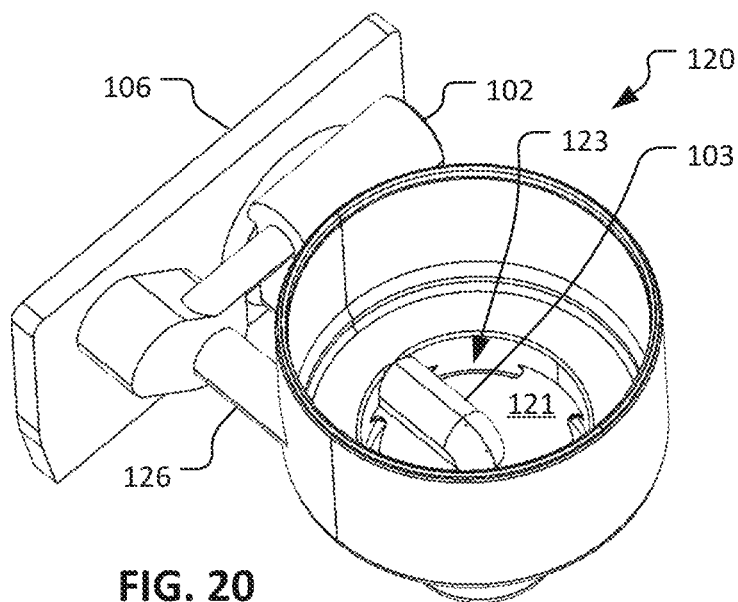
FIG. 20 is a perspective view of a first end cap of the dialyzer of the blood treatment system of FIG. 1.
Figure 21:
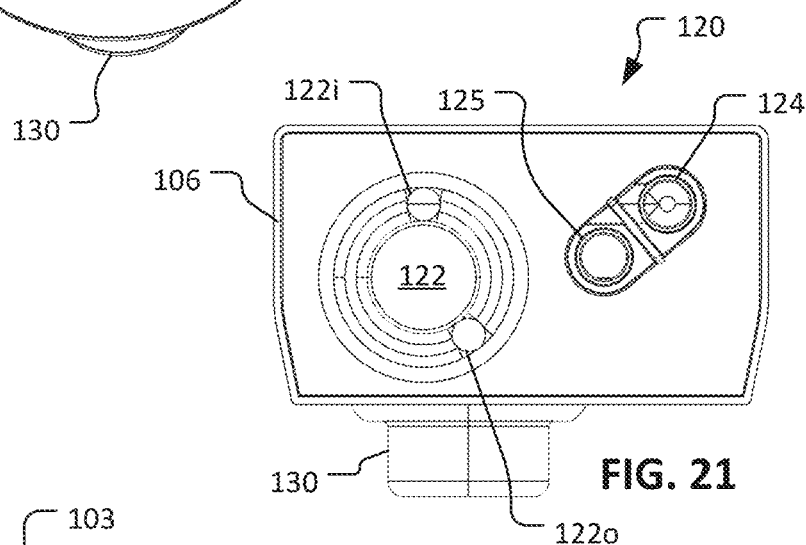
FIG. 21 is a rear view of the first end cap of FIG. 20.
Figure 22:
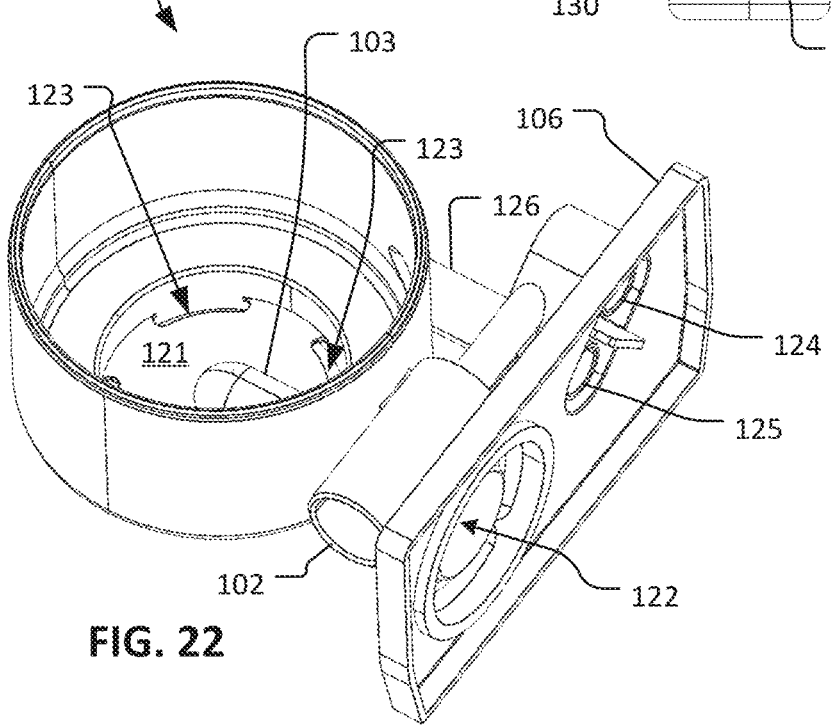
FIG. 22 is another perspective view of the first end cap of FIG. 20.

Referring to FIGS. 20-22, here the first end cap 120 is shown in isolation from other portions of the dialyzer 100 so that structural details of the first end cap 120 are visible in greater detail. In FIGS. 21 and 22, the arterial flexible membrane 160 is not shown in order to facilitate illustration of other features of the arterial pressure detection chamber 122. Referring also to the cross-sectional view of FIG. 16, blood to be treated in the dialyzer 100 flows into the first end cap 120 via the arterial line 102. The blood enters an arterial mixing chamber 163, from which the blood then flows into the arterial pressure detection chamber 122. The blood can either pass through the arterial mixing chamber 122 undiluted or be mixed with substitute fluid, such as, for example, when the blood treatment system 1 is operating in a pre-dilution HDF mode.

In situations (e.g., pre-dilution HDF) where substitute is added to the arterial mixing chamber, the substitute flows into the first end cap 120 from a first substitute supply conduit 254 via the first substitute liquid port 124. The substitute then flows through an arterial substitute supply tube 165. The substitute then passes through a check valve 167 and into the arterial mixing chamber 163. This flow of substitute is illustrated via the series of arrows in FIG. 16 extending from the first substitute liquid inlet port 124 to the outlet of the check valve 167. In the arterial mixing chamber 163, the substitute mixes with the incoming arterial blood flow (illustrated by an upwardly pointing arrow) before passing through an arterial pressure detection chamber inlet 122i. The check valve 167 prevents the flow of blood into the arterial substituate supply tube 165 and the first substituate liquid inlet port 124. This prevents blood contamination of the first substituate supply conduit 254.

The blood (either undiluted or diluted with substituate, depending on the mode of operation of the treatment system 1) flows through the arterial pressure detection chamber inlet 122i and into the arterial pressure detection chamber 122. The flow of the blood through the arterial pressure detection chamber 122 allows an arterial pressure transducer 250 (illustrated in FIGS. 31-33) of the blood treatment module 200 to measure the arterial blood pressure via membrane 160. The blood exits the arterial pressure detection chamber 122 via an arterial pressure detection chamber outlet 122o, as illustrated by the arrows in FIG. 13. After exiting the arterial pressure detection chamber 122, the blood then flows through a rotor supply tube 103 toward the pump housing 130. The rotor supply tube 103 defines a fluid flow path that is transverse to the longitudinal axis Z of the dialyzer 100.

Figure 16:
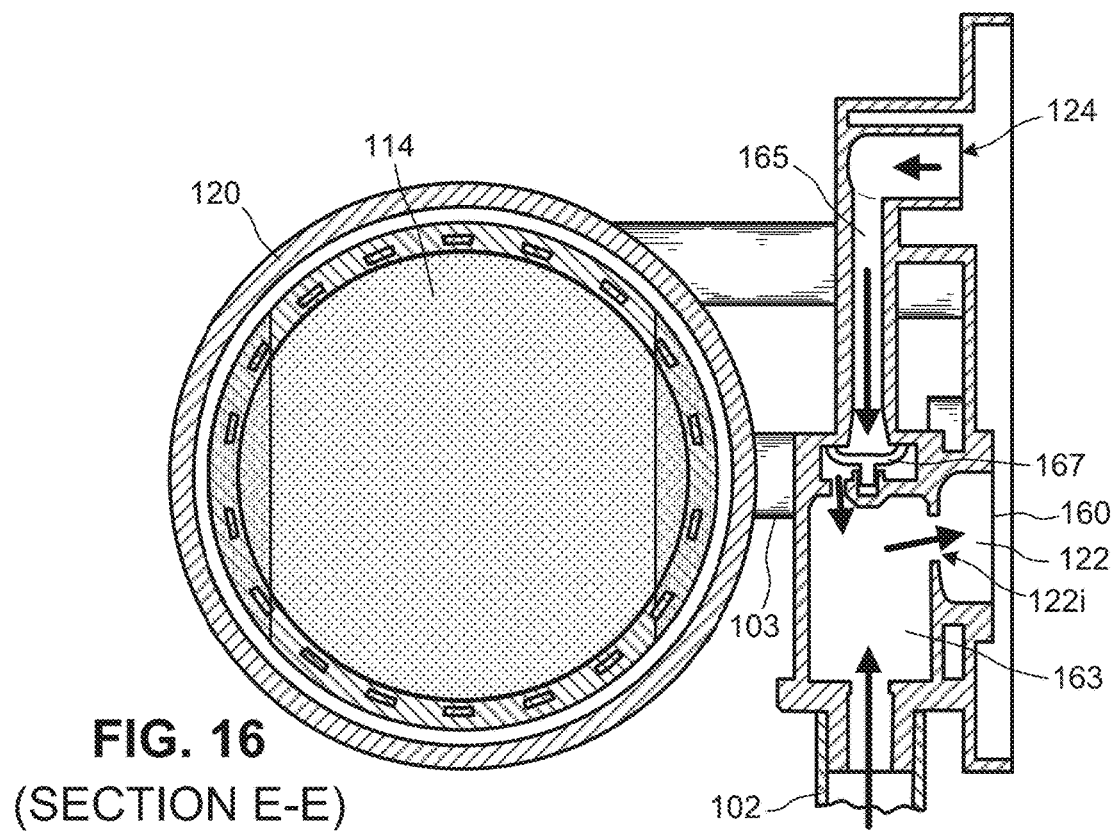
FIG. 16 is a cross-sectional view of the dialyzer of the blood treatment system of FIG. 1 taken along section line E-E of FIG. 10.

The first end cap 120 also includes the dialysate outlet port 125. The dialysate flows from a peripheral inner wall area of the first end cap 120 through a dialysate outlet tube 126 to the dialysate outlet port 125. As illustrated in FIG. 16, a one-way flow valve 16 (e.g., check valve) can be included in the first substituate liquid port 124 and the arterial line 102.

Figure 13:
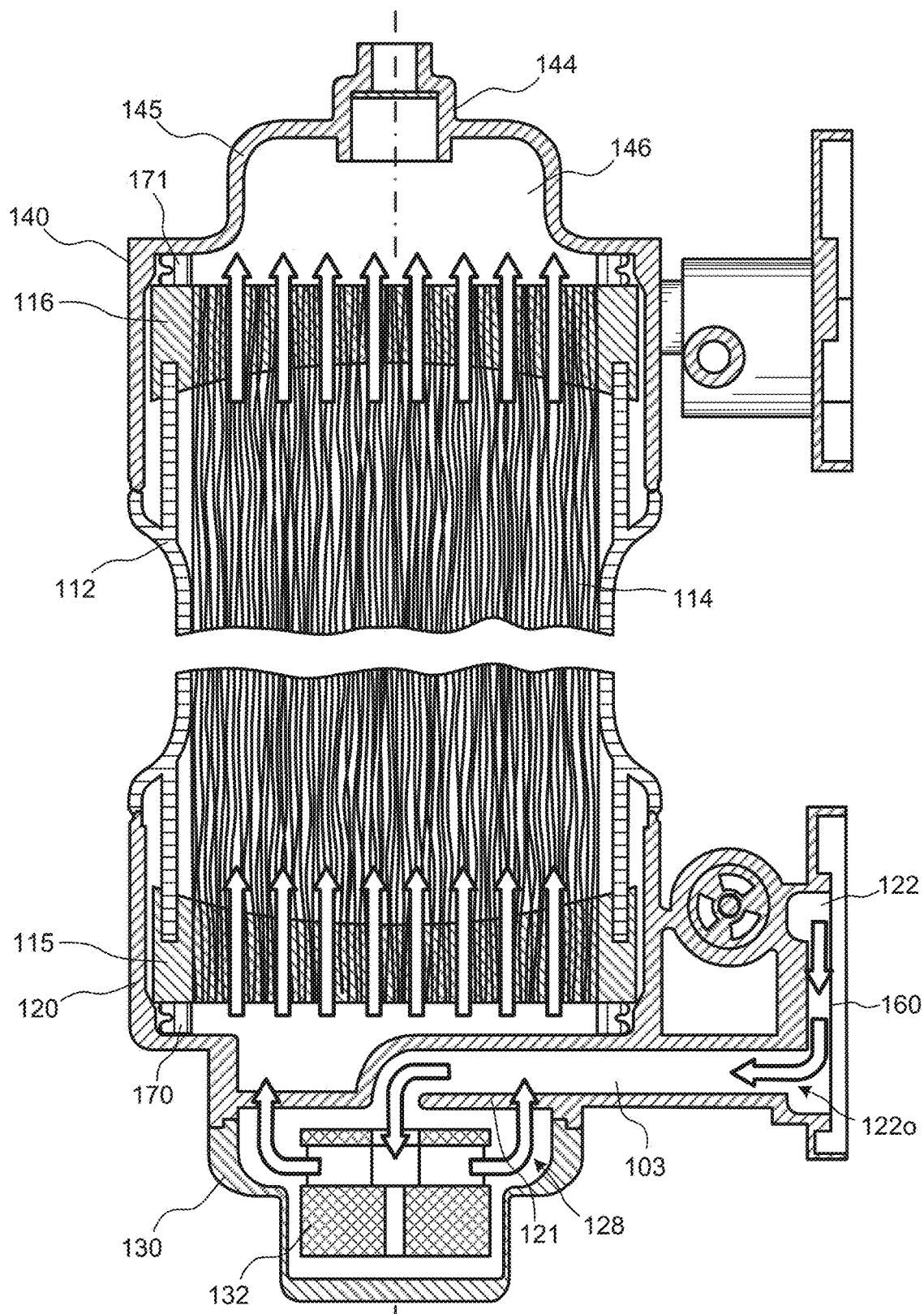
FIG. 13 is a broken cross-sectional view of the dialyzer of the blood treatment system of FIG. 1 taken along section line B-B of FIG. 11.
Figure 23:
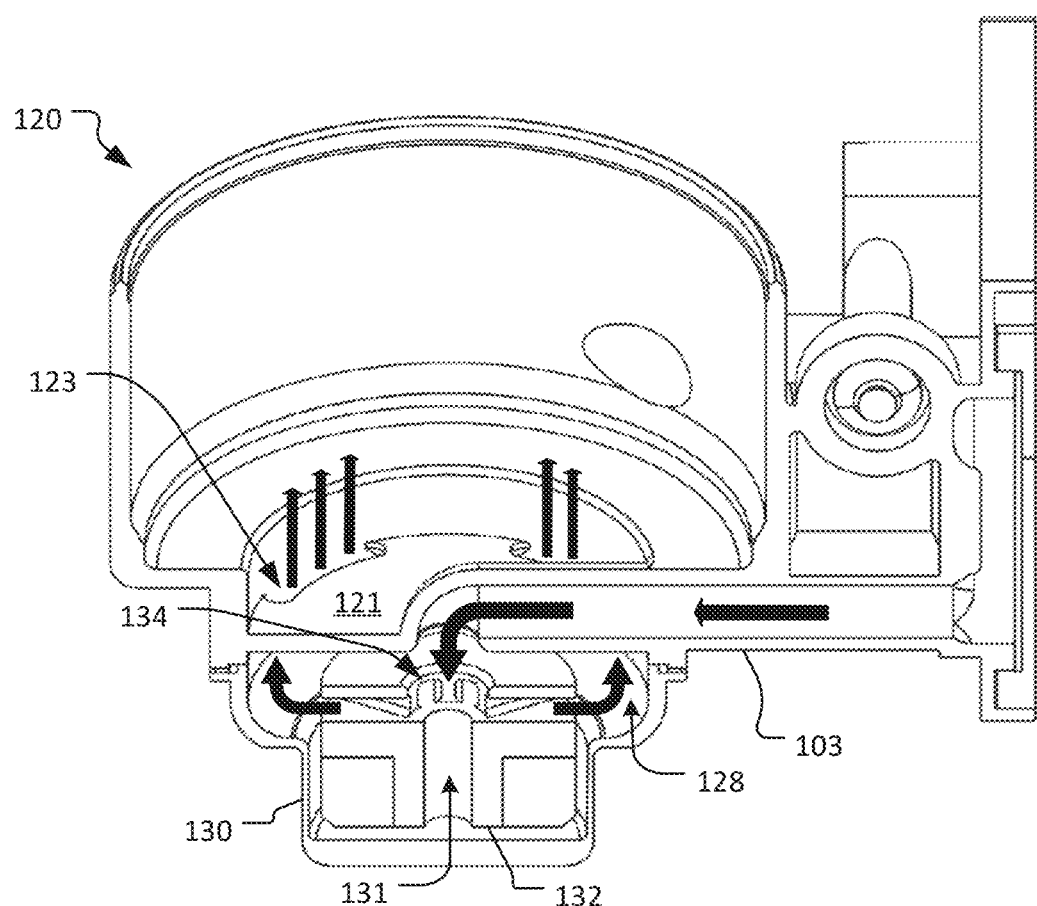
FIG. 23 is a perspective view of the first end cap of FIG. 20 shown in a partial longitudinal cross-sectional view and depicting blood flow therethrough.

Referring to FIGS. 13 and 23, the flow path of the blood (which, as indicated above, may be undiluted or diluted with substituate) through the first end cap 120 can be visualized to a greater extent in the longitudinal cross sectional view of the dialyzer 100 of FIG. 13 and the partial longitudinal cross-sectional perspective view of the first end cap 120 in FIG. 23. The blood flows toward the pump housing 130 through the rotor supply tube 103. A 90° elbow at the end of the rotor supply tube 103 directs the blood to turn and flow parallel along the longitudinal central axis Z of the dialyzer 100 at the center of the first end cap 120. From the exit of the rotor supply tube 103, the blood is delivered to a center of a pump rotor 132 located within the pump housing 130.

Figure 24:
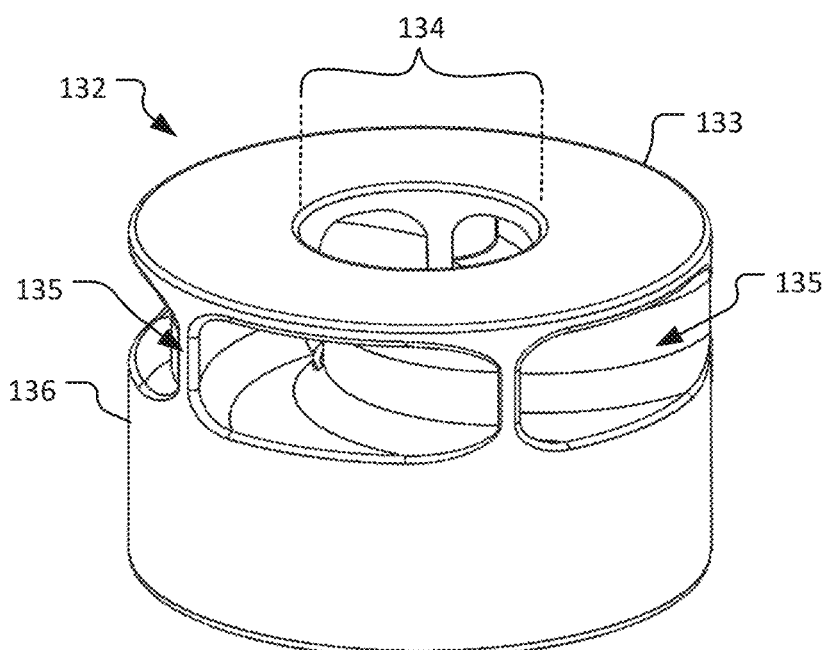
FIG. 24 is a perspective view of a pump rotor that is configured to be located in the first end cap of FIG. 20.

Referring also to FIG. 24, the example pump rotor 132 includes a first plate 133, a magnetic disc 136, and a plurality of vanes 135 (or blades) extending between the first plate 133 and the magnetic disc 136. In accordance with some embodiments, the pump rotor 132 is a pump impeller comprising a radially pumping pump wheel with a hollow central volume. Accordingly, the depicted pump rotor 132 can also be referred to a pump impeller. The blades (or vanes) of the pump wheel of the pump rotor 132 can be arranged so that they project or extend at least partially radially. In some cases, the blades are arranged to project or extend entirely radially. In some cases, the blades are arranged to project or extend partially radially and partially tangentially.

The first plate 133 is an annular ring that defines a central aperture 134. In some embodiments, the first plate 133 is omitted and the vanes 135 extend from the magnetic disc 136 and terminate without the first plate 133. The magnetic disc 136 defines a central lumen 131 (FIG. 23) that extends along the longitudinal central axis Z of the dialyzer 100. The magnetic disc 136 can include an un-encapsulated or an encapsulated bi-pole magnet (e.g., a rare earth magnet, a ferrite ceramic magnet, and other suitable types of magnets). In the depicted embodiment, the vanes 135 are arcuate members.

Rotation of the pump rotor 132 causes blood to flow as depicted by the large arrows of FIGS. 13 and 23. In some embodiments, the pump rotor 132 is driven during operation to rotate at a speed (revolutions per minute) in a range of 5,000 rpm to 25,000 rpm, or 5,000 rpm to 22,000 rpm, or 7,000 rpm to 20,000 rpm, or 9,000 rpm to 18,000 rpm, or 11,000 rpm to 16,000 rpm, or 12,000 rpm to 15,000 rpm, or 13,000 rpm to 14,000 rpm, without limitation.

In some embodiments, the height of the vanes 135 (measured along the longitudinal central axis Z) is in a range of 2 mm to 10 mm, or 2 mm to 8 mm, or 2 mm to 6 mm, or 3 mm to 5 mm, or 3 mm to 4 mm, without limitation.

In some embodiments, the diameter of the exit of the rotor supply tube 103 is in a range of 5 mm to 10 mm, or 6 mm to 9 mm, or 7 mm to 8 mm, without limitation. In some embodiments, the diameter of the central aperture 134 of the pump rotor 132 is in a range of 4 mm to 12 mm, or 5 mm to 11 mm, or 6 mm to 10 mm, or 7 mm to 9 mm. In some embodiments, the diameter of the central lumen 131 is in a range of 2 mm to 10 mm, or 3 mm to 9 mm, or 4 mm to 8 mm, or 5 mm to 7 mm, without limitation. Accordingly, in some embodiments the diameter of the central aperture 134 of the pump rotor 132 is larger than, equal to, or smaller than the diameter of the exit of the rotor supply tube 103. Further, in some embodiments the diameter of the central lumen 131 of the pump rotor 132 is larger than, equal to, or smaller than the diameter of the exit of the rotor supply tube 103. Moreover, in some embodiments the diameter of the central aperture 134 of the pump rotor 132 is larger than, equal to, or smaller than the diameter of the exit of the rotor supply tube 103.

In some embodiments, during operation (e.g., while the pump rotor 132 is levitating) the clearance space between the top surface of the first plate 133 and the opposing lower surface of the internal support plate 121 is in a range of 1 mm to 3 mm, or 2 mm to 3 mm, or 1.5 mm to 2.5 mm, or 1 mm to 5 mm, without limitation. Similarly, in some embodiments, during operation (e.g., while the pump rotor 132 is levitating) 0the clearance space between the bottom of the magnetic disc 136 and the opposing surface of the pump housing 130 is in a range of 1 mm to 3 mm, or 2 mm to 3 mm, or 1.5 mm to 2.5 mm, or 1 mm to 5 mm, without limitation. In some embodiments, during operation the ratio of the clearance spaces between: (i) the top surface of the first plate 133 and the opposing lower surface of the internal support plate 121, in comparison to (ii) the bottom of the magnetic disc 136 and the opposing surface of the pump housing 130 is in a range of 1.1:1.0 to 1.2:1.0, or 0.8:1.0 to 1.0:1.0, or 1.0:1.0 to 1.3:1.0, or 0.9:1.0 to 1.1:1.0, without limitation.

In some embodiments, the outer diameter of the magnetic disc 136 is in a range of 15 mm to 25 mm, or 17 mm to 22 mm, or 18 mm to 20 mm, without limitation. In some embodiments, the inner diameter of the cylindrical inner wall of the pump housing 130 is in a range of 15 mm to 25 mm, or 17 mm to 23 mm, or 18 mm to 22 mm, or 19 mm to 21 mm, without limitation. Accordingly, in some embodiments the radially clearance space between the cylindrical outer wall of the pump rotor 132 and the cylindrical inner wall of the pump housing 130 is in a range of 0.3 mm to 1.1 mm, or 0.4 mm to 0.9 mm, or 0.5 mm to 0.8 mm, or 0.6 mm to 0.7 mm, without limitation.

The blood flows toward the pump rotor 132, passes through the central aperture 134, and is forced radially outward from the pump rotor 132 by the rotation of the vanes 135. Referring again to FIGS. 13 and 23, as the blood flows generally radially away from the pump rotor 132, the blood enters a toroidal space 128 defined by the pump housing 130 and/or the arterial end cap 120. Within the toroidal space 128, the blood is forced by the inner wall of the pump housing 130 to turn and flow parallel to the longitudinal axis Z of the dialyzer 100 toward the hollow fiber bundle 114.

In some embodiments, the diameter of the toroidal space 128 is larger than the diameter of the cylindrical inner wall of the pump housing 130 (which contains the magnetic disc 136) by a range of 10 mm to 17 mm, or 11 mm to 16 mm, or 12 mm to 15 mm, or 13 mm to 15 mm, or 14 mm to 15 mm, without limitation.

The first end cap 120 includes an internal support plate 121. The rotor supply tube 103 can be attached to and/or supported by the internal support plate 121. The internal support plate 121 is also attached to circumferential portions of an inner wall of the first end cap 120, while defining multiple openings (e.g., slots, circular openings, etc.) 123 therebetween. The openings/slots 123 provide passages for the blood to flow from the pump housing 130 toward the hollow fiber bundle. In the depicted embodiment, there are four arcuate slots 123 through which the blood can flow. In some embodiments, there is a single opening/slot 123, or two openings/slots 123, three openings/slots 123, four openings/slots 123, five openings/slots 123, six openings/slots 123, seven openings/slots 123, eight openings/slots 123, or more than eight openings/slots 123.

Due to the increased pressure created by the rotating pump rotor 132, the blood is pushed through the interior spaces (or lumens) of each of the hollow fibers of the bundle of hollow fibers 114. The blood enters the fibers via openings exposed on the surface of potting 115. Since the potting 115 is sealed against the arterial end cap 120, the pressurized blood is forced through the lumens of the hollow fibers of the bundle of hollow fibers 114, which pass through and are supported by the potting 115. In this example, the potting 115 is sealed against the arterial end cap 120 by a gasket 170, which is axially (i.e., in the direction of longitudinal axis Z) compressed between the outer periphery of the potting 115 and the interior wall of the arterial end cap 120. A second gasket 171 performs an analogous function with respect to the venous end cap 140 and potting 116.

As the blood flows axially through the lumens of the bundle of hollow fibers 114, dialysis takes place across the semipermeable fiber membranes with the dialysate flowing (in a counterflow direction) in the space surrounding the fibers 114. The blood then flows, still within the hollow fibers 114, through a second potting 116 in the venous end cap 140, and into an interior space 146 in the upper dome 145 of the venous end cap 140.

Again, while the dialyzer 100 is being used, dialysate flows from the venous end cap 140 to the arterial end cap 120 along the outer surfaces of the hollow fibers 114 such as within the spaces defined between the hollow fibers 114. If flow rate measurements of the dialysate were taken at various points along a radius of a cross-section transverse to the longitudinal axis Z, the measurements would show that in many cases the axial flow rate of the dialysate is not entirely uniform within the hollow fibers 114. That is, in many cases it would be seen that the flow rate of the dialysate is higher near the outer areas of the bundle of hollow fibers 114 than at the inner areas of the bundle of hollow fibers 114. In other words, there is a tendency for more dialysate to flow through the dialyzer 100 along the outer annular portions of the bundle of hollow fibers 114 than through the central portion of the bundle of hollow fibers 114.

The arterial end cap 120 is advantageously designed to direct blood to flow through the bundle of hollow fibers 114 in a manner that enhances dialysis efficiency in view of the non-uniform flow rate of the dialysate as described above. For example, the arterial end cap 120 includes the arcuate slots 123 through which blood is directed to flow in route to entering the bundle of hollow fibers 114. The radial locations of the arcuate slots 123 are biased toward outer annular portions of the bundle of hollow fibers 114 (as compared to the central portion of the bundle of hollow fibers 114). Accordingly, the arterial end cap 120 causes blood to flow through the outer annular portions of the bundle of hollow fibers 114 at a higher rate than the central portion of the bundle of hollow fibers 114 in a manner that advantageously matches the higher flow regions of the dialysate. This matching of the flow rate profiles of the blood and the dialysate is conducive to enhancing dialysis efficiency, as compared to having disparate flow rate profiles of the blood and dialysate.

The arterial end cap 120 is also advantageously designed to reduce the potential for blood hemolysis (damage to red blood cells). As described above, blood exiting the rotor 132 flows generally radially from the vanes 135 into the toroidal space 128. However, by virtue of the rotation of the rotor 132, the blood within the toroidal space 128 also has a tendency to flow substantially circularly (e.g., like a vortex). If the blood was forced to flow into the lumens of the hollow fibers 114 while still flowing in such a substantially circular manner, the resulting dynamic shear stresses would tend to cause hemolysis. Fortunately, the internal support plate 121 of the arterial end cap 120 is designed to reduce the circular flow of the blood, and thereby reduce the potential for hemolysis. For example, the arcuate slots 123, through which blood is directed to flow in route to entering the bundle of hollow fibers 114, reduce the circular flow of the blood. Instead, the arcuate slots 123 cause the blood to flow more axially toward the entries to the lumens of the hollow fibers 114. Accordingly, by reducing the circular flow of the blood as it enters the lumens of the hollow fibers 114, the arcuate slots 123 of the internal support plate 121 reduce the potential for dynamic shear stresses of the blood, and reduce the potential for hemolysis.

As described above, the pump rotor 132 defines the central lumen 131. The central lumen 131 extends through the pump rotor 132 from the area of the vanes 135 and all the way through the magnetic disc 136. In other words, the central lumen 131 provides for fluid communication between the area of the vanes 135 and the clearance spaces that exist between the cylindrical outer wall of the pump rotor 132 and the cylindrical inner wall of the pump housing 130. By virtue of the fluid communication provided by the central lumen 131, the potential for blood to become stagnant in areas within the pump housing 130 is mitigated. That is, the central lumen 131 helps to keep the blood that is in the clearance spaces between the cylindrical outer wall of the pump rotor 132 and the cylindrical inner wall of the pump housing 130 moving and flowing out therefrom. Accordingly, the potential for thrombosis in the pump housing 130 is reduced as a result of the central lumen 131 of the pump rotor 132.

Figure 25:
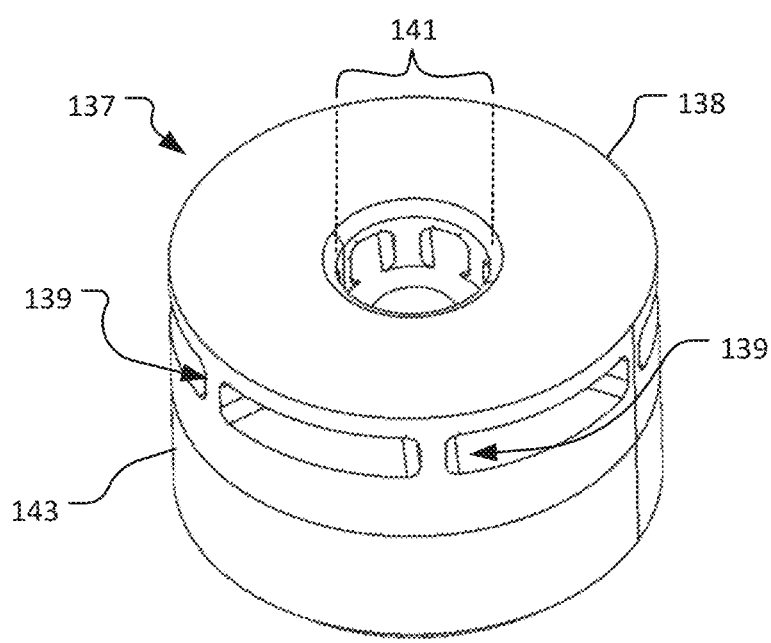
FIG. 25 is a perspective view of an alternative pump rotor that can be used in the first end cap of FIG. 20.
Figure 26:
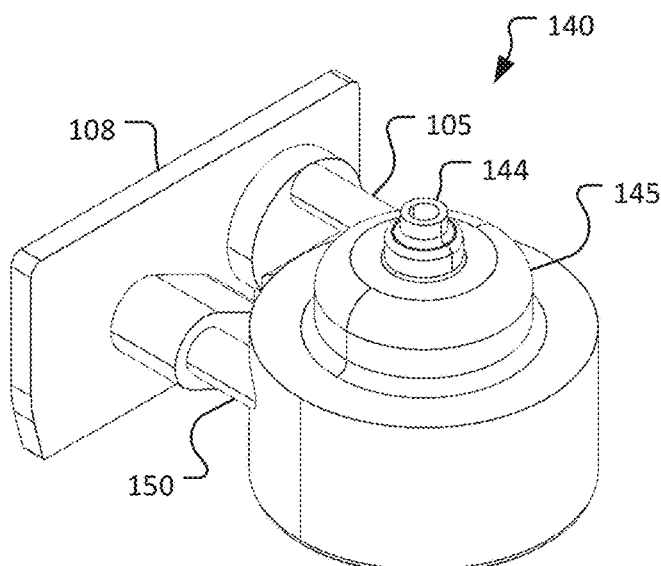
FIG. 26 is a perspective view of a second end cap of the dialyzer of the blood treatment system of FIG. 1.

Referring also to FIG. 25, an alternative pump rotor 137 includes a first plate 138, a magnetic disc 143, and a plurality of vanes 139 radially extending between the first plate 138 and the magnetic disc 143. The first plate 138 is annular and defines a central aperture 141. The magnetic disc 143 can include an un-encapsulated or an encapsulated bi-pole magnet (e.g., a rare earth magnet, a ferrite ceramic magnet, and other suitable types of magnets). In the depicted embodiment, the vanes 139 are linear members.

In accordance with some embodiments, the pump rotor 137 is a pump impeller comprising a radially pumping pump wheel with a hollow central volume. Accordingly, the depicted pump rotor 137 can also be referred to a pump impeller. The blades (or vanes) of the pump wheel of the pump rotor 137 can be arranged so that they project or extend at least partially radially. In some cases, the blades are arranged to project or extend entirely radially. In some cases, the blades are arranged to project or extend partially radially and partially tangentially.

The blood flows toward the pump rotor 137, passes through the central aperture 141, and is then forced radially outward from the pump rotor 137 by the rotation of the vanes 139. As the blood flows radially away from the pump rotor 137, the blood is forced by the inner wall of the pump housing 130 to turn and flow parallel to the longitudinal axis of the dialyzer 100 (toward the hollow fiber bundle). The blood then passes through the slots 123 defined between the internal support plate 121 and the inner wall of the first end cap 120. The slots 123 provide passages for the blood to flow from the pump housing 130 toward the hollow fiber bundle.

Figure 27:
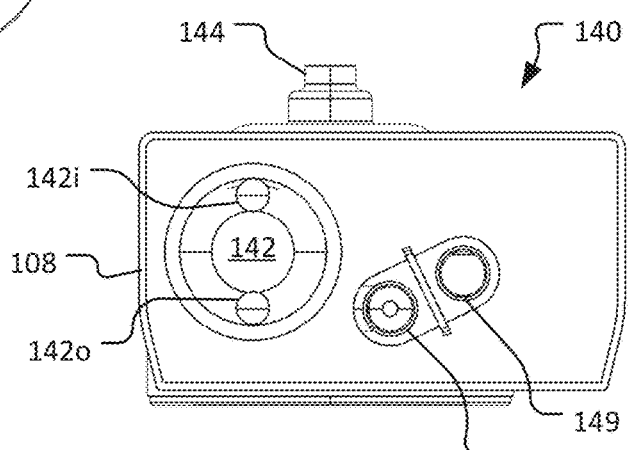
FIG. 27 is a rear view of the second end cap of FIG. 26.
Figure 28:
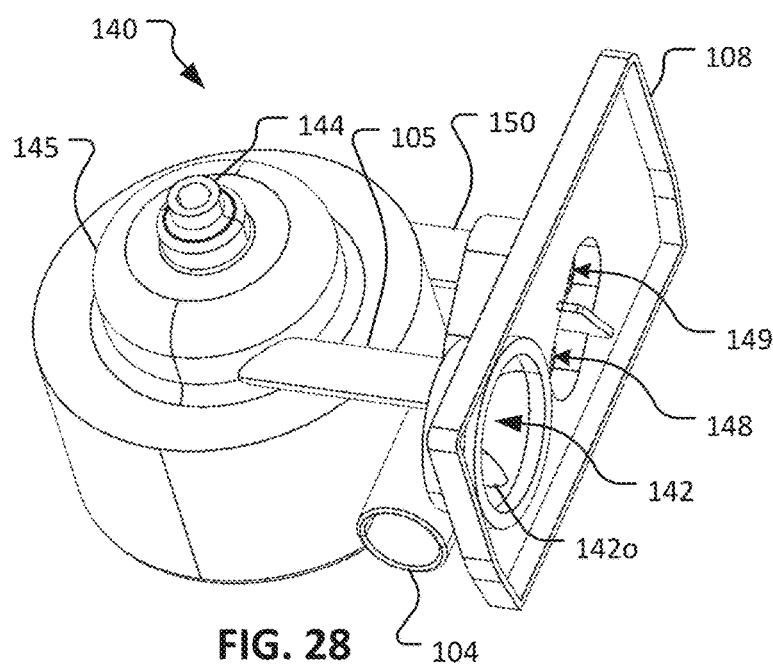
FIG. 28 is another perspective view of the second end cap of FIG. 26.
Figure 29:
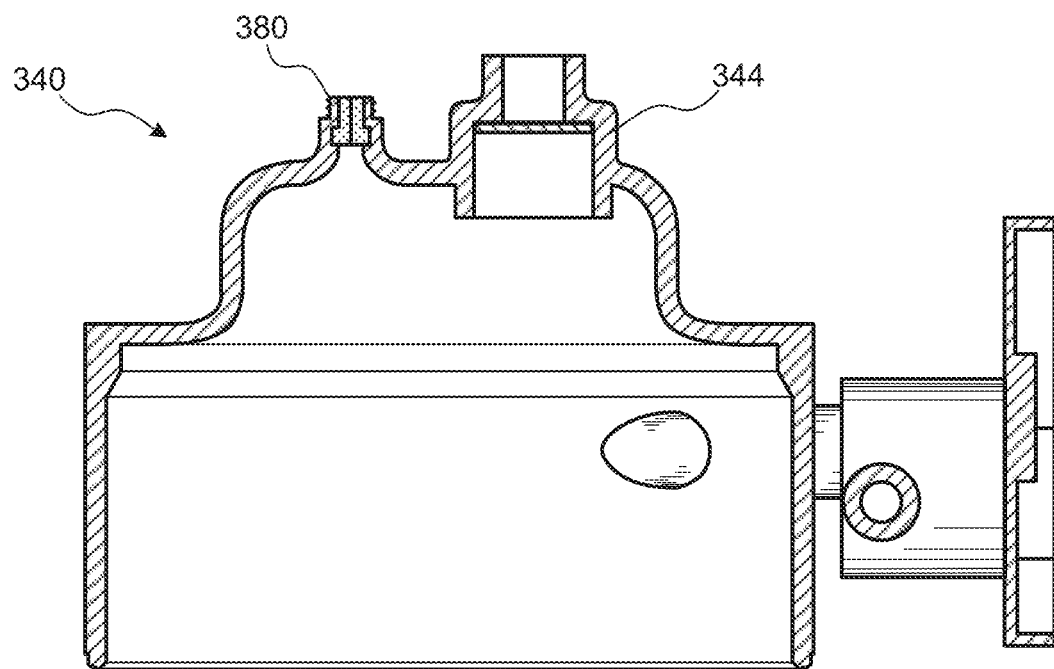
FIG. 29 is a cross-sectional view of an alternative second end cap.

Referring to FIGS. 27-29, here the venous end cap 140 (or "second end cap 140") is shown in isolation from other portions of the dialyzer 100 so that structural details of the second end cap 140 are visible in greater detail.

Figure 14:
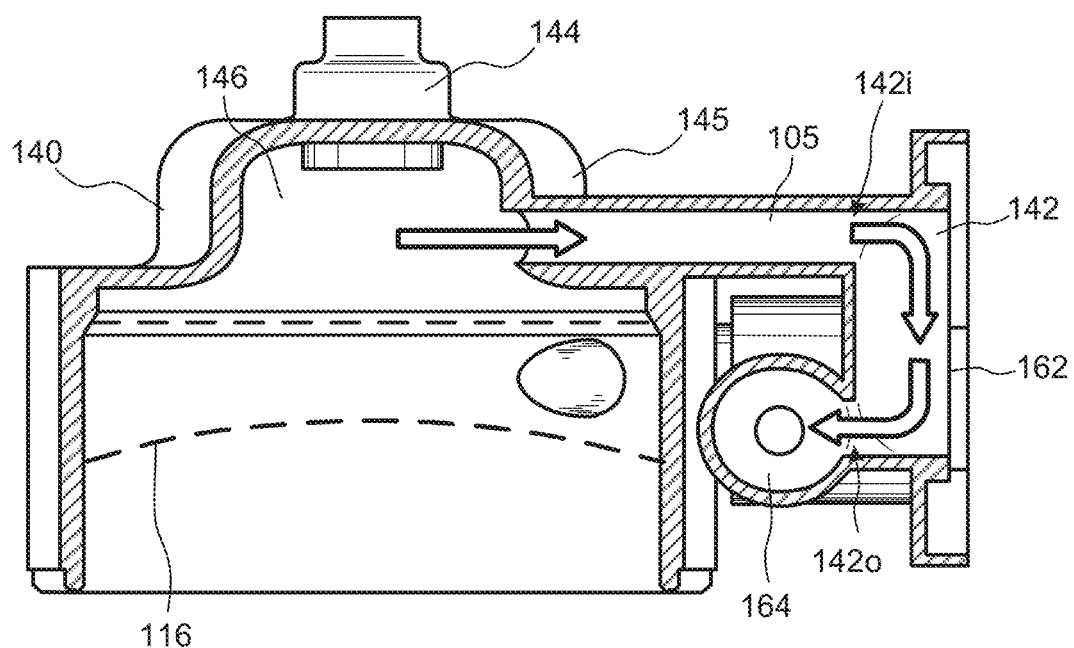
FIG. 14 is a cross-sectional view of the second end cap of the dialyzer of the blood treatment system of FIG. 1 taken along section line C-C of FIG. 11, with the position of a dialyzer potting shown in broken lines.
Figure 15:
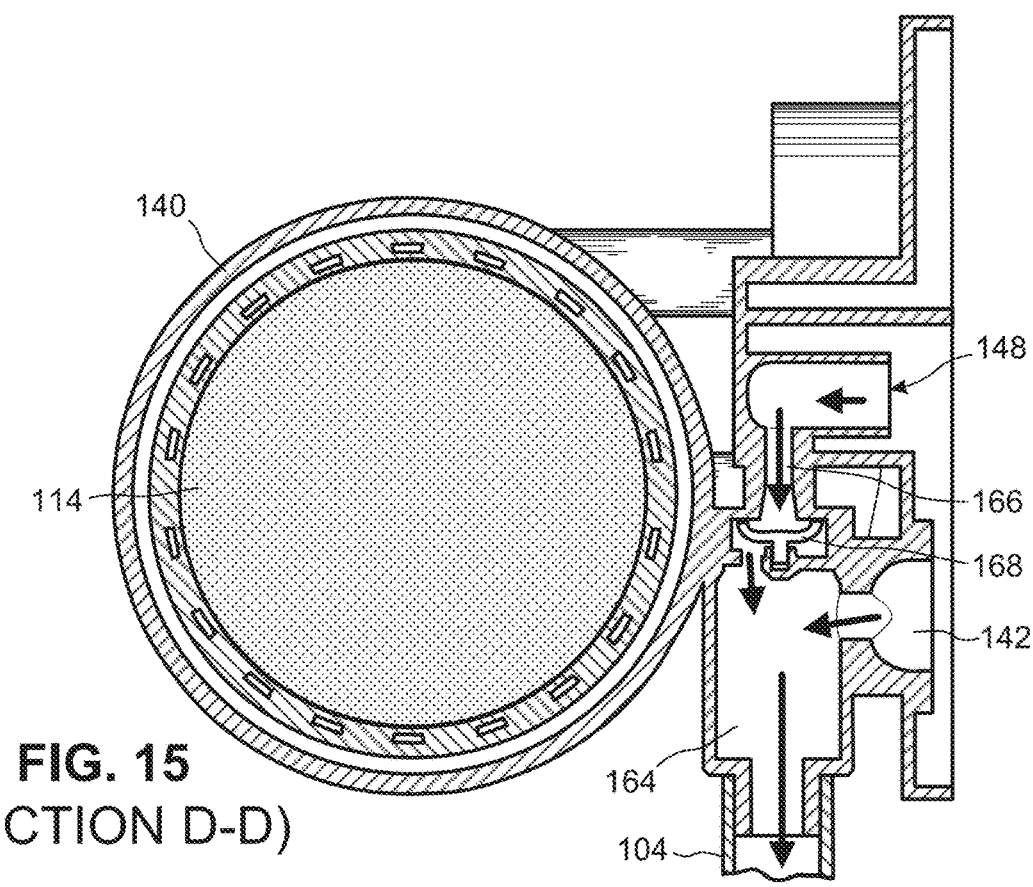
FIG. 15 is a cross-sectional view of the dialyzer of the blood treatment system of FIG. 1 taken along section line D-D of FIG. 10.

As shown, for example, in FIGS. 13 and 14, blood that has passed through the fiber bundle 114 in the dialyzer 100 and into the second end cap 140 exits the upper dome 145 via a blood exit tube 105.

The second end cap 140 also includes the air purge member 144. The air purge member 144 can be located at the apex of the upper dome 145. The air purge member 144 can serve multiple purposes, such as for purging air (venting) and as an access port (e.g., for sample extraction or administering medicaments). FIG. 29 shows a cross-sectional view of another example venous end cap 340 that differs from end cap 140 in that includes an access port 380 (in this case, a needleless access port) in addition to the air purge member 344. The access port 380 may be used to administer medicaments or extract samples.

From the blood exit tube 105, the blood enters the venous pressure detection chamber 142 (having its exterior flexible membranous wall 162) via a venous pressure detection chamber inlet 142i. The blood exits the venous pressure detection chamber 142 via a venous pressure detection chamber outlet 142o. The flow of the blood through the venous pressure detection chamber 142 allows a venous pressure transducer 252 (illustrated in FIG. 31) of the blood treatment module 200 to measure the venous blood pressure via membrane 162.

After exiting the venous pressure detection chamber 142, the blood then flows into a venous mixing chamber 164. The blood can either pass through the venous mixing chamber 142 without post-dilution or be mixed with substituate fluid, such as, for example, when the blood treatment system 1 is operating in a post-dilution HDF mode.

In situations (e.g., post-dilution HDF) where substitute is added to the venous mixing chamber, the substituate flows into the second end cap 140 from a second substituate supply conduit 256 (illustrated in FIG. 31) via the second substituate liquid inlet port 148. The substituate flows through a venous substituate supply tube 166. The substituate then passes through a check valve 168 and into the venous mixing chamber 164. This flow of substituate is illustrated via the series of arrows in FIG. 15 extending from the second substituate liquid inlet port 148 to the outlet of the check valve 168. In the venous mixing chamber 164, the substituate mixes with the incoming venous blood flow from the venous pressure detection chamber 142. The check valve 168 prevents the flow of blood into the venous substituate supply tube 166 and the second substituate liquid inlet port 148. This prevents blood contamination of the second substituate supply conduit 256.

The blood (whether or not post-diluted) exits the venous mixing chamber 164 into the venous blood line 104 which conveys the dialyzed blood back to the patient.

The second end cap 140 also includes the dialysate inlet port 149. The dialysate flows from the dialysate inlet port 149 through a dialysate supply tube 150 to a peripheral inner wall area of the second end cap 140.

Figure 17:
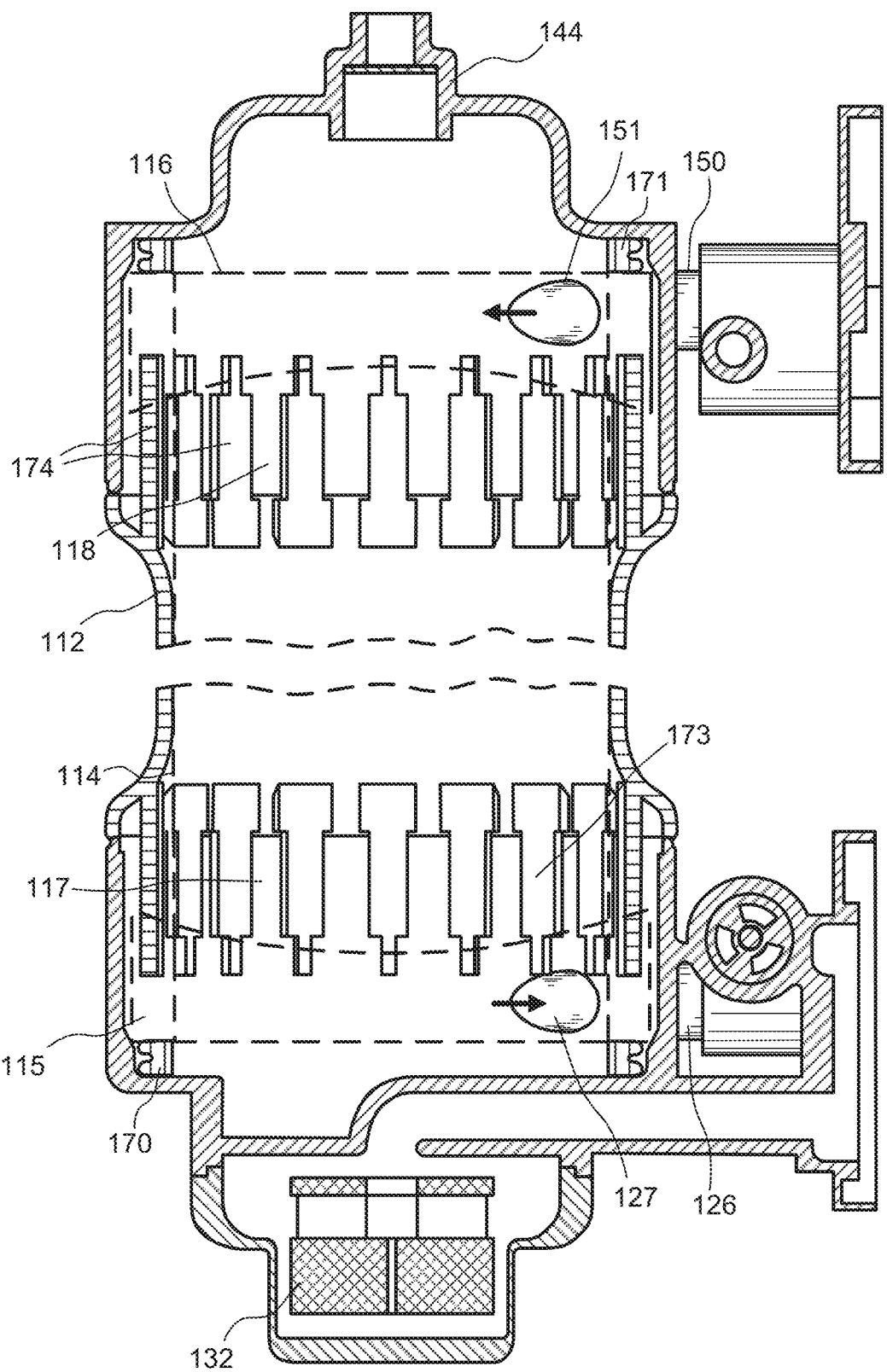
FIG. 17 is a broken cross-sectional view of the dialyzer of the blood treatment system of FIG. 1 taken along section line B-B of FIG. 11, with the bundle of hollow fibers and the pottings shown in broken lines.
Figure 18:
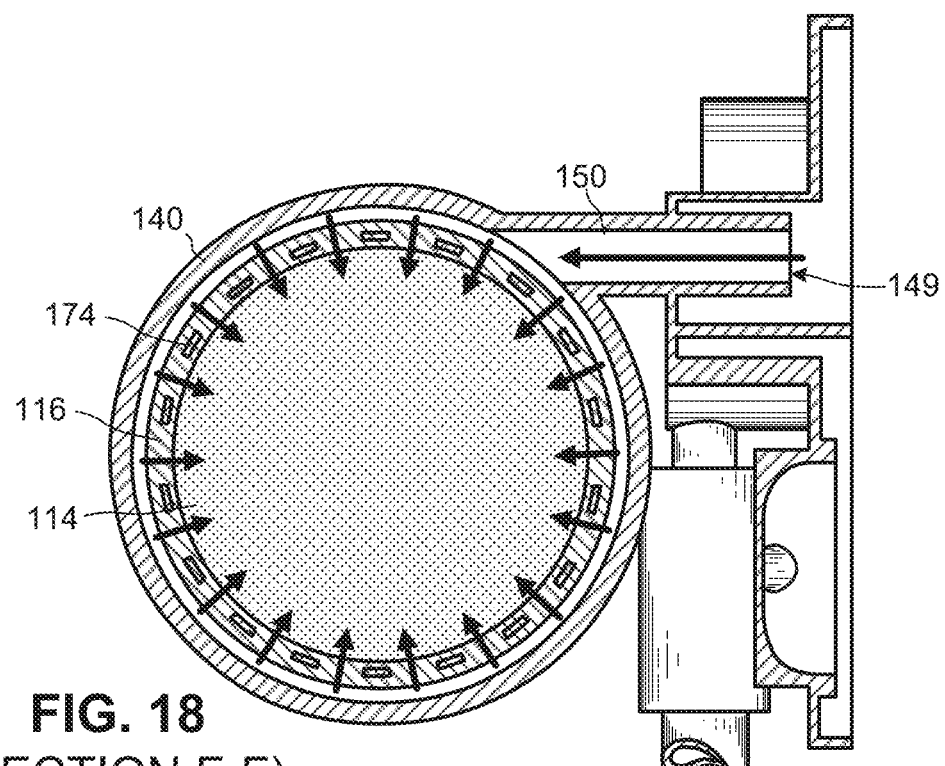
FIG. 18 is a cross-sectional view of the dialyzer of the blood treatment system of FIG. 1 taken along section line F-F of FIG. 10.
Figure 19:
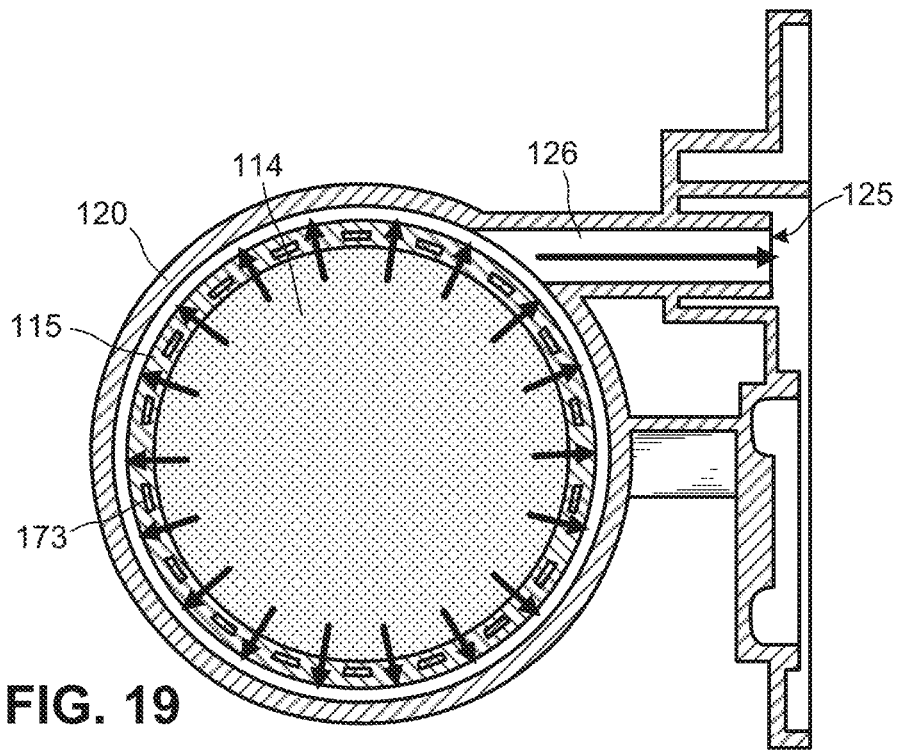
FIG. 19 is a cross-sectional view of the dialyzer of the blood treatment system of FIG. 1 taken along section line G-G of FIG. 10.

The flow path of the dialysate from the dialysate supply conduit 257 to the dialysate outlet conduit (or spent dialysate conduit) 255 is illustrated in FIGS. 17 to 19. The blood treatment module 200 is actuated to a) fluid-tightly engage the dialysate supply conduit 257 (illustrated in FIG. 31) with the dialysate inlet port 149 and b) fluid-tightly engage the spent dialysate conduit 255 with the spent dialysate outlet port 125. The flow of dialysate then begins with the dialysate flowing through the dialysate supply tube 150 into the space between the venous end cap 140 and the potting 116. The dialysate flows from this space axially beyond the potting 116 and radially inwardly through openings 118 between axially extending fingers 174 of the middle housing portion 112. The ends of the fingers 174 are embedded in and support the potting 116. The dialysate path is sealed from the blood volume in the venous end cap 140 by the gasket 171.

The dialysate's radial inflow via the openings 118 (with the fingers 174 helping to distribute the dialysate flow) causes the dialysate to be distributed circumferentially in a ring-like manner as it flows radially into the spaces between the hollow fibers 114. This peripherally concentrated dialysate flow aligns with, or coincides with, the flow of the blood through the lumens of the hollow fibers 114 in that the blood enters the hollow fibers 114 through the peripherally-located openings/slots 123 of the first end cap 120. Accordingly, the design of the dialyzer 100 causes the highest flow concentrations of the dialysate and the blood in the region of the hollow fibers 114 to be matched with each other. This matching of blood and dialysate flow concentrations enhances the blood treatment efficiency of the dialyzer 100.

After passing through the openings 118, the dialysate flows between the hollow fibers 114 and continues to flow axially downwardly until reaching the arterial end cap 120. Since potting 115 blocks further axial flow between the fibers 114, the dialysate flows radially outwardly through openings 117 between fingers 173 of the middle housing portion 112, which are embedded in and support the potting 115. The dialysate path is sealed from the blood volume in the arterial end cap 120 by the gasket 170. The dialysate then flows into the space between the arterial end cap 120 and the potting 115. The dialysate then enters the spent dialysate outlet tube 126 via a spent dialysate tube inlet 127. Spent dialysate tube 126 then conveys the dialysate to the dialysate outlet port, where it flows into the spent dialysate conduit 255 (illustrated in FIGS. 31-33) of the blood treatment module 220.

Figure 30:
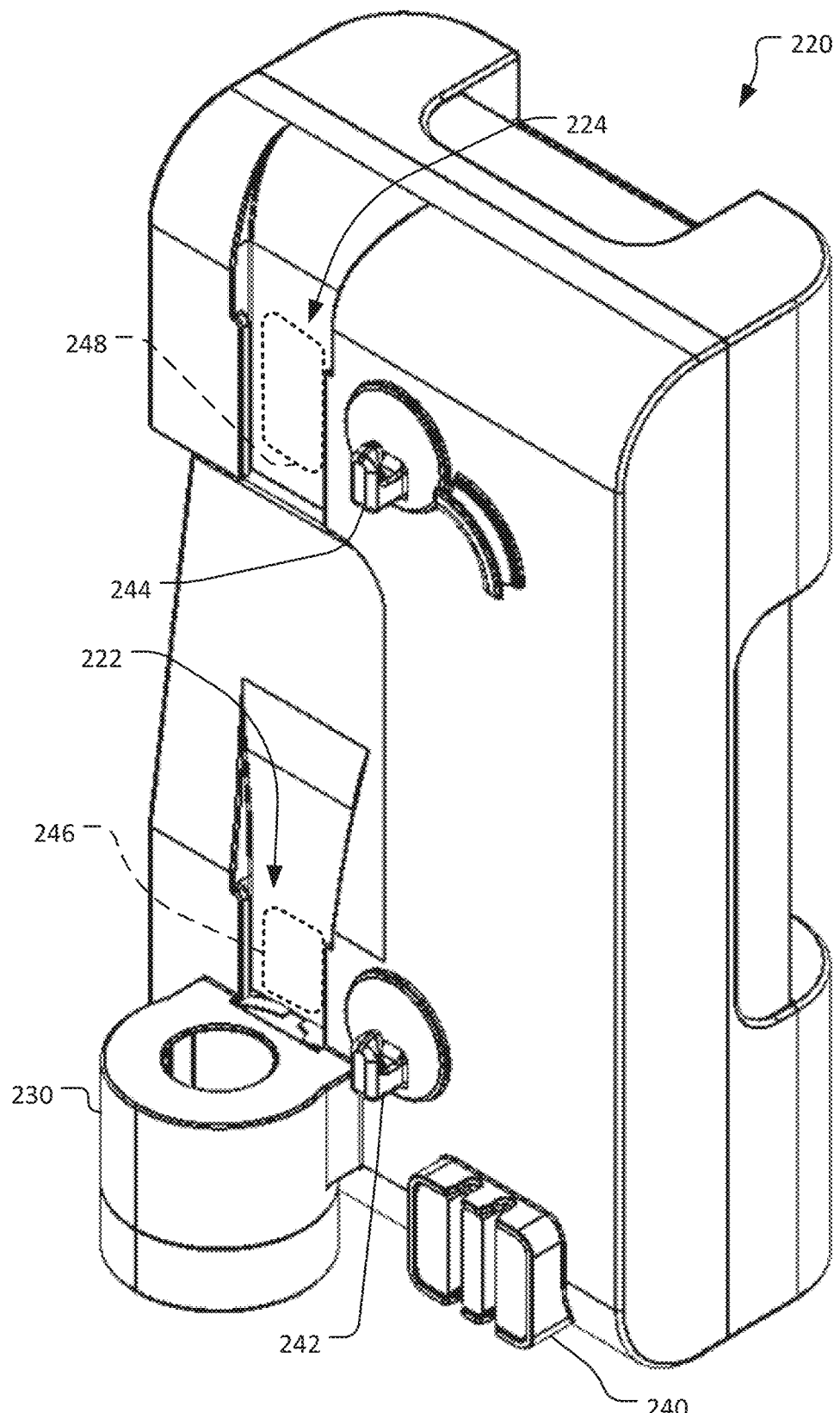
FIG. 30 is a perspective view of the treatment module of the blood treatment system of FIG. 1 in a first configuration.
Figure 31:
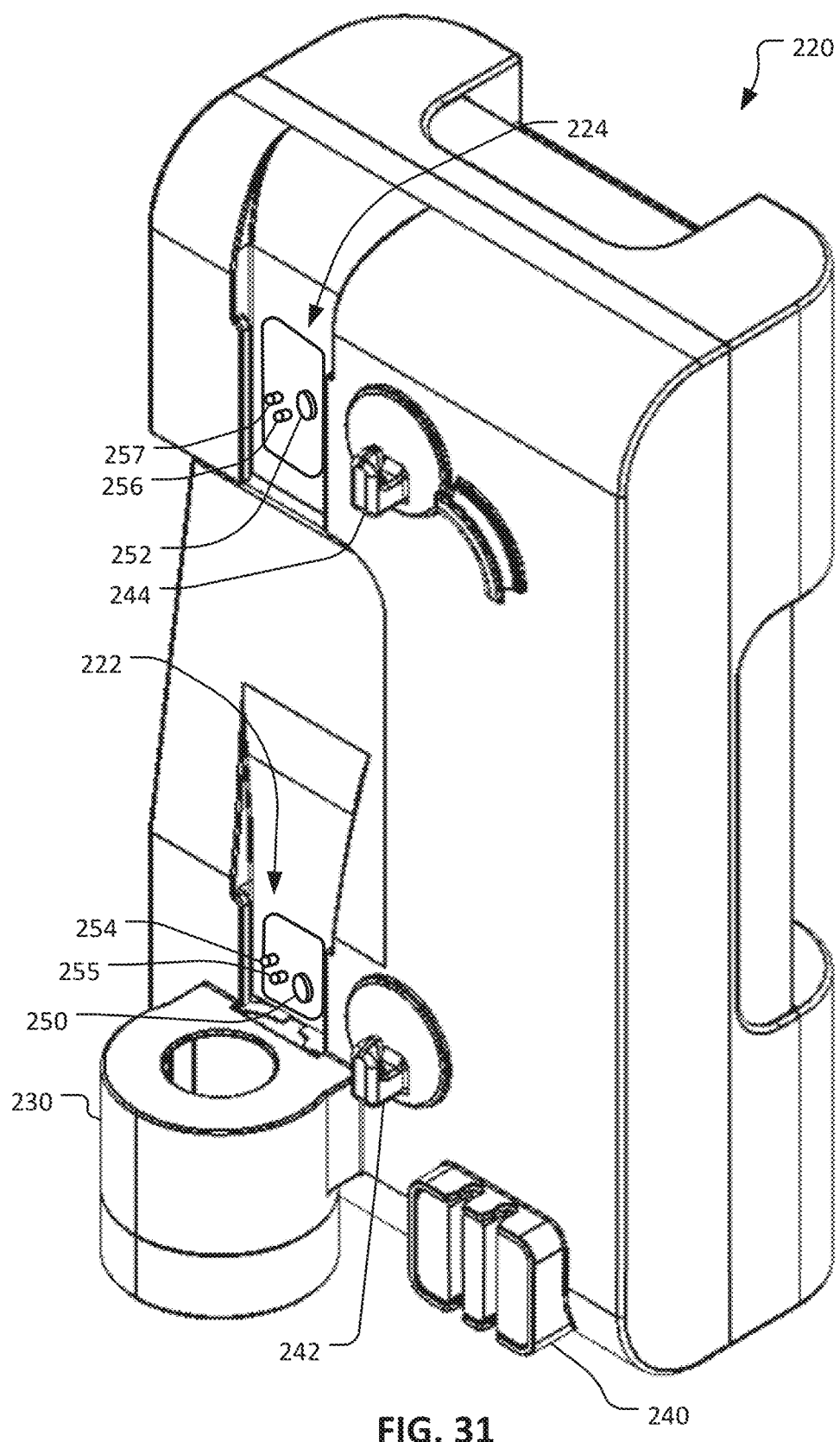
FIG. 31 is a perspective view of the treatment module of FIG. 30 in a second configuration.

Referring to FIGS. 30 and 31, the treatment module 220 defines the first complementarily shaped slot 222 and the second complementarily shaped slot 224 that configure the treatment module 220 to be slidably coupleable with the first projection 106 and the second projection 108 of the dialyzer 100 (e.g., FIGS. 2, 10, and 17). The treatment module 220 also includes the arterial line clamp 242 and the venous line clamp 244. The clamps 242 and 244 are used to either fully restrict or fully un-restrict the flow of blood within the arterial line 102 and/or the venous line 104 (e.g., in an on/off valve fashion), or to modulate the flow of blood through the arterial line 102 and/or the venous line 104 (e.g., across a range of partially restricting clamp settings).

The treatment module 220 also includes the tubing interface module 240 configured to releasably receive a portion of the arterial line 102 and/or a portion of the venous line 104. The tubing interface module 240 can include devices to perform functions such as flow rate detection, gaseous bubble detection, and the like. That is, the tubing interface module 240 can include sensors for detecting, for example, a flow rate of the blood within the arterial line 102 and/or the venous line 104, and/or for detecting gaseous bubbles (e.g., air bubbles) in the blood within the arterial line 102 and/or the venous line 104. The flow rate detection and/or the bubble detection can be performed using sensors such as ultrasonic sensors, optical sensors, or other suitable types of sensors.

The treatment module 220 also includes the pump drive unit 230. The pump drive unit 230 is configured to releasably receive the pump housing 130 of the dialyzer 100 (shown in FIGS. 8, 9, 13, and 15) when the dialyzer 100 is coupled to the treatment module 220. During operation of the treatment module 220, one or more electrical coils within the pump drive unit 230 are dynamically energized by the control system of the blood treatment machine console 210 (shown in FIG. 1). The energization of the one or more electrical coils generates dynamic magnetic fields (magnetic fields that move or modulate) that cause the magnetic pump rotor (e.g., rotor 132 or rotor 137) to levitate out of contact with the walls of the pump housing 130 and to rotate at a desired rotational speed. Alternatively, in some embodiments, a mechanical coupling can be used to couple a pump drive unit to a pump rotor within a dialyzer.

The pump drive unit 230 in conjunction with the control system of the blood treatment machine console 210 (shown in FIG. 1) can also be used for monitoring various conditions of the dialyzer 100. For example, it can be detected whether the pump housing 130 of the dialyzer 100 is in the operative position relative to the pump drive unit 230. Additionally, the presence of air in the pump housing 130 can be detected. If air is detected within the pump housing 130, substitute can be added via the first substitute liquid port 124 to prime the magnetic pump rotor. Occlusions within the dialyzer 100 can also be detected by the pump drive unit 230 in conjunction with its control system.

The treatment module 220 also includes pressure measurement devices that interface with the dialyzer 100 to measure pressures in the arterial pressure detection chamber 122 and the venous pressure detection chamber 142 (shown in FIGS. 8, 11, 12, 18, and 19). Moreover, the treatment module 220 includes conduits for supplying substitute (via the substitute liquid ports 124 and 148) to the dialyzer 100 and for conveying dialysate (via the dialysate ports 125 and 149) to and from the dialyzer 100. Such pressure measurement devices and conduits can be controlled by the treatment module 220 to extend to engage with the dialyzer 100, and retract to disengage from the dialyzer 100.

In FIG. 30, the pressure measurement devices and conduits are retracted and covered by a first door 246 and a second door 248. In FIG. 31, the doors 246 and 248 are opened, and the pressure measurement devices and conduits are extended (as they would be in order to interface with the dialyzer 100). When closed, the doors 246 and 248 allow for convenient wiping to clean the outer surfaces of the treatment module 220. Additionally, with the pressure measurement devices and conduits retracted internally within the treatment module 220 (and the doors 246 and 248 closed), the pressure measurement devices and conduits can be automatically cleaned and prepared for subsequent use while they are within the treatment module 220.

In FIG. 31, the doors 246 and 248 are in their opened positions and the pressure measurement devices and conduits are extended into their operative positions (as if a dialyzer 100 was coupled with the treatment module 220). For example, a first pressure transducer 250 is extended to interface with the flexible membrane wall of the arterial pressure detection chamber 122 of the dialyzer 100, and a second pressure transducer 252 is extended to interface with the flexible membrane wall of the venous pressure detection chamber 142 of the dialyzer 100.

Additionally, the treatment module 220 includes two pairs of conduits that can automatically interface with the dialyzer 100 to facilitate flow of liquids such as substitute and/or dialysate between the dialyzer 100 and the treatment module 220. For example, a first pair of conduits (a first substitute supply conduit 254 and a dialysate outlet conduit 255) is positioned to respectively couple with the first substitute liquid port 124 and the dialysate outlet port 125 located on the first end cap 120 of the dialyzer 100. In addition, a second pair of conduits (a second substitute supply conduit 256 and a dialysate supply conduit 257) is positioned to respectively couple with the second substitute liquid port 148 and the dialysate inlet port 149 located on the second end cap 140 of the dialyzer 100. The extension and retraction of the conduits 254-257 and the pressure measurement transducers 250 and 252 can be controlled by the control system of the blood treatment machine 200 (FIG. 1).

Figure 32:
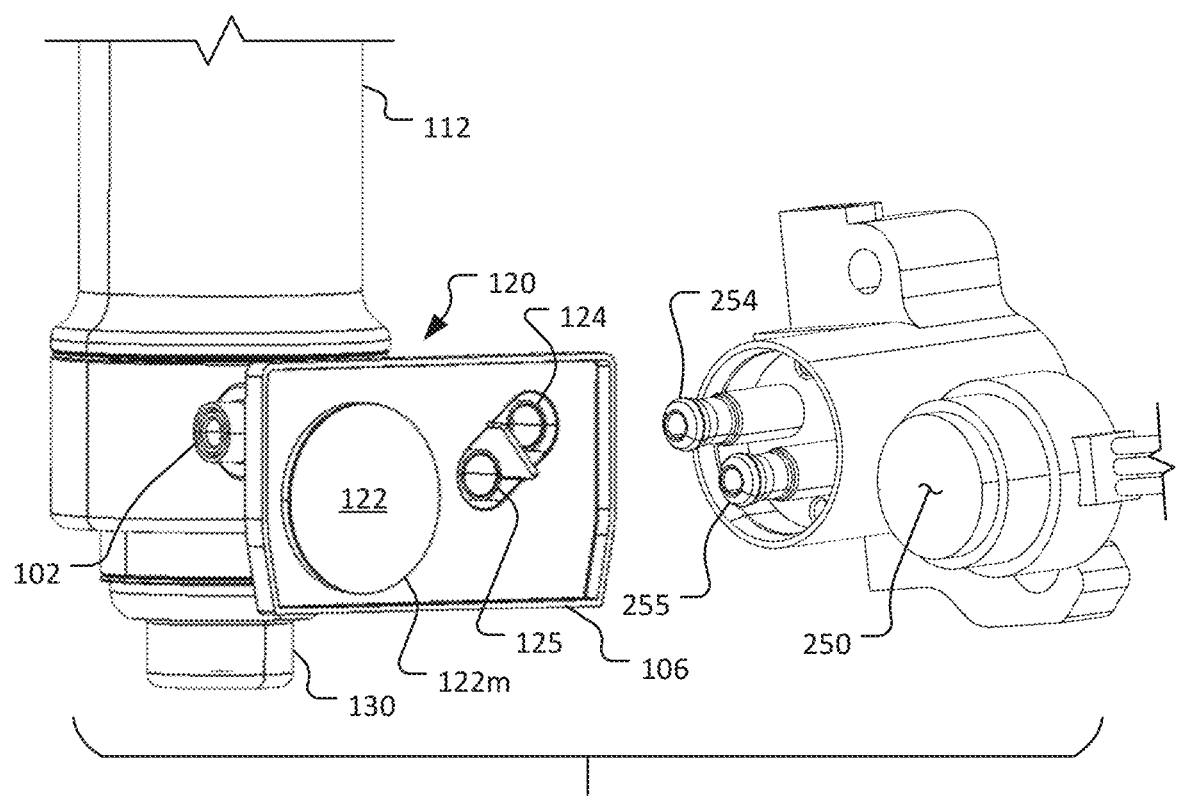
FIG. 32 is an exploded perspective view showing the first end cap of FIG. 20 and a first pressure sensor and a first pair of conduits of the treatment module of FIG. 30.
Figures 33, 34:
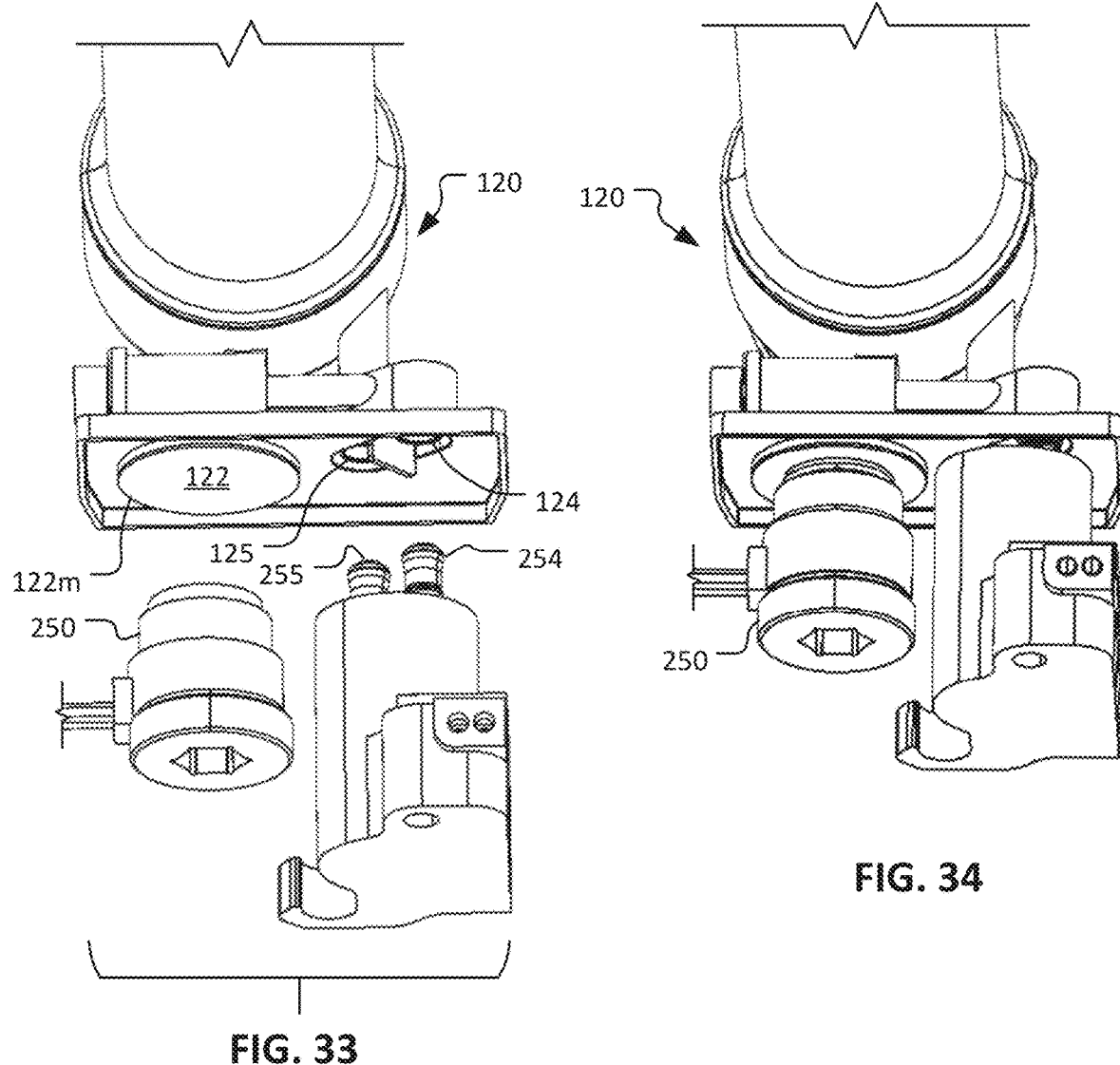
FIG. 33 is a top perspective view of the first end cap, the first pressure sensor, and the first pair of conduits of FIG. 32 shown in a separated configuration.
FIG. 34 is a top perspective view of the first end cap, the first pressure sensor, and the first pair of conduits of FIG. 32 shown in an operative, coupled configuration.

Referring to FIGS. 32-34, isolated views showing greater detail of how the first end cap 120 interfaces with the first pressure transducer 250, the first substitute supply conduit 254, and the dialysate outlet conduit 255 are provided. It should be understood that the relative arrangement of the second end cap 140 in relation to the second pressure transducer 252, the second substitute supply conduit 256, and the dialysate supply conduit 257 is analogous.

The face of the first pressure transducer 250 (when extended, as shown in FIG. 24) abuts against a flexible membrane 122m that serves as an exterior wall of the arterial pressure detection chamber 122. The first substitute supply conduit 254 (when extended, as shown in FIG. 24) fluidly couples with the first substitute liquid port 124 in a liquid-tight manner. The dialysate outlet conduit 255 (when extended, as shown in FIG. 24) fluidly couples with the dialysate outlet port 125 in a liquid-tight manner.

In order to provide a highly efficacious interface between the flexible membrane 122m and the first pressure transducer 250, the arterial pressure detection chamber 122 is pressurized prior to extending the first pressure transducer 250 into contact with the flexible membrane 122m. While the arterial pressure detection chamber 122 is pressurized, the flexible membrane 122m will bulge outward to present a convex surface to the first pressure transducer 250. Then, while the flexible membrane 122m is bulged outward, the first pressure transducer 250 is extended to abut against the flexible membrane 122m so as to seal the interface therebetween. This technique can help to establish strong coupling cohesion between the first pressure transducer 250 and the flexible membrane 122m by reducing the potential for air pockets therebetween, for example. In some embodiments, negative air pressure (vacuum) can be applied to create or enhance the coupling cohesion between the first pressure transducer 250 and the flexible membrane 122*m*.

Figure 35:
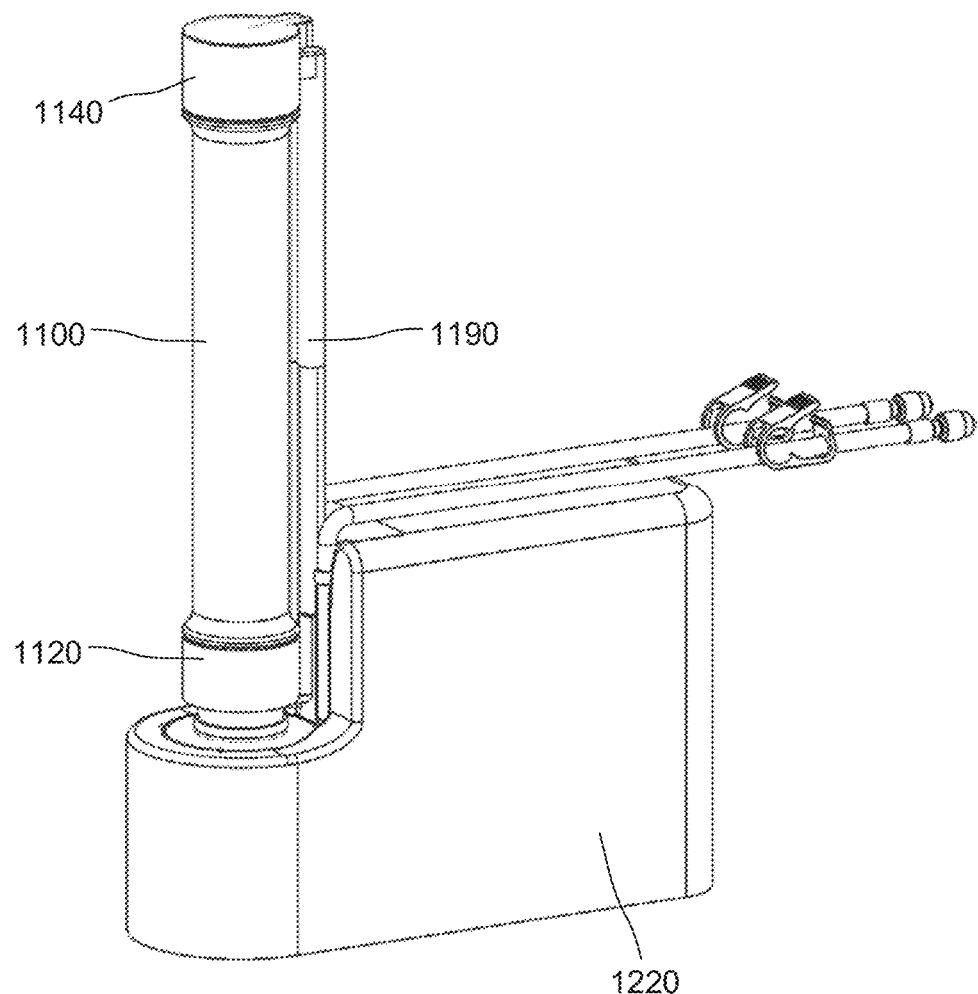
FIG. 35 is a perspective view of an alternative treatment module.

FIG. 35 shows another example blood treatment module 1220 and dialyzer 1100. This arrangement differs from that of module 220 and dialyzer 100 in that the dialysate and substitute ports and the pressure chambers and membranes are instead located in the arterial end cap. Accordingly, the blood treatment module 1220 interfaces only the arterial end cap 1120 for supplying fresh dialysate, receiving spent dialysate, supplying pre- and post-dilution substitute fluid, and monitoring arterial and venous pressures. In this arrangement, a pair of tubes 1190 are provided to convey the fresh dialysate and the post-dilution substitute from the arterial end cap 1120 to the venous end cap 1140.

Figure 36:
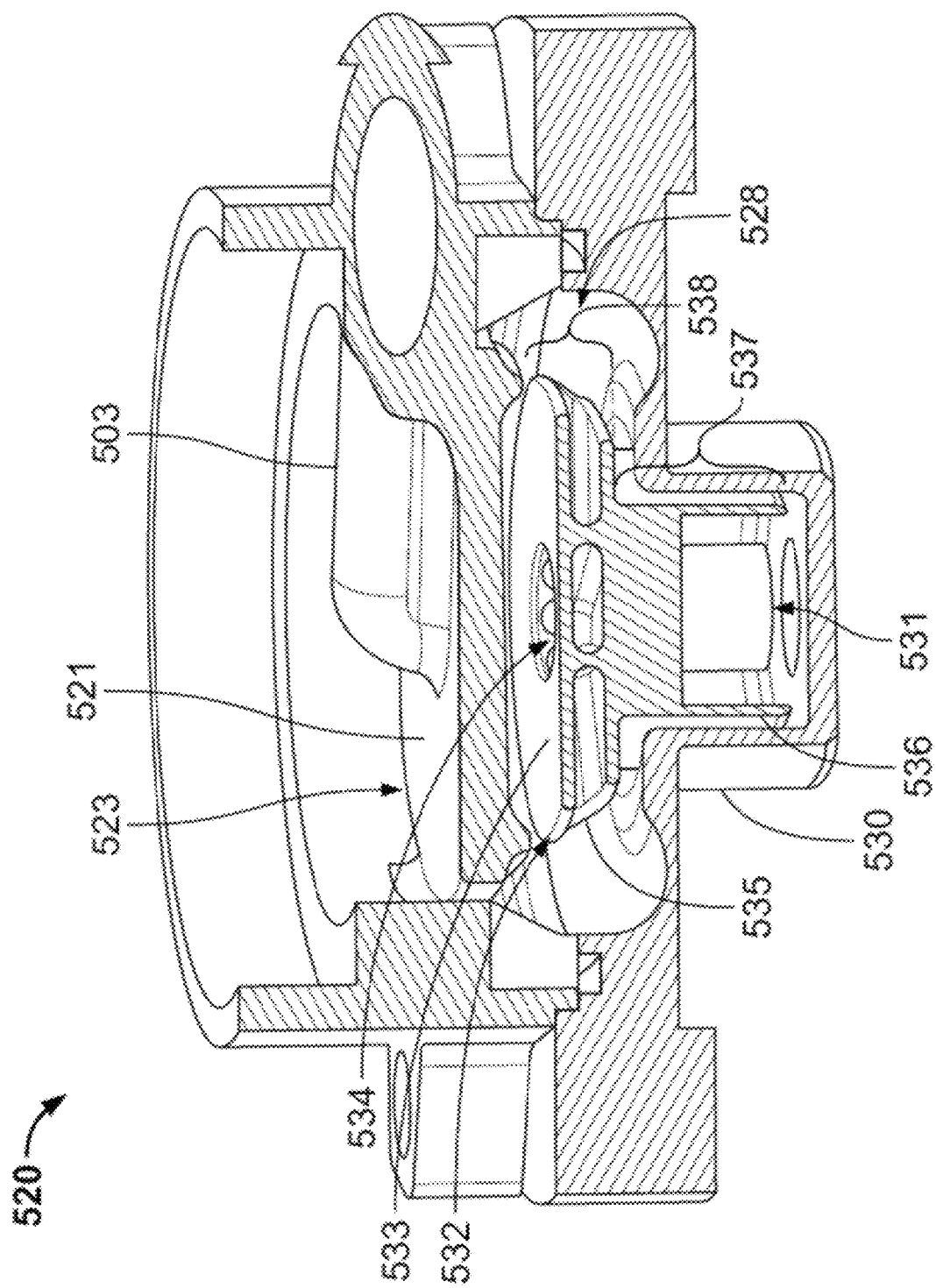
FIG. 36 is a perspective view of an alternative first (arterial) end cap shown in a partial longitudinal cross-sectional view.

FIG. 36 is a perspective view of an alternative first (arterial) end cap 520 shown in a partial longitudinal cross-sectional view. The end cap 520 can be used with the dialyzer 100 as an alternative to the end cap 120, for example.

The incoming blood flows toward the pump housing 530 through the rotor supply tube 503 that is supported by an internal support plate 521. A 90° elbow at the end of the rotor supply tube 503 directs the blood to turn and flow parallel along the longitudinal central axis of the dialyzer 100 at the center of the first end cap 520. From the exit of the rotor supply tube 503, the blood is delivered to a center of a pump rotor 532 located within the pump housing 530. The blood radially exits the pump rotor 532 into a toroidal space 528 circumferentially surrounding the portion of the rotor 532 that includes blades 535. The toroidal space 528 is shaped so as to direct the blood axially toward the bundle of hollow fibers. The toroidal space 528 is partially defined by annular concave wall surface of the housing 530, which is opposite of the bundle of hollow fibers. After being redirected from radial flow to longitudinal flow in the toroidal space 528, then the blood passes through one or more openings 523 defined in the internal support plate 521 and continues flowing toward the bundle of hollow fibers. In some embodiments, the openings 523 are slots (e.g., linear or arcuate slots). Any number of openings 523, such as one, two, three, four, five, six, seven, eight, or more than eight can be included.

The pump rotor 532 includes first end portion 537 and a second end portion 538 that are on opposite ends of the pump rotor 532. The first end portion 537 houses, or has attached thereto, one or more magnets, such as a magnetic disc 536. The second end portion 538 comprises a first plate 533 and a plurality of vanes 535 extending between the first plate 533 and the magnetic disc 536. The first end portion 537 is diametrically smaller than the second end portion 538.

In accordance with some embodiments, the pump rotor 532 is a pump impeller comprising a radially pumping pump wheel with a hollow central volume. Accordingly, the depicted pump rotor 532 can also be referred to a pump impeller. The vanes 535 of the pump wheel (second end portion 538) of the pump rotor 532 can be arranged so that they project or extend at least partially radially. In some cases, the blades are arranged to project or extend entirely radially. In some cases, the blades are arranged to project or extend partially radially and partially tangentially. The first plate 533 is an annular ring that defines a central aperture 534. The magnetic disc 536 defines a central lumen 531 that extends along the longitudinal central axis Z of the dialyzer 100. The magnetic disc 536 can include one or more encapsulated or non-encapsulated bi-pole magnets (e.g., a rare earth magnet, a ferrite ceramic magnet, and other suitable types of magnets). In the depicted embodiment, the vanes 535 are arcuate members, but the vanes 535 can be linear members in some embodiments.

In some embodiments, the components of the end cap 520 can have the same physical dimensions and dimensional interrelations as described above in reference to the components of the end cap 120. However, the end cap 520 differs from the end cap 120 at least in the following aspects. The outer edges of the vanes 535 are not parallel to the center axis. Instead, an acute angle is defined between the outer edges of the vanes 535 and the center axis. In some embodiments, the acute angle is in a range of 0° to 60°, or 0° to 45°, or 5° to 40°, or 10° to 35°, or 20° to 35°, or 25° to 35°, or 30° to 45°, without limitation. In addition, in some embodiments the height of the vanes 535 are less than the height of the vanes 135. For example, in some embodiments the height of the vanes 535 (measured along the longitudinal central axis Z) is in a range of 1 mm to 8 mm, or 1 mm to 6 mm, or 1 mm to 5 mm, or 1 mm to 4 mm, or 1 mm to 3 mm, or 2 mm to 3 mm, without limitation. Further, the toroidal space 528 is shaped differently from the toroidal space 128. For example, the inner surface of the housing that defines the lower wall of the toroidal space 528 is concave (curved downward), whereas the lower surface of the toroidal space 128 is planar or curved upward. The shape of the toroidal space 528 promotes vortexing in the flow that exits radially from the pump rotor 532 and promotes a transition (redirection) of the flow toward the upward axial direction.

These physical features of the end cap 520, and its pump rotor 532, serve to maximize axial thrust of the blood flow and to stabilize the pump rotor 532 during operation. In essence, pump rotor 532 and the toroidal space 528 redirect the blood flow by 180° instead of 90°. In some embodiments, blood is introduced axially in the "top" of the pump rotor 522 and is conveyed to the "bottom" of the rotor 532.

The blood exits the end cap 520 via the one or more openings 523 in a circular pattern that is concentric to the central aperture 534. The one or more openings 523 can be a symmetrical circular arrangement of holes, or one or more slits in the shape of circular/arcuate segments. Accordingly, no eccentric forces act upon the pump rotor 532 (unlike most centrifugal pumps having a tangential outlet). As a consequence, the pump rotor 532 is more stable (e.g., with substantially reduced tilting moment) during operation, and the dimensional gaps between it and the surrounding housing surfaces remain within tolerance. Advantageously, because the pump rotor 532 is more stable during operation, the strength of the magnetic field required for levitating and driving the pump rotor 532 is lessened. So, for example, in some embodiments lower cost hard ferrite magnets can be used, thereby substantially reducing the cost of the pump rotor 532.

The shape of the toroidal space 528 promotes a transition (redirection) of the flow of blood from radial toward the upward axial direction. That upward blood flow from the toroidal space 528 is substantially concentrated at the periphery or circumference of the exit from the toroidal space 528. That concentration of blood flow also advantageously aligns with the locations of the openings 523 (which are, in turn, in alignment with outer peripheral portions of the bundles of hollow fibers). Moreover, as described above in reference to FIGS. 17-19, the dialysate's flow is concentrated in a circumferential ring-like manner as it flows radially into the spaces between the hollow fibers 114. The peripherally-concentrated dialysate flow aligns with, or coincides with, the peripherally-concentrated flow of the blood through the lumens of the hollow fibers 114. Accordingly, the design of the dialyzer 100 advantageously causes or aligns the highest flow concentrations of the dialysate and the blood to be matched in the same areas with each other. This matching of blood and dialysate flow concentrations enhances the blood treatment efficiency of the dialyzer 100.

While certain embodiments have been described, other embodiments are possible, and are within the scope of this disclosure.

While systems capable of HDF are described, some embodiments omit substitute ports. Such machines may perform hemodialysis but not include HDF capability. For example, a dialyzer 2100 that is configured like the dialyzer of the blood treatment system of FIG. 1, except without HDF capability is depicted in FIGS. 37-39. The housing 2110 of the dialyzer 2100 includes a first end cap 2120, a second end cap 2140, and a middle housing portion 2112 that extends between the first end cap 2120 and the second end cap 2140. The middle housing portion 2112 contains the majority of the length of a bundle of hollow fibers 2114.

The first end cap 2120 includes a pump housing 2130. A rotatable centrifugal pump rotor (not visible) is located within the pump housing 2130. As described further herein, the pump rotor is operated and controlled by interfacing with the pump drive unit (e.g., as shown in FIGS. 2 and 3) of the treatment module 220. That is, the pump rotor can be levitated and rotated by magnetic fields that are caused to emanate from the pump drive unit during use.

The housing 2110 defines one or more pressure detection chambers. The depicted embodiment includes an arterial pressure detection chamber 2122 and a venous pressure detection chamber 2142. The arterial pressure detection chamber 2122 is located prior to the pump rotor. That is, the arterial pressure detection chamber 2122 is arranged to facilitate measuring pre-pump arterial pressure. Additionally or alternatively, in some embodiments, pressure can be measured post-pump (but prior to the hollow fibers). The pressure detection chambers 2122 and 2142 are each configured to interface with a respective pressure transducer of the treatment module 220.

The dialyzer 2100 is configured to receive dialysate, and to direct the dialysate to flow through the housing 2110. For example, in the depicted embodiment, the second end cap 2140 defines a dialysate inlet port 2149 and the first end cap 2120 defines a dialysate outlet port 2125. The dialysate flows into the second end cap 2140 via the dialysate inlet port 2149, and then enters the middle housing portion 2112 containing the bundle of hollow fibers 2114. The dialysate flows through the middle housing portion 2112 via the spaces defined between the outer diameters of the fibers of the bundle of hollow fibers 2114. In other words, while the blood flows within the lumens of the fibers of the bundle of hollow fibers 2114, the dialysate liquid flows along the outsides of the fibers. The semi-permeable walls of the fibers of the bundle of hollow fibers 2114 separate the dialysate liquid from the blood. The dialysate liquid flows out of the middle housing portion 2112 and into the first end cap 2120. The dialysate liquid exits the first end cap 2120 via the dialysate outlet port 2125.

Figure 41:
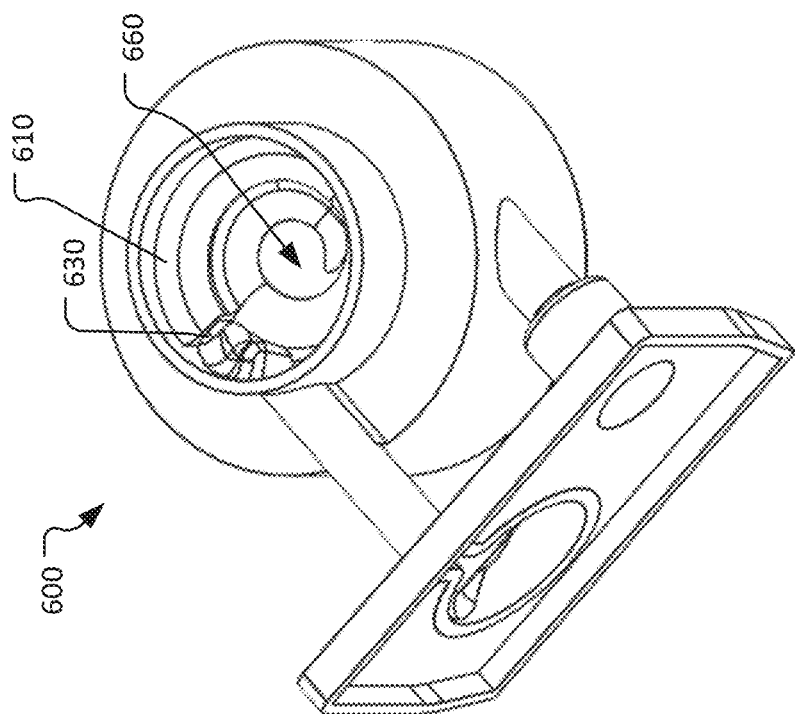
FIG. 41 is a perspective view showing a portion of the venous end cap of FIG. 40.
Figure 40:
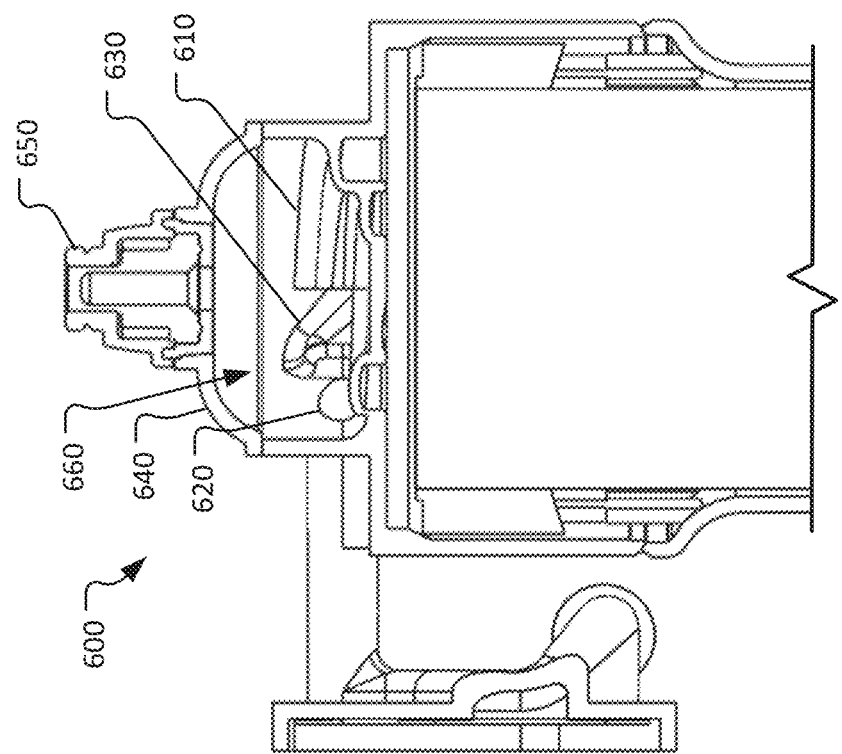
FIG. 40 is a longitudinal cross-sectional view of an alternative second (venous) end cap.

Referring to FIGS. 40 and 41, an alternative second (venous) end cap 600 can be used with any of the dialyzers described herein. The venous end cap 600 is configured with particular features to encourage separation of gases such as air from the extracorporeal circuit during priming and during use. The venous end cap 600 includes a spiral inlet lumen 610 (or spiral lumen 610), an outlet 620, an angled baffle 630, a dome 640, an air purge member 650, and a chamber 660. In FIG. 41, the dome 640 and air purge member 650 are not shown in order to provide better visibility of the structures inside of the chamber 660. An upper portion of the venous end cap 600 comprises the dome 640 and the attached air purge member 650. A lower or bottom portion of the venous end cap 600 defines the spiral inlet lumen 610 and its outlet 620, and comprises the angled baffle 630. The spiral inlet lumen 610 and the angled baffle 630 can be integrally formed with the lower portion of the venous end cap 600. The outlet of the spiral inlet lumen 610 is located between the upper portion of the venous end cap 600 and the outlet 620 of the chamber 660.

In use, blood exits the lumens of the hollow fibers and flows to the chamber 660 via an inlet to the spiral inlet lumen 610 and by the spiral inlet lumen 610 itself. In other words, the spiral inlet lumen 610 provides fluid communication between the chamber 660 and areas exterior to the chamber 660. The inlet to the spiral inlet lumen 610 is configured on the bottom side of the bottom portion of the venous end cap 600. The inlet to the spiral inlet lumen 610 has a larger area than a transverse cross-section of the spiral inlet lumen 610. The outlet of the spiral inlet lumen 610 is configured on the upper side of the bottom portion. The spiral inlet lumen 610 extends from the lower portion of the venous end cap 600 and spirals vertically toward the upper portion of the venous end cap 600 (toward the dome 640). The spiral inlet lumen 610 is configured so that the blood entering the chamber is flowing essentially horizontally (i.e., transverse to the longitudinal axis of the dialyzer). The outlet of the spiral inlet lumen 610 (i.e., where the spiral inlet lumen 610 terminates within the chamber 660) is near to the peripheral wall of the chamber 660. In other words, the outlet of the spiral inlet lumen 610 is offset from the central axis of the dialyzer and of the venous end cap 600 itself. Accordingly, blood flowing into the chamber 660 may tend to impact the peripheral wall of the chamber 660, which will engender a spiral flow path to the blood.

The angled baffle 630 is located adjacent to the outlet of the spiral inlet lumen 610, such that blood exiting the spiral inlet lumen 610 will tend to impact on the angled baffle 630 and be deflected upward toward the dome 640, which is a rigid portion of the housing such that it defines the fixed shape of the upper portion of the chamber 660. The impact surface of the angled baffle 630 can be angled at an acute angle in relation to the essentially horizontal blood flow direction as the blood exits the spiral inlet lumen 610. For example, in some embodiments the angle of the angled baffle 630 relative to horizontal, and/or relative to the central longitudinal axis of the dialyzer and venous end cap 600, is in a range of 10° to 70°, or 20° to 60°, or 30° to 50°, or 30° to 40°, without limitation.

The air purge member 650 allows air and other gases to exit the venous end cap 600 while preventing fluids such as blood from exiting therethrough. The air purge member 650 can also be used as an access port. That is, the air purge member 650 can be configured for uses such as sample extraction and administration of medicaments (e.g., heparin).

To perform optimally as an air separator during use, the venous end cap 600 needs to be substantially cleared of air by priming prior to the start of a blood treatment. That is, sufficient air needs to be cleared from the chamber 600 during the priming phase for the chamber 660 to be optimally effective for separating air later on during the blood treatment. During priming, it is intended that air in the chamber 660 is substantially flushed out of the chamber 660 by a priming solution. By virtue of the velocity and directional flow engendered by the structure of the venous end cap 600, the efficacy of the priming solution to remove air from the chamber 660 is enhanced (e.g., with air flushed out through a rinse port positioned on the blood treatment machine). Otherwise, air remaining in the chamber 660 can also be manually removed via the air purge member 650 by connecting a syringe to the air purge member 650, for example.

During use, the flow velocity engendered by the structure of the venous end cap 600 presents a challenge for air separation as air in the blood needs time to be influenced by the forces of gravity and can remain trapped in the blood. The structure of the venous end cap 600 causes a circular, spiral-like flow that can act to slow the velocity of blood flow. Accordingly, air tends to migrates toward the center of the spiral flow where velocity is the lowest, and where effects of gravity have time to act on the air so that it can separate from the blood and be collected at the top of the dome 640.

While the structures of the venous end cap 600 that function to deaerate liquids are described above in the context of an end cap of a dialyzer, it should be understood that the structures for deaeration can be incorporated in conjunction with various other types of devices, or as a deaeration device to itself. That is, the structures for deaeration of the venous end cap 600 can be incorporated as portions of a deaeration chamber that can be implemented in a wide variety of suitable embodiments. Additionally, while the venous end cap 600 is primarily intended to deaerate blood, priming solution, or other medical liquids, it should be understood that the structures for deaeration of the venous end cap 600 can be implemented in other embodiments so as to deaerate other types of liquids.

Figure 44:
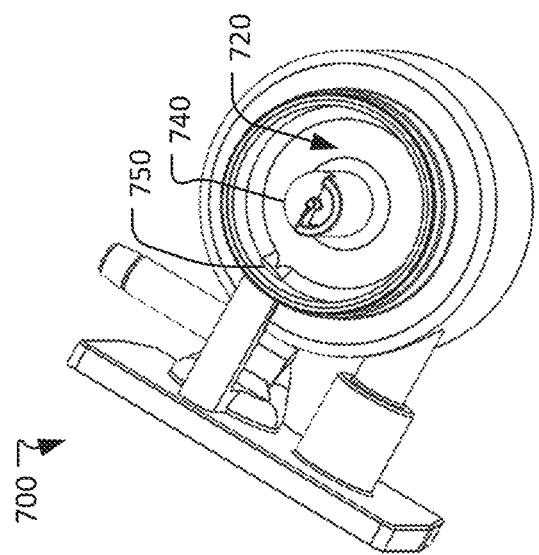
FIG. 44 is another perspective view of the venous end cap of FIG. 42.
Figure 43:
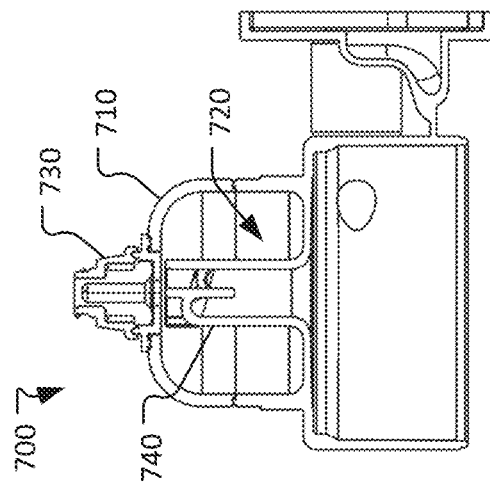
FIG. 43 is a longitudinal cross-sectional view of the venous end cap of FIG. 42.
Figure 42:
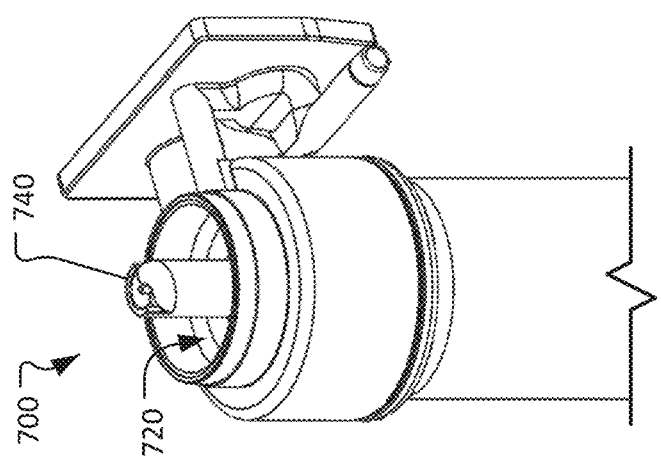
FIG. 42 is a perspective view of a portion of another alternative second (venous) end cap.

Referring to FIGS. 42-44, another alternative second (venous) end cap 700 can be used with any of the dialyzers described herein. The venous end cap 700 is configured with particular features to encourage separation of gases such as air from the extracorporeal circuit during priming and during use.

The venous end cap 700 includes an upper or top portion comprising a dome 710 and an attached air purge member 730 (shown in FIG. 43, but not shown in FIGS. 42 and 44). The venous end cap 700 includes a lower or bottom portion comprising an inlet passage member 740, and defining a chamber outlet 750 (FIG. 44). A chamber 720 is defined between the upper and lower portions of the venous end cap 700.

The inlet passage member 740 comprises a projection extending axially from the bottom portion of the venous end cap 700 along a central axis (e.g., longitudinal axis) of the venous end cap 700 (and a dialyzer as a whole). The inlet passage member 740 can be integrally formed with the lower portion of the venous end cap 700. The outlet of the inlet passage member 740 is at a terminal end of the projection, elevated above the chamber outlet 750, and elevated above a middle elevation of the chamber 720. The outlet of the inlet passage member 740 is radially offset from the central axis (e.g., longitudinal axis) of the venous end cap 700 (and a dialyzer as a whole). The dome 710 is a rigid upper portion of the housing such that it defines the fixed shape of the upper portion of the chamber 720.

The blood after being treated by the hollow fiber membrane enters the chamber 720 of the venous end cap 700 though the inlet passage member 740 formed in the axial middle of the venous end cap 700. An outlet end portion at the terminal end of the inlet passage member 740 is configured spirally (e.g., with a beveled surface, at an acute angle relative to the central axis, along which the blood exiting the inlet passage member 740 will flow). Accordingly, the outlet end portion at the terminal end of the inlet passage member 740 is configured to engender a spiral component to the flow path of the blood as it exits the inlet passage member 740 to enter the chamber 720. The blood enters the chamber 720 after spilling over from the terminal outlet end portion of the inlet passage member 740. The blood can be degassed by means of gravity (bubbles will tend to rise in relation to the blood and to separate from the blood) as it flows in a thin layer, and with a spiral flow, into the chamber 720 from the end portion of the inlet passage member 740 and toward the chamber outlet 750.

While the depicted embodiment the middle inlet passage member 740 only includes one spiral-channel outlet of the inlet passage member 740 (to enter the chamber 720), in some embodiments the inlet passage member 740 could include multiple spiral-channel outlets. In some of those embodiments, the multiple spiral-channel outlets can be symmetrically or evenly distributed in the venous end cap 700 so as to minimize turbulence in the blood and to balance the flow symmetrically within the chamber 720.

While the structures of the venous end cap 700 that function to deaerate liquids are described above in the context of an end cap of a dialyzer, it should be understood that the structures for deaeration can be incorporated in conjunction with various other types of devices, or as a deaeration device to itself. That is, the structures for deaeration of the venous end cap 700 can be incorporated as portions of a deaeration chamber that can be implemented in a wide variety of suitable embodiments. Additionally, while the venous end cap 700 is primarily intended to deaerate blood, priming solution, or other medical liquids, it should be understood that the structures for deaeration of the venous end cap 700 can be implemented in other embodiments so as to deaerate other types of liquids.

Referring to FIGS. 45-47, another alternative second (venous) end cap 800 can be used with any of the dialyzers described herein. The venous end cap 800 is configured with particular features to encourage separation and collection of gases, such as air, from the extracorporeal circuit. For example, the venous end cap 800 includes a reconfigurable popper cap, as described further below.

The venous end cap 800 includes one or more peripheral inlets 810 (or a plurality of peripheral inlets 810), an outlet 820, a reconfigurable dome 840 (or flexible dome), an air purge member 850, and a chamber 860. In FIG. 47, the dome 840 and air purge member 850 are not shown in order to provide better visibility of the structures inside of the chamber 860. In FIG. 45, the reconfigurable dome 840 is in a first, inverted configuration such that the chamber 860 essentially does not exist, or only minimally exists. In FIG. 46, the reconfigurable dome 840 is in a second, domed configuration such that the chamber 860 is defined. The chamber 860 is larger when the reconfigurable dome 840 is in the second configuration as compared to the first configuration.

The one or more of peripheral inlets 810 are passageways that allow liquid exiting from the hollow fibers of the dialyzer to enter the chamber 860. After entering the chamber 860, the liquid dwells for a time in the chamber 860 and then exits the chamber 860 via the outlet 820. The outlet 820 is in the side wall of a lower portion of the housing and at a lower elevation than the one or more peripheral inlets 810. Said another way, the when the reconfigurable dome 850 is in the second, domed configuration, the outlet 820 is on an opposite side of the one or more peripheral inlets 810 in comparison to the reconfigurable dome 850.

In some embodiments, the outlet 820 is positioned at other locations. For example, in some embodiments the outlet 820 is positioned at the center and bottom of the concave lower portion of the chamber 860, as depicted by an outlet 820' shown in FIG. 47. In this location, the outlet 820' is surrounded by the one or more peripheral inlets 810 and equidistant from each inlet of the one or more peripheral inlets 810. In some embodiments, multiple outlets are included. For example, in some embodiments the outlet 820 and the outlet 820' are each included in a single embodiment.

In some embodiments, there are multiple peripheral inlets 810 (e.g., six in the depicted embodiment) spaced apart from each other around the periphery of the chamber 860 so that the liquid (e.g., priming solution, blood, etc.) entering the chamber 860 does so at a low velocity. By maintaining a low liquid flow velocity in the chamber 860, more time is allowed for air in the liquid to rise (i.e., to separate from the liquid) due to the effects gravity. However using this low velocity approach tends to make flushing air from a conventional chamber in a conventional end cap during the priming phase more difficult. The special popper cap (i.e., the reconfigurable dome 840) of the venous end cap 800 helps to mitigate this issue.

The reconfigurable dome 840 (or flexible dome 840) is a hemi-spherical member made of a semi-flexible material. The natural, least stressed configuration of the reconfigurable dome 840 is the shape shown in FIG. 46 (the dome shape, domed configuration, or the second configuration). The second configuration (domed shape) of the reconfigurable dome 840 is a more stable configuration than the first configuration (inverted configuration). However, the reconfigurable dome 840 will also maintain its inverted configuration shown in FIG. 45. The inverted configuration is the initial configuration of the reconfigurable dome 840 (i.e., the configuration of the reconfigurable dome 840 prior to priming or use). The reconfigurable dome 840 (or flexible dome 840) will reconfiguration from the first configuration (inverted configuration) to the second configuration (domed configuration) in response to pressurization within the chamber 860.

During priming, as liquid passes through the one or more inlets 810, the liquid will apply forces to the inner surface of the inverted reconfigurable dome 840. The reconfigurable dome 840 will begin to deflect upward in response to the forces of the liquid, and the chamber 860 will thereby begin to form. When the reconfigurable dome 840 has deflected upward to threshold extent, the reconfigurable dome 840 will naturally tend to break through or pop open toward the dome configuration shown in FIG. 46 in which the chamber 860 is fully formed. Advantageously, because the chamber 860 essentially does not exist, or only minimally exists, during initial priming, there is essentially no air that needs to be flushed out by the liquid priming process. However, after the chamber 860 has been formed, the chamber 860 functions to separate air/gas from the blood during use.

While the structures of the venous end cap 800 that function to deaerate liquids are described above in the context of an end cap of a dialyzer, it should be understood that the structures for deaeration can be incorporated in conjunction with various other types of devices, or as a deaeration device to itself. That is, the structures for deaeration of the venous end cap 800 can be incorporated as portions of a deaeration chamber that can be implemented in a wide variety of suitable embodiments. Additionally, while the venous end cap 800 is primarily intended to deaerate blood, priming solution, or other medical liquids, it should be understood that the structures for deaeration of the venous end cap 800 can be implemented in other embodiments so as to deaerate other types of liquids.

Multiple differing types of dialyzer venous end caps with structures for deaerating liquids are described above (e.g., venous end cap 600, venous end cap 700, and venous end cap 800). It should be understood that features of the various venous end caps 600, 700, and/or 800 can be mixed, combined, added on, substituted for other features, and the like so, as to create hybrid designs that are within the scope of this disclosure. For example, while the venous end cap 800 is described as having the reconfigurable dome 840, in some embodiments a rigid/fixed dome (e.g., the dome 640, or the dome 710) can be substituted for the reconfigurable dome 840. Conversely, while the venous end cap 600 and the venous end cap 700 are described as having rigid/fixed domes, in some embodiments a reconfigurable dome (such as the reconfigurable dome 840) can be substituted instead of the rigid/fixed domes. The inlet and/or outlet configurations and/or locations of the various venous end caps 600, 700, and/or 800 can also be substituted, or added, across the various designs. By way of these examples, it should be understood that all possible hybrid designs using the features of the various venous end caps 600, 700, and/or 800 are envisioned and within the scope of this disclosure.

The deaeration chambers described herein are designed to separate gases (e.g., air) from liquids (e.g., blood) by facilitating the gases that have a lower density than liquids to naturally migrate upward toward the domes of the deaeration chambers. Accordingly, it can be said that the domes are, or comprise, the upper portion of the deaeration chambers. The end of the deaeration chamber that is opposite of the dome can be referred to as the lower or bottom portion, or referred to as positioned below the dome. Hence, terms such as above, below, upper, lower, top, and bottom can be used to define particular portions, positions, or directions in the context of the deaeration chambers described herein. Additionally, the dialyzers described herein can be configured for attachment to a blood treatment machine (e.g., the treatment module 220) such that the second end cap (venous end cap) is above the first end cap (arterial end cap).

The devices and methods described above are examples of the innovative aspects disclosed herein. As described below, without limitation, other embodiments and alternatives are also encompassed by the scope of this disclosure.

While the clamps 242 and 244 are described as functioning as on/off valves, in some embodiments, the clamps 242 and 244 are used to variably modulate the flow of blood through the arterial line 102 and/or the venous line 104 (e.g., across a range of partially restricted clamp settings).

While the first end cap 120 and the second end cap 140 have been described as having a particular arrangement of ports and pressure chambers, in some embodiments the end caps have other arrangements of the ports and pressure chambers.

While the treatment module 220 is described as being cantilevered from the blood treatment machine console 210 by the adjustable arm 280, in some embodiments the treatment module 220 is attached to the blood treatment machine console 210 by a pivot mechanism, directly attached, or integrated therein. In some such cases, the arterial line 102 and the venous line 102 can be more than a meter in length.

While the dialyzer 100 has been described as having the integral pressure detection chambers 122 and 142, in some embodiments arterial and/or venous pressure detection is performed at positions along the arterial line 102 and/or the venous line 102 rather than at dialyzer 100. In such a case, the pressure detection chambers 122 and/or 142 are eliminated from the dialyzer 100 (although the dialyzer 100 may still include an integrated magnetic pump rotor, e.g., rotor 132 or rotor 137).

While the dialyzer 100 has been described as having an integral magnetic pump rotor (e.g., rotor 132 or rotor 137), in some embodiments a peristaltic pump acting on the arterial line 102 is included instead. In such a case, the rotor is eliminated from the dialyzer 100 (although the dialyzer 100 may still include the integrated pressure detection chamber(s) 122 and/or 142). Some examples utilize other blood-pumping mechanisms (e.g., diaphragm pumps, screw pumps, piston pumps, peristaltic pumps, and the like).

While components of the dialyzer 100 such as the magnetic pump rotor (e.g., rotor 132 or rotor 137) and the pressure detection chambers 122 and 142 have been described as being integrated into the end caps 120 and 140 of the dialyzer 100, in some embodiments one or more of such components can be integrated into portions of the dialyzer 100 other than the end caps 120 and 140.

While the blood flow path through the dialyzer 100 has been illustrated as proceeding upward from the first end cap 120 at the bottom of the dialyzer 100 to the second end cap 140 at the top of the dialyzer 100, in some embodiments the blood flow path through the dialyzer 100 can proceed downward from the second end cap 140 at the top of the dialyzer 100 to the first end cap 120 at the bottom of the dialyzer 100. In such a case, in some embodiments the integrated magnetic pump rotor can be located in the second end cap 140 at the top of the dialyzer 100.

While some examples include a treatment module 220 that is cantilevered from a blood treatment machine console 210 by an arm 280, it should be understood that other examples have these components integrated as a single unit in a shared housing. Moreover, some examples have a treatment module that is not mechanically supported by the console. For example, some have treatment modules that are mounted to another structure (e.g., a wall or wall bracket, or a floor stand), or which are to be placed on a surface, such as a desk or table. Such examples may include flexible fluid tubes and electrical cables between the modules and consoles to transfer fluids and electricity/signals. Other examples have treatment modules that can receive power separately from the console and/or have wireless communication channels with the console.

While deaeration chambers have been described in the context of venous end caps of dialyzers, the deaeration chamber concepts can also be implemented in the context of standalone medical fluid deaeration chamber devices, apart from dialyzers, or as a part of any other suitable fluid handling device.

A number of embodiments of the invention have been described. Nevertheless, it will be understood that various modifications may be made without departing from the spirit and scope of the invention. Accordingly, other embodiments are within the scope of the following claims.

What is claimed is:

1. A deaeration chamber comprising:
a housing including a top portion and a bottom portion, the housing defining a central axis and a chamber between the top and bottom portions; and
an inlet passage member extending within the chamber from the bottom portion, the inlet passage member extending toward the top portion along the central axis, an end portion of the inlet passage member defining a spiral-channel outlet through which liquid enters the chamber,
wherein the bottom portion defines a chamber outlet below the spiral-channel outlet and wherein the chamber outlet is farther from the central axis than the spiral-channel outlet.

2. The deaeration chamber of claim 1, wherein the top portion includes a dome that partially defines the chamber, and wherein the chamber outlet is positioned on an opposite side of the spiral-channel outlet in comparison to the dome.

3. The deaeration chamber of claim 2, further comprising an air purge member attached to the dome to allow gases to exit the chamber while preventing liquids from exiting therethrough.

4. The deaeration chamber of claim 2, wherein the dome is hemi-spherical.

5. The deaeration chamber of claim 1, wherein the spiral-channel outlet is offset from the central axis of the housing.

6. The deaeration chamber of claim 1, wherein the chamber outlet is on an outer side of the housing.

7. The deaeration chamber of claim 1, wherein the housing includes a port for administering medicaments or extracting a sample of the liquid.

8. The deaeration chamber of claim 1, wherein the spiral-channel outlet includes a beveled surface at an acute angle in relation to the central axis.

9. The deaeration chamber of claim 1, wherein the spiral-channel outlet is closer to a top of the chamber than to a bottom of the chamber.

10. The deaeration chamber of claim 1, wherein the deaeration chamber is a medical fluid deaeration chamber or a blood deaeration chamber.

11. A dialysis treatment apparatus comprising:
an elongate housing defining a central longitudinal axis and including first and second end caps at opposite ends of the housing; and
a plurality of hollow membranous fibers within an interior of the housing between the first and second end caps,
wherein the second end cap defines a chamber and an inlet passage member extending within the chamber along the central longitudinal axis from a bottom of the chamber toward a top of the chamber, the second end cap configured such that when a liquid passes through the hollow membranous fibers the liquid enters the inlet passage member and passes through spiral-channel outlet of the inlet passage member to enter the chamber, and
wherein the second end cap defines a chamber outlet below the spiral-channel outlet.

12. The dialysis treatment apparatus of claim 11, wherein the chamber outlet is defined by the bottom of the chamber.

13. The dialysis treatment apparatus of claim 11, wherein the spiral-channel outlet is offset from the central longitudinal axis of the housing.

14. The dialysis treatment apparatus of claim 11, wherein the chamber outlet is positioned between the spiral-channel outlet and the plurality of hollow membranous fibers.

15. The dialysis treatment apparatus of claim 14, wherein the chamber outlet is offset from the central longitudinal axis of the housing.

16. The dialysis treatment apparatus of claim 11, wherein the second end cap includes a dome that partially defines the chamber.

17. The dialysis treatment apparatus of claim 16, wherein the dome is hemi-spherical.

18. The dialysis treatment apparatus of claim 11, wherein the chamber is configured to de-aerate the liquid flowing into the second end cap.

19. The dialysis treatment apparatus of claim 11, wherein the second end cap defines a substituate liquid inlet port in fluid communication with an outgoing fluid flow path exiting from the chamber.

20. The dialysis treatment apparatus of claim 19, further comprising a check valve along the outgoing fluid flow path.

21. The dialysis treatment apparatus of claim 20, wherein the second end cap includes a port for administering medicaments or extracting a sample of the liquid.

22. The dialysis treatment apparatus of claim 11, further comprising an air purge member attached to the second end cap to allow gases to exit the chamber while preventing liquids from exiting therethrough.

\* \* \* \* \*